(12) United States Patent
Zhang

(10) Patent No.: US 12,268,785 B2
(45) Date of Patent: Apr. 8, 2025

(54) COATED EDIBLE PLANT-DERIVED MICROVESICLE COMPOSITIONS AND METHODS FOR USING THE SAME

(71) Applicant: University of Louisville Research Foundation, Inc., Louisville, KY (US)

(72) Inventor: Huang-Ge Zhang, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 16/377,800

(22) Filed: Apr. 8, 2019

(65) Prior Publication Data

US 2019/0365658 A1 Dec. 5, 2019

Related U.S. Application Data

(63) Continuation of application No. 15/303,250, filed as application No. PCT/US2015/025337 on Apr. 10, 2015, now abandoned.

(60) Provisional application No. 61/978,434, filed on Apr. 11, 2014.

(51) Int. Cl.
| | |
|---|---|
| *A61K 9/51* | (2006.01) |
| *A61K 9/00* | (2006.01) |
| *A61K 9/50* | (2006.01) |
| *A61K 31/05* | (2006.01) |
| *A61K 31/12* | (2006.01) |
| *A61K 31/203* | (2006.01) |
| *A61K 31/337* | (2006.01) |
| *A61K 31/352* | (2006.01) |
| *A61K 31/353* | (2006.01) |
| *A61K 31/475* | (2006.01) |
| *A61K 31/513* | (2006.01) |
| *A61K 31/704* | (2006.01) |
| *A61K 33/243* | (2019.01) |
| *A61K 35/17* | (2015.01) |
| *A61P 29/00* | (2006.01) |
| *A61P 35/00* | (2006.01) |

(52) U.S. Cl.
CPC ............. *A61K 9/51* (2013.01); *A61K 9/0019* (2013.01); *A61K 9/5068* (2013.01); *A61K 31/05* (2013.01); *A61K 31/12* (2013.01); *A61K 31/203* (2013.01); *A61K 31/337* (2013.01); *A61K 31/352* (2013.01); *A61K 31/353* (2013.01); *A61K 31/475* (2013.01); *A61K 31/513* (2013.01); *A61K 31/704* (2013.01); *A61K 33/243* (2019.01); *A61K 35/17* (2013.01); *A61P 29/00* (2018.01); *A61P 35/00* (2018.01)

(58) Field of Classification Search
CPC ...... A61K 9/51; A61K 9/0019; A61K 9/5068; A61K 31/05; A61K 31/12; A61K 31/203; A61K 31/337; A61K 31/352; A61K 31/353; A61K 31/475; A61K 31/513; A61K 31/704; A61K 33/243; A61K 35/17; A61P 29/00; A61P 35/00

See application file for complete search history.

(56) References Cited

U.S. PATENT DOCUMENTS

| | | |
|---|---|---|
| 7,897,356 B2 | 3/2011 | Klass et al. |
| 9,717,733 B2 | 8/2017 | Zhang |
| 9,752,148 B2 | 9/2017 | Zhang |
| 10,590,171 B2 | 3/2020 | Silvas et al. |
| 2010/0048888 A1 | 2/2010 | Chen et al. |
| 2010/0209415 A1 | 8/2010 | Smith et al. |
| 2010/0298151 A1 | 11/2010 | Taylor et al. |
| 2011/0010817 A1 | 1/2011 | Théberge et al. |
| 2012/0183575 A1 | 7/2012 | Gabrielsson |
| 2012/0315324 A1 | 12/2012 | Zhang |
| 2013/0115241 A1* | 5/2013 | Gho ............... A61K 49/0097 424/192.1 |
| 2013/0129790 A1 | 5/2013 | Alexis et al. |
| 2014/0093557 A1 | 4/2014 | Zhang |
| 2014/0308212 A1 | 10/2014 | Zhang |
| 2016/0045448 A1 | 2/2016 | Zhang |
| 2016/0354313 A1 | 12/2016 | De Beer et al. |
| 2017/0035700 A1 | 2/2017 | Zhang |
| 2019/0382539 A1 | 12/2019 | Zhang |
| 2020/0046788 A1 | 2/2020 | Zhang |
| 2020/0063208 A1 | 2/2020 | Zhang |
| 2020/0188311 A1 | 6/2020 | Zhang |

(Continued)

FOREIGN PATENT DOCUMENTS

| | | |
|---|---|---|
| AU | 2008207735 | 7/2008 |
| EP | 3 129 010 | 12/2019 |

(Continued)

OTHER PUBLICATIONS

Antonyak & Cerione, Microvesicles as mediators of intercellular communication in cancer. Methods in molecular biology. 2014; 1165:147-173.

(Continued)

*Primary Examiner* — Jessica Worsham

(74) *Attorney, Agent, or Firm* — Meunier Carlin & Curfman LLC

(57) ABSTRACT

Compositions are provided that comprise a microvesicle derived from an edible plant. The microvesicles are coated with a plasma membrane derived from a targeting cell and can further be utilized to encapsulate a therapeutic agent. Methods for treating an inflammatory disorder and/or a cancer are further provided and include the step of administering to a subject an effective amount of a composition that includes a microvesicle coated with a plasma membrane derived from a targeting cell.

11 Claims, 42 Drawing Sheets

(56) References Cited

U.S. PATENT DOCUMENTS

| | | |
|---|---|---|
| 2020/0206297 A1 | 7/2020 | Zhang |
| 2021/0085744 A1 | 3/2021 | Zhang |
| 2021/0236612 A1 | 8/2021 | Zhang |
| 2022/0142937 A1 | 5/2022 | Zhang |

FOREIGN PATENT DOCUMENTS

| | | | |
|---|---|---|---|
| WO | WO 2004/019916 | | 3/2004 |
| WO | WO 2008/092153 | | 7/2008 |
| WO | WO 2009/065561 | | 5/2009 |
| WO | WO 2009/147519 | | 12/2009 |
| WO | WO 2010/096597 | | 8/2010 |
| WO | WO 2011/097480 | | 8/2011 |
| WO | WO-2013048734 A1 * | | 4/2013 |
| WO | WO-2013070324 A1 * | | 5/2013 |
| WO | WO 2015/058148 | | 4/2015 |
| WO | WO 2017/004526 | | 1/2017 |
| WO | WO-2017/083068 A1 | | 5/2017 |
| WO | WO 2017/176792 | | 10/2017 |
| WO | WO 2018/039119 | | 3/2018 |
| WO | WO 2018/071806 | | 4/2018 |
| WO | WO 2018/098247 | | 5/2018 |
| WO | WO-2018/107061 A1 | | 6/2018 |
| WO | WO 2019/104242 | | 5/2019 |
| WO | WO 2019/173487 | | 9/2019 |
| WO | WO-2019/195179 A1 | | 10/2019 |
| WO | WO 2019/210189 | | 10/2019 |
| WO | WO-2020/041783 A1 | | 2/2020 |
| WO | WO-2020/180801 A1 | | 9/2020 |
| WO | WO-2021/237215 A1 | | 11/2021 |

OTHER PUBLICATIONS

Arora et al. Synthesis, characterization and evaluation of poly (D,L-lactide-co-glycolide)-based nanoformulation of miRNA-150: potential implications for pancreatic cancer therapy. Int J Nanomedicine, Jun. 18, 2014, vol. 9, pp. 2933-2942.
Azmi et al., Exosomes in Cancer Development, Metastasis and Drug Resistance: A Comprehensive Review, Cancer Metastasis Rev. Dec. 2013; 32(0). have.
Blaskovich., Discovery of JSI-124, a selective janus kinase signal transducer and activator of transcription 3 signaling pathway inhibitor with potent antitumor activity against human and murine cancer cells in mice, Can Res, 2003, 63, 1270-1279. have.
Moorthi et al., Nanotherapeutics to overcome conventional cancer chemotherapy limitations. J Pharm Pharm Sci 14, 67-77 (2011).
Cho et al., "Therapeutic nanoparticles for drug delivery in cancer," Clin. Cancer Res., 2008, vol. 14:(5), pp. 1310-1316.
Cho., MicroRNAs as therapeutic targets and their potential applications in cancer therapy. Expert opinion on therapeutic targets. 2012; 16(8):747-759.
Decision to Grant corresponding to European Patent No. 15 776 590.0-1112 dated Nov. 7, 2019.
D'Souza-Schorey et al., Tumor-derived microvesicles: shedding light on novel microenvironment modulators and prospective cancer biomarkers. Genes & development. 2012; 26(12):1287-1299.
Geng et al., MicroRNA-192 suppresses liver metastasis of colon cancer, Oncogene, vol. 33, pp. 5332-5340. (Year: 2014). have.
Hata et al., Dysregulation of microRNA biogenesis and gene silencing in cancer. Science signaling. 2015; 8(368):re3.
Hirsjarvi et al., Passive and active tumour targeting with nanocarriers. Curr Drug Discov Technol 8, 188-196 (2011).
Intention to Grant corresponding to European Patent Application No. 15776590.0 dated Jun. 19, 2019.
International Preliminary Report on Patentability corresponding to International Patent Application No. PCT/US2011/023747 dated Aug. 7, 2012. have.
Jiang et al., Quantitatively controlling expression of miR-1792 determines colon tumor progression in a mouse tumor model. The American journal of pathology. 2014; 184(5):1355-1368.
Jiang et al., Restoration of miR17/20a in solid tumor cells enhances the natural killer cell antitumor activity by targeting Mekk2. Cancer immunology research 2: 789-799. (2014).
Joshi et al., MicroRNAs in lung cancer. World journal of methodology. 2014; 4(2):59-72.
Kolhatkar et al., Active tumor targeting of nanomaterials using folic acid, transferrin and integrin receptors. Curr Drug Discov Technol 8, 197-206 (2011).
Krishna et al. "An efficient targeted drug delivery through apotransferrin loaded nanoparticles," Plos One, 2009, vol. 4(10), e7240.
Kularatne et al., Targeting of nanoparticles: folate receptor. Methods in molecular biology 624: 249-265. (2010).
Kwon et al., Analysis on the current status of targeted drug delivery to tumors. J Control Release, doi:10.1016/j.jconrel.2012.07.010 (2012).
Markman, "Pegylated liposomal doxorubicin in the treatment of cancer of the breast and ovary," Expert Opin. Pharmacother, 2006, vol. 7, pp. 1469-1474.
Nakano et al., Extracellular vesicles in the biology of brain tumour stem cells—Implications for inter-cellular communication, therapy and biomarker development. Seminars in cell & developmental biology. 2015; 40:17-26.
Office Action corresponding with European Patent Application No. 15 776 590.0-1112 dated Nov. 6, 2018.
Office Action corresponding with European Patent Application No. 16818891.0 dated Jan. 9, 2019.
Office Action corresponding to U.S. Appl. No. 15/821,408 dated Nov. 12, 2019.
Office action (Restriction Requirement) corresponding to U.S. Appl. No. 13/576,907 dated Mar. 27, 2013.
Office Action corresponding to U.S. Appl. No. 13/576,907 dated Jun. 18, 2013.
Office action (Restriction Requirement) corresponding to U.S. Appl. No. 14/107,691 dated Feb. 13, 2014.
Office Action corresponding to U.S. Appl. No. 14/107,691 dated Jun. 19, 2014.
Office Action corresponding to U.S. Appl. No. 14/107,691 dated Feb. 6, 2015.
Office Action corresponding to U.S. Appl. No. 14/107,691 dated Oct. 6, 2015.
Office Action corresponding to U.S. Appl. No. 14/107,691 dated Jun. 28, 2016.
Office Action corresponding to U.S. Appl. No. 14/107,691 dated Mar. 14, 2017.
Office Action corresponding to U.S. Appl. No. 14/107,691 dated Sep. 13, 2017.
Office Action (Restriction Requirement) corresponding to U.S. Appl. No. 15/917,151 dated Apr. 20, 2018.
Office Action corresponding to U.S. Appl. No. 15/917,151 dated Sep. 21, 2018.
Office Action corresponding to U.S. Appl. No. 15/740,591 dated Apr. 24, 2019.
Office Action corresponding to U.S. Appl. No. 15/740,591 dated Aug. 13, 2019.
Office Action (Restriction Requirement) corresponding to U.S. Appl. No. 15/821,408 dated May 2, 2019.
Office Action (Restriction Requirement) corresponding to U.S. Appl. No. 16/523,761 dated Nov. 5, 2019.
United States Patent and Trademark Office, International Search Report and Written Opinion issued in corresponding Application No. PCT/US15/25337, mailed Jul. 1, 2015.
United States Patent and Trademark Office, International Search Report and Written Opinion issued in corresponding Application No. PCT/US16/040710, mailed Sep. 23, 2016.
USPTO/ISA, International Search Report and Written Opinion in corresponding international application PCT/ US2011/023747, completed Mar. 22, 2011.
Vader et al., Extracellular vesicles: emerging targets for cancer therapy. Trends in molecular medicine. 2014; 20(7):385-393.
Xue et al., Solid lipid-PEI hybrid nanocarrier: An integrated approach to provide extended, targeted, and safer siRNA therapy of prostate cancer in an all-in-one manner, ACS Nano, vol. 5, pp. 7034-7047. (Year: 2011). have.

(56) References Cited

OTHER PUBLICATIONS

Extended European Search Report for EP Application No. 17875026. 1, 20 pgs., dated Jul. 2, 2020.
Min-Ji Bak et al., "6-Shogaol-Rich Extract from Ginger Up-Regulates the Antioxidant Defense Systems in Cells and Mice," Molecules, vol. 17, No. 7, Jul. 4, 2012, pp. 8037-8055.
Mueller et al., "Examination of the Anti-Inflammatory, Antioxidant, and Xenobiotic-Inducing Potential of Broccoli Extract and Various Essential Oils during a Mild DSS-Induced Colitis in Rats," ISRN Gastroenterology, vol. 2013, Jan. 20, 2013, pp. 1-14.
Notice of Allowance corresponding to U.S. Appl. No. 16/523,761 dated Jun. 11, 2020.
Notice of Allowance corresponding to U.S. Appl. No. 15/948,218 dated Apr. 27, 2020.
Office Action corresponding to U.S. Appl. No. 15/740,591 dated Mar. 9, 2020.
Office Action corresponding to U.S. Appl. No. 16/523,761 dated Jan. 31, 2020.
Office Action corresponding to U.S. Appl. No. 16/359,618 dated Aug. 10, 2020.
Zhang et al. (2016) "Plant derived edible nanoparticles as a new therapeutic approach against diseases," Tissue Barriers, vol. 4, No. 2, pp. 1-9, specif. p. 1.
Examination Report for AU Patent Application No. 2016288643, 5 pages, dated Aug. 18, 2020.
Greaney et al. (2016) "Sulforaphane Inhibits Multiple Inflammasomes through an Nrf2-Independent Mechanism," Journal of Leukocyte Biology, vol. 99, pp. 189-199.
He et al. (2014) "MIR-23a Functions as a Tumor Suppressor in Osteosarcoma," Cell Physiol Biochem, vol. 34, pp. 1485-1496.
International Preliminary Report on Patentability corresponding to International Application No. PCT/US12/056298, mailed May 22, 2014.
International Search Report and Written Opinion issued in corresponding International Application No. PCT/US19/29377, dated Sep. 9, 2019, 12 pages.
International Search Report and Written Opinion issued in corresponding Application No. PCT/US19/020971, mailed May 23, 2019.
International Search Report and Written Opinion issued in corresponding Application No. PCT/US18/062349, mailed Apr. 29, 2019.
International Preliminary Report on Patentability corresponding to International Application No. PCT/US18/062349, mailed May 26, 2020.
International Preliminary Report on Patentability corresponding to International Application No. PCT/US17/056570, mailed Apr. 25, 2019.
International Preliminary Report on Patentability corresponding to International Application No. PCT/US17/062970, mailed Jun. 6, 2019.
Long et al. (2009) "Let-7a MicroRNA Functions as a Potential Tumor Suppressor in Human Laryngeal Cancer," Oncology Reports, vol. 22, pp. 1189-1195.
Office Action corresponding with European Patent Application No. 16818891.0 dated Feb. 1, 2021.
Office Action corresponding with European Patent Application No. 17875026.1 dated Apr. 9, 2021.
Office Action corresponding to U.S. Appl. No. 15/740,591 dated May 26, 2021.
Office Action corresponding to U.S. Appl. No. 16/340,457 dated Mar. 22, 2021.
Office Action corresponding to U.S. Appl. No. 16/359,618 dated Apr. 26, 2021.
Office Action (Restriction Requirement) corresponding to U.S. Appl. No. 16/383,085 dated Dec. 15, 2020.
Office Action (Restriction Requirement) corresponding to U.S. Appl. No. 16/462,715 dated Nov. 20, 2020.
Office Action (Restriction Requirement) corresponding to U.S. Appl. No. 16/462,715 dated Apr. 9, 2021.
Ogata-Kawata et al. (2014) "Circulating Exosomal MicroRNAs as Biomarkers of Colon Cancer," PLOS One, vol. 9, No. 4, pp. 1-9.
Tristan-Ramos (2020) "The Tumor Suppressor MicroRNA let-7 Inhibits Human LINE-1 Retrotransposition," Nature Communications, vol. 11, No. 5712, pp. 1-14.
Wagner et al. (2013) "DSS-Induced Acute Colitis in C57BL/6 Mice is Mitigated by Sulforaphane Pre-Treatment," Journal of Nutritional Biochemistry, vol. 24, pp. 2085-2091.
Wang, et al., "Blood Exosomes Regulate the Tissue Distribution of Grapefruit-Derived Nanovector via CD36 and IGFR1 Pathways", Theranostics, 8(18):4912-4924 (Sep. 9, 2018).
Baier et al. "MicroRNAs Are Absorbed in Biologically Meaningful Amounts from Nutritionally Relevant Doses of Cow Milk and Affect Gene Expression in Peripheral Blood Mononuclear Cells, HEK-293 Kidney Cell Cultures, and Mouse Livers," The Journal of Nutrition, 2014, vol. 144, No. 10, pp. 1495-1500.
Deng et al. "Exosomes miR-126a Released 1-1 from MDSC Induced by DOX Treatment Promotes Lung Metastasis," Oncogene, 2017, vol. 36, No. 5, pp. 639-651.
Dryden (2011) "Phase I Clinical Trial Investigating the Ability of Plant Exosomes to Deliver Curcumin to Normal and Malignant Colon Tissue".
European Patent Office, Extended European Search Report, EP Application No. 19793847.5, 8 pgs., dated Apr. 8, 2022.
Examination Report for AU Patent Application No. 2016288643 dated Jul. 1, 2021.
Examination Report for CA Patent Application No. 3,029,602 dated Aug. 26, 2022.
Examination Report for CA Patent Application No. 3,029,602 dated May 5, 2023.
Examination Report for IN Patent Application No. 201817004051 dated Nov. 25, 2021.
International Preliminary Report corresponding to International Patent Application Serial No. PCT/US 2021/033913 dated Nov. 17, 2022.
International Search Report and Written Opinion corresponding to International Patent Application Serial No. PCT/US2021/033913 dated Oct. 6, 2021.
Ionescu et al. "The Interplay Between Gut Microbiota and miRNAs in Cardiovascular Diseases," Frontiers in Cardiovascular Medicine, 2022, vol. 9, Art. 856901, pp. 1-14.
Notice of Allowance corresponding to U.S. Appl. No. 16/383,085 dated Sep. 11, 2023.
Office Action (Restriction Requirement) corresponding to U.S. Appl. No. 16/816,214 dated Sep. 28, 2021.
Office Action corresponding to U.S. Appl. No. 17/050,200 dated Feb. 17, 2022.
Office Action corresponding to U.S. Appl. No. 16/359,618 dated Feb. 10, 2022.
Office Action corresponding to U.S. Appl. No. 16/383,085 dated Sep. 24, 2021.
Office Action corresponding to U.S. Appl. No. 16/383,085 dated Apr. 7, 2022.
Office Action corresponding to U.S. Appl. No. 16/383,085 dated Sep. 15, 2022.
Office Action corresponding to U.S. Appl. No. 16/383,085 dated Mar. 20, 2023.
Office Action corresponding to U.S. Appl. No. 16/462,715 dated Dec. 27, 2021.
Office Action corresponding to U.S. Appl. No. 16/462,715 dated Aug. 2, 2022.
Office Action corresponding to U.S. Appl. No. 16/462,715 dated Apr. 4, 2023.
Office Action corresponding to U.S. Appl. No. 16/816,214 dated May 13, 2022.
Office Action corresponding to U.S. Appl. No. 16/766,055 dated Dec. 2, 2022.
Office Action corresponding to U.S. Appl. No. 16/766,055 dated Aug. 4, 2023.
Office Action corresponding to U.S. Appl. No. 17/889,715 dated Oct. 5, 2023.
Office Action corresponding with Chinese Patent Application No. 201680049762.8 dated Jul. 1, 2021.

(56) References Cited

OTHER PUBLICATIONS

Office Action corresponding with European Patent Application No. 16818891.0 dated Oct. 4, 2021.
Office Action corresponding with European Patent Application No. 16818891.0 dated Mar. 23, 2023.
Teng et al. (2018) "Plant-Derived Exosomal MicroRNAs Shape the Gut Microbiota," Cell Host & Microbe, vol. 24, pp. 637-652 plus Methods Addendum, pp. e1-e8; specifically p. 637, 639, and e3.
Zhang et al. (2016) "Do ginger-derived nanoparticles represent an attractive treatment strategy for inflammatory bowel disease?" website article published on Nov. 4, 2016 and/or Nanomedicine (Lond.), vol. 11(23), pp. 3035-3037.

\* cited by examiner

Human leukocytes

COATED EDIBLE PLANT-DERIVED MICROVESICLE COMPOSITIONS AND METHODS FOR USING THE SAME

RELATED APPLICATIONS

This application is a continuation of U.S. patent application Ser. No. 15/303,250 (pending), filed Oct. 11, 2016, which itself is a U.S. National Stage application of PCT International Patent Application Serial No. PCT/US2015/025337, filed Apr. 10, 2015, which itself claims priority to U.S. Provisional Application Ser. No. 61/978,434, filed Apr. 11, 2014. The entire disclosure of each of these applications is incorporated herein by this reference.

GOVERNMENT INTEREST

This invention was made with government support under grant number UH2TR000875 awarded by the National Institutes of Health. The government has certain rights in the invention.

TECHNICAL FIELD

The presently-disclosed subject matter relates to coated edible plant-derived microvesicle compositions and methods of using the same for the diagnosis and treatment of disease. In particular, the presently-disclosed subject matter relates to compositions that include edible plant-derived microvesicles having a targeting cell-derived plasma membrane coating and that are useful in the treatment of disease.

BACKGROUND

Inflammation is a hallmark of most diseases including cancer, autoimmune disease, and infectious disease. The development of target-specific delivery systems to inflammatory sites is urgently needed. The attraction of leukocytes, including T cells, to sites of inflammation and infection is an essential component of the host response to disease, including autoimmune and chronic inflammatory diseases as well as infectious disease and cancer. Recruitment of circulating T cells to sites of pathogen entry or inflammation involves at least two separate migration processes, termed extravasation and chemotaxis. Adhesion to the luminal side of blood vessels, transendothelial migration, and subsequent chemotaxis of leukocytes are highly complex processes. Chemokines and their receptors play a coordinating role in both the homeostatic circulation of T cells, as well as their movement to sites of inflammation or injury. Once T cells are within inflammatory tissue, their response can be affected by the many inflammatory chemokines that are overexpressed and have broad target cell selectivity. The fact that there is a redundancy within the chemokine network with respect to ligand-receptor binding and that an array of chemokines are overexpressed by a variety of cells in inflammatory tissues makes the use of chemokines a potential component for the development of therapeutic targeting.

For a therapeutic agent to exert its desired effect it needs to (1) reach the desired site and (2) be in physical contact with its target. The development of target-specific delivery systems has not yet been broadly successful. Despite many potential advantages for using nanoparticles and liposomes, hurdles to their use include cytotoxicity, induction of chronic inflammation, host immune responses, difficulties of large scale production at affordable prices, and potential biohazards to the environment. Unlike the situation with artificially synthesized nanoparticles, naturally released nano-sized exosomes derived from many different types of mammalian cells play an important role in intercellular communication. Nano-sized exosomes released from mammalian cells have been utilized for encapsulating drugs and siRNA to treat diseases in mouse disease models without side-effects. Although this approach is promising, production of large quantities of mammalian cell nanoparticles and evaluation of their potential biohazards has been challenging. Exosoine-like nanoparticles from the tissue of edible plants including grapefruit, grapes, and tomatoes were recently identified, and produced in large quantities. See, e.g., International Patent Application Publication No. WO 2013/070324, which is incorporated herein by this reference. As with mammalian exosomes, it was demonstrated that exosome-like nanoparticles from grapes naturally encapsulate small RNAs, proteins, and lipids. Using both in vitro cell culture models as well as mouse models, it was shown that grapefruit GNVs are highly efficient for delivering a variety of therapeutic agents including drugs, DNA expression vectors, siRNA and antibodies. Despite the promise of those nanovectors, however, efficient and effective targeting of the nanovectors to inflamed and/or diseased tissue remains an issue.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes coated edible plant-derived microvesicle compositions and methods of using the same for the diagnosis and treatment of disease. In particular, the presently-disclosed subject matter includes compositions that include edible plant-derived microvesicles having a targeting cell-derived plasma membrane coating and that are useful in the treatment of disease.

In some embodiments of the presently-disclosed subject matter, a composition is provided that comprises a microvesicle derived from an edible plant, where the microvesicle is, in turn, coated with a plasma membrane derived from a targeting cell. In some embodiments, the edible plant is a fruit or a vegetable, such as, in some embodiments, a grape, a grapefruit, or a tomato. In some embodiments, the targeting cell used to derive the plasma membrane coating the microvesicle is an activated leukocyte.

With further respect to the microvesicle compositions, in some embodiments, the microvesicle encapsulates a therapeutic agent. In some embodiments, the therapeutic agent is selected from a phytochemical agent and a chemotherapeutic agent. In some embodiments, the phytochemical agent is selected from curcumin, resveratrol, baicalein, equol, fisetin, and quercetin. In some embodiments, the chemotherapeutic agent is selected from the group consisting of retinoic acid, 5-fluorouracil, vincristine, actinomycin D, adriamycin, cisplatin, docetaxel, doxorubicin, and taxol. In other embodiments, the therapeutic agent comprises a nucleic acid molecule, such as, in some embodiments, an siRNA, a microRNA, or a mammalian expression vector. In some embodiments, pharmaceutical compositions are further provided where the microvesicle compositions are combined with a pharmaceutically-acceptable vehicle, carrier, or excipient.

Further provided, in some embodiments of the presently-disclosed subject matter, are methods for treating an inflammatory disorder. In some embodiments, a method for treating an inflammatory disorder is provided that comprises the step of administering to a subject in need thereof an effective amount of a microvesicle composition described herein. In some embodiments, the inflammatory disorder is selected from the group consisting of sepsis, septic shock, colitis, colon cancer, and arthritis. For administration of the compositions, in some embodiments, the composition is administered orally or intranasally. In some embodiments, subsequent to administration, the composition reduces an amount of an inflammatory cytokine in a subject, such as, in certain embodiments, tumor necrosis factor-α, interleukin-1β, interferon γ, and interleukin-6.

Still further provided, in some embodiments of the presently-disclosed subject matter, are methods for treating a cancer. In some embodiments, a method for treating a cancer in a subject in a subject is provided that comprises administering to a subject an effective amount of a microvesicle composition described herein. In some embodiments of the methods for treating a cancer, the therapeutic agent is selected from a phytochemical agent and a chemotherapeutic agent. In some embodiments, the cancer is selected from a brain cancer, a breast cancer, a lung cancer, and a colon cancer.

Further features and advantages of the present invention will become evident to those of ordinary skill in the art after a study of the description, figures, and non-limiting examples in this document.

BRIEF DESCRIPTION OF THE DRAWINGS

FIG. 1A is a schematic diagram showing the preparation process of the IGNVs and drug loaded-GNV microvesicles for targeted delivery of therapeutic agents to inflammatory sites. FIG. 1B is a graph showing the size distribution and surface Zeta potential of free GNVs and EL4 cells plasma membrane coated GNVs (IGNVs) were measured using a ZetaSizer. FIG. 1C includes images showing free GNVs (left) and IGNVs (right) that were visualized and imaged by scanning electron microscopy. FIG. 1D includes images showing the co-localization of the EL4 cell derived plasma membranes and GNV cores, where, for assembling IGNVs, the EL4 cell derived plasma membranes were labeled with PKH67 green dye and GNV cores were labeled with PKH26 red dye, where 4T1 cells were cultured in the presence of GNVs (upper panel) or IGNVs (bottom panel) for 12 h, and where representative images of cells were then taken using a confocal microscope at a magnification of ×400.

FIG. 2A includes images and graphs showing the results of a transwell assay for detecting chemotaxis of ETA cell plasma membrane coated GNVs, where HUVEC cells were cultured in the upper chamber and 4TO7 cells were cultured in the lower chamber of a transwell plate, where transmigration of the PKH26 labeled GNVs or IGNVs were imaged after 24 h and 48 h in culture using a confocal microscope, and where the intensity of the fluorescent signal of media in the lower chamber (n=3) was measured and expressed as the percent of transwell efficiency of fluorescent intensity of PKH26 labeled GNVs or IGNVs. FIGS. 2B-2E are images and graphs showing the distribution of DiR dye labeled IGNVs in: LPS induced skin acute inflammatory mouse model (FIG. 2B); DSS induced colitis mice (FIG. 2C); CT26 tumor model (FIG. 2D); and 4T1 tumor model (FIG. 2E); where live-mouse images (left) were collected 6 h and 24 h after I.V. injection of DiR dye labeled IGNVs, where skin, colon, and tumor tissues were removed 24 h after the injection and scanned for DiR dye signals, and where a representative image from each group of mice is shown (left panels) and followed by graphical figures (right panels) presented as the mean net intensity (Sum Intensity/Area, n=5) ($p<0.01$ and *$p<0.001$).

FIG. 3A includes images showing chemokine expression in normal skin (Normal), LPS induced acute inflammatory skin tissues (Skin-LPS), CT26 (CT26 tumor) and 4T1 (4T1 tumor) tissues, where the expressions were determined using a Proteome Profiler from R&D systems, and where each dot represents a chemokine detected by a capture antibody and printed in duplicate on a membrane. FIG. 3B includes graphs showing the expression of chemokine receptors on IGNVs, where the IGNVs were analyzed by FACS analysis of IGNVs coated on 4 μn-diameter aldehyde/sulfate latex beads. FIG. 3C is a graph showing in vitro transmigration of IGNVs, where HUVEC cells (n=3) were cultured in the fibronectin coated-upper chamber as a transmigration barrier, where PKH26 labeled IGNVs (PKH26-IGNVs) were pre-incubated with recombinant chemokines as listed in FIG. 1C or with the extract from 4T1 tumor, where, after washing, pre-incubated PKH26-IGNVs were added to the upper chamber, and cultured in the presence of recombinant chemokines (CXCL1/2/9/10 plus CCL2/5) in the lower chamber, and where, after a 24 h incubation, the intensity of PKH26 fluorescence of media in the lower chamber (n=3) was measured and expressed as the % of transwell efficiency of PKH 26+ IGNVs. FIG. 3D includes images and a graph showing IGNVs in LPS-induced acute skin inflammatory mice, where DiR dye labeled IGNVs were pre-incubated overnight at 4° C. with (neutralized) or without (not neutralized) 4T1 extract before an I.V. injection, and where a representative image at 6 h and 24 h after the injection from each group of mice (n=5) is shown (left) and followed by graphical figures (right) presented as the mean net intensity (Sum Intensity/Area, n=5). FIG. 3E includes images showing immunohistochemical staining of chemokines (CCL2, CCL5, CXCL9 and CXCL10) expressed in human breast cancer, colon cancer tissues (bottom panels) and paired adjacent tissues (upper panels), where a representative image (n=20 for colon cancer, n=21 for breast cancer) from each sample is shown. FIGS. 3F-3G are graphs showing the results of experiments where DiR dye labeled IGNVs were pre-incubated at 4° C. overnight with recombinant chemokines as listed in the figures and then I.V. injected into LPS-induced acute skin inflammatory mice (FIG. 3F) or CT26 tumor-bearing mice (FIG. 3G), where DiR dye signals in skin and tumor tissues were determined 24 h after the injection. FIG. 3H is a graph showing transmigration of IGNVs with/without LFA-1 neutralization, where PKH26 labeled IGNVs were pre-incubated overnight with anti-LFA-1 antibody at 4° C. and then added into the apical chamber, and where the intensity of PKH26 fluorescence of the media in the lower chamber was measured after 24 and 48 h of incubation and expressed as the % of transwell efficiency of PKH26$^+$IGNVs. FIG. 3I includes an image and a graph showing the results of an experiment where DiR dye labeled IGNVs were pre-incubated with functional anti-LFA-1 antibody at 4° C. overnight, washed, I.V. injected into LPS-induced acute skin inflammatory mice, and the DiR signals was detected after 24 h injection.

FIGS. 4A-4B include graphs showing the profiles of hIGNV (FIG. 4A) and mIGNV (FIG. 4B) chemokine receptors based on FACS analysis, where representative histograms (n=5) show the percentage of staining of chemokine receptors from the hIGNVs and inIGNVs, and where three different bands from sucrose gradients of plasma membrane from LPS stimulated leukocytes were used for coating GNVs: top band (LPS-T), middle band (LPS-M), and bottom band (LPS-B). FIG. 4C includes images and graphs showing trafficking of DiR dye labeled hIGNVs in human colon cancer SW620-bearing mice, where mice were I.V. injected with DiR dye labeled hIGNVs, where live imaging of whole mice was carried out on day 1 and 5 after the injection, where, at day 5 after the injection, tumors were removed and scanned, and where trafficking of DiR dye labeled-mIGNVs in LPS-induced an acute skin inflammatory mouse model were measured. FIGS. 4D-4E includes images and a graph showing the results of an experiment where mice were I.V. injected with DiR dye labeled mIGNVs without (FIG. 4D) or with (FIG. 4E) CXCR2 knockout, where skin was removed 72 h (FIG. 4D) or 24 h (FIG. 4E) after the injection and scanned. A representative image (FIGS. 4C-4D) from each group of mice is shown and graphical figures are presented as the mean net intensity (Sum Intensity/Area, n=5). $*p<0.05$, $p<0.01$ and $*p<0.001$.

FIG. 5A is a graph showing stability of circulating IGNVs. FIG. 5B includes images showing in vitro release profile of doxorubicin from IGNV-DOX in PBS buffer with different pH values (5.0, 5.5, 6.0, 6.5 and 7.2, n=5, $**p<0.01$) FIG. SC is a graph showing biodistribution of doxorubicin in 4T1 tumor-hearing mice, where 4T1 tumor-bearing mice n=5) were I.V. injected with IGNV-DOX or DOX-NP™, and where the doxorubicin in 4T1 tumor tissues, livers, lungs, spleens, kidneys, hearts and thymus was measured ($*p<0.05$). FIG. 5D includes images showing biodistribution of doxorubicin in CT26 and 4T1 tumor tissues, where free doxorubicin (Free DOX), GNVs delivered doxonihicin (GNV-DOX) and IGNVs delivered doxonihicin (IGNV-DOX) were I.V. injected into CT26 (n=5) and 4T1 tumor-bearing mice=5), where tumor tissues were removed, fixed and sectioned, and where doxorubicin in tumor tissues was observed using a confocal imaging system. FIGS. 5E-5F includes images and graphs showing the results of experiments where CT26 and 4T1 cells were injected subcutaneously (CT26) or in a mammary fat pad (4T1) of BALB/c mice, where mice were I.V. injected with IGNV-DOX or controls as listed in the figure every 3 days for 30 days from 7 days after tumor cells were injected, where representative images of tumors (FIG. 5E, left panel) from each group (n=5) are shown, tumor volume was measured every 5 days, (FIG. 5E, right panel), and where the survival rate (FIG. 5F) of mice was calculated ($*p<0.05$, and $**p<0.01$).

FIG. 6A includes images showing the morphology of cultured EL4 cells without (left) or with (right) PMA stimulation, original magnification ×10. FIG. 6B includes graphs showing the percentages of chemokine receptors expressed on EL4 cells with/without PMA stimulation, where EL4 cells (n=3) were harvested at 24 h after PMA stimulation and stained with fluorescence labeled anti-CCR3, CCR4, CCR5, CCR7, CCR9, CXCR3 and CXCR7 antibodies and the percentage of chemokine receptors were analyzed by FACS.

FIG. 15A is a graph showing the results of an experiment where the proliferation of IGNV treated-4T1 cells was analyzed using the ATPlite assay 24 h after exposure to different concentration of IGNVs. FIG. 15B is a graph showing the results of an experiment where numbers of living 4T1 cells treated with IGNVs at passage number 1 through 5 were determined by counting the number of living cells (unstained with trypan blue). FIG. 15C-15D include graphs showing the results of an experiment where serum TNF-$\alpha$, IL-6 and IL-1$\beta$ (FIG. 15C) and ALT, AST (FIG. 15D) were analyzed 24 h after mice were I.V. injected with IGNVs three times or PBS as a control (normal control). FIG. 15E includes images of H&E-stained sections of livers, spleens, kidneys and lungs from IGNV-injected mice, original magnification ×20. FIG. 15F includes graphs showing the liver, lung, spleen, kidney, and heart weights of injected animals.

FIG. 16A is an image showing purification of therapeutic drugs (left: doxorubicin, right: curcumin) loaded into IGNVs by discontinuous sucrose density gradient centrifugation. FIGS. 16B-16C are graphs showing size distribution (FIG. 16B) and Zeta potential (FIG. 16C) of IGNV-DOX and IGNV-Cur analyzed using a ZetaSizer. FIG. 16D is a graph showing the loading efficiency of doxorubicin and curcumin detected by UV spectrometry and expressed as %=(Total drugs-free drugs)/Total drugs×100%. FIG. 16E includes graphs showing the release profile of doxorubicin and curcumin in PBS buffer at pH 7.2 and 37° C. as detected by UV spectrometry at 497 and 426 nm, respectively.

FIG. 17A is a graph showing the profile of doxorubicin released from DOX-NP™ at 37° C. in PBS buffer at different pH values (5.0, 5.5, 6.0, 6.5 and 7.2). FIG. 17B is a graph showing the proliferation of 4T1 cells treated with different concentrations of control liposomes and analyzed using the ATPlite assay. FIGS. 17C-17D are graphs showing the results of an experiment where mice were I.V. injected with control liposomes daily for 3 days, where 24 h after the last injection of control liposomes, serum TNF-$\alpha$, IL-6 and IL-1$\beta$ (FIG. 17C) and the liver enzymes AST and ALT (FIG. 17D) were assessed (n=5 mice per group).

DESCRIPTION OF EXEMPLARY EMBODIMENTS

Figure 1A:
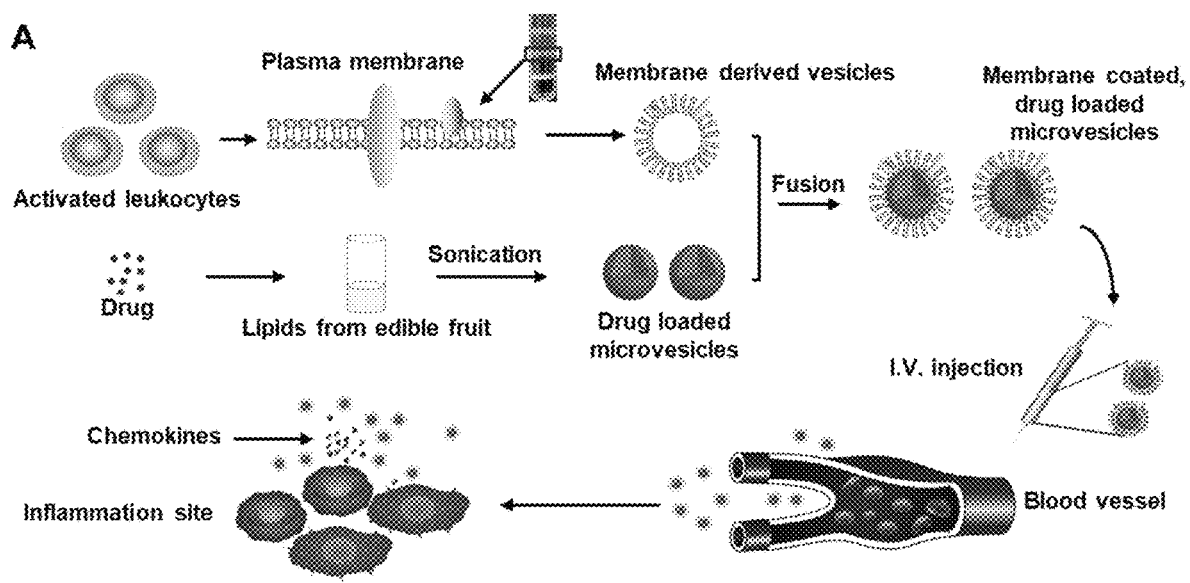
FIGS. 1A-1D include schematic diagrams, graphs, and images showing the characterization of inflammatory cell plasma membrane-coated grapefruit-derived nanovectors GNVs (IGNVs).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is based, at least in part, on the discovery that the binding and coating of inflammatory cell-derived membranes on grapefruit-derived microvesicles or nanovectors (GNVs) is an effective and efficient strategy to take advantage of the unlimited availability of GNVs and to generate personalized delivery vectors that would target inflammatory sites in diseases (FIG. 1A). As described herein below, such compositions have, among others, two advantages, namely: 1) the plasma membrane from activated leukocytes is preferentially bound on the microvesicles made of fruit nanoparticles lipids; and 2) the resultant microvesicles are safe and can be successfully used for targeted delivery of therapeutic agents to inflammatory sites.

Microvesicles are naturally existing nanoparticles that are in the form of small assemblies of lipid particles, are about 50 to 1000 nm in size, and are not only secreted by many types of in vitro cell cultures and in vivo cells, but are commonly found in vivo in body fluids, such as blood, urine and malignant ascites. Indeed, microvesicles include, but are not limited to, particles such as exosomes, epididimosomes, argosomes, exosonie-like vesicles, microparticles, promininosomes, prostasomes, dexosomes, texosomes, dex, tex, archeosomes, and oncosomes.

As noted above, microvesicles can be formed by a variety of processes, including the release of apoptotic bodies, the budding of microvesicles directly from the cytoplasmic membrane of a cell, and exocytosis from multivesicular bodies. For example, exosomes are commonly formed by their secretion from the endosomal membrane compartments of cells as a consequence of the fusion of multivesicular bodies with the plasma membrane. The multivesicular bodies are formed by inward budding from the endosomal membrane and subsequent pinching off of small vesicles into the luminal space. The internal vesicles present in the MVBs are then released into the extracellular fluid as so-called exosomes.

As part of the formation and release of microvesicles, unwanted molecules are eliminated from cells. However, cytosolic and plasma membrane proteins are also incorporated during these processes into the microvesicles, resulting in microvesicles having particle size properties, lipid bilayer functional properties, and other unique functional properties that allow the microvesicles to potentially function as effective nanoparticle carriers of therapeutic agents. In this regard, the term "microvesicle" is used interchangeably herein with the terms "nanoparticle," "liposome," "exosome," "exosome-like particle," "nano-vector" and grammatical variations of each of the foregoing. It has now been discovered though that edible plants, such as fruits, are not only a viable source of large quantities of microvesicles, but that microvesicles derived from edible plants can be coated with plasma membranes derived from targeting cells, such as leukocytes, and used as an effective delivery vehicle for homing or otherwise targeting the microvesicles, including any therapeutic agents that may be included within the microvesicles, to the sites of inflammation and disease.

The presently-disclosed subject matter thus includes edible plant-derived microvesicle compositions that are coated with plasma membranes derived from targeting cells. The term "targeting cells," and grammatical variations thereof, is used herein to refer to those cells that, by virtue of the inclusion of certain targeting moieties (e.g., receptors or other proteins) in their plasma membranes, preferentially home or are trafficked to certain tissues and organs in the body of a subject. For example, in some embodiments, the targeting cells are activated inflammatory cells, such as leukocytes, or macrophages or neutrophils that preferentially target or home to sites of inflammation. As another example, in some embodiments, the targeting cells are circulating tumor cells or metastatic tumor cells that preferentially home to tissues such as brain, lung, liver, and bone tissue (i.e., frequent sites of metastasis). As yet another example, in some embodiments, the targeting cells are stem cells (e.g., bone marrow derived stem cells) that can be preferentially targeted to and used for tissue regeneration.

In some embodiments, the microvesicle compositions further include therapeutic agents and are useful in the treatment of various diseases, including inflammatory disorders and cancers. In some embodiments of the presently-disclosed subject matter, a microvesicle composition is provided that comprises a microvesicle derived from an edible plant and a plasma membrane coating on the microvesicle, where the plasma membrane has been derived from a targeting cell. In some embodiments, a composition is provided wherein a therapeutic agent is encapsulated by the microvesicle derived from the edible plant. In some embodiments, the therapeutic agent encapsulated by the edible-plant derived microvesicle is selected from a phytochemical agent and a chemotherapeutic agent.

The term "edible plant" is used herein to describe organisms from the kingdom Plantae that are capable of producing their own food, at least in part, from inorganic matter through photosynthesis, and that are fit for consumption by a subject, as defined herein below. Such edible plants include, but are not limited to, vegetables, fruits, nuts, and the like. In some embodiments of the microvesicle compositions described herein, the edible plant is a fruit. In some embodiments, the fruit is selected from a grape, a grapefruit, and a tomato.

The phrase "derived from an edible plant," when used in the context of a microvesicle derived from an edible plant, refers to a microvesicle that, by the hand of man, exists apart from its native environment and is therefore not a product of nature. In this regard, in some embodiments, the phrase "derived from an edible plant" can be used interchangeably with the phrase "isolated from an edible plant" to describe a microvesicle of the presently-disclosed subject matter that is useful for being coated with an inflammatory cell-derived plasma membrane and/or for encapsulating therapeutic agents.

The phrase "encapsulated by a microvesicle," or grammatical variations thereof is used herein to refer to microvesicles whose lipid bilayer surrounds a therapeutic agent. For example, a reference to "microvesicle curcumin" refers to an microvesicle whose lipid bilayer encapsulates or surrounds an effective amount of curcumin. In some embodiments, the encapsulation of various therapeutic agents within microvesicles can be achieved by first mixing the one or more of the phytochemical agents or chemotherapeutic agents with isolated microvesicles in a suitable buffered solution, such as phosphate-buffered saline (PBS). After a period of incubation sufficient to allow the therapeutic agent to become encapsulated during the incubation period, the microvesicle/therapeutic agent mixture is then subjected to a sucrose gradient (e.g., and 8, 30, 45, and 60% sucrose gradient) to separate the free therapeutic agent and free microvesicles from the therapeutic agents encapsulated within the microvesicles, and a centrifugation step to isolate the microvesicles encapsulating the therapeutic agents. After this centrifugation step, the microvesicles including the therapeutic agents are seen as a band in the sucrose gradient such that they can then be collected, washed, and dissolved in a suitable solution for use as described herein below.

As noted, in some embodiments, the therapeutic agent is a phytochemical agent. As used herein, the term "phytochemical agent" refers to a non-nutritive plant-derived compound, or an analog thereof. Examples of phytochemical agents include, but are not limited to compounds such as monophenols; flavonoids, such as flavonols, flavariones, flavones, flavan-3-ols, anthocyanins, anthocyanidins, isoflavones, dihydroflavonols, chalcones, and coumestans; phenolic acids; hydroxycinnamic acids; lignans; tyrosol esters; stillbenoids; hydrolysable tannins; carotenoids, such as carotenes and xanthophylls; monoterpenes; saponins; lipids, such as phytosterols, tocopherols, and omega 3,6,9 fatty acids; diterpenes; triterpinoids; betalains, such as betacyanins and betaxanthins; dithiolthiones; thiosulphonates; indoles; and glucosinolates. As another example of a phytochemical agent disclosed herein, the phytochemical agent can be an analog of a plant-derived compound, such as oltipraz, which is an analog of 1,2-dithiol-3-thione, a compound that is found in many coniferous vegetables.

In some embodiments of the presently-disclosed subject matter, the therapeutic agent is a phytochemical agent selected from curcumin, resveratrol, baicalein, fisetin, and quercetin. In some embodiments, the phytochemical agent is curcumin. Curcumin is a pleiotropic natural polyphenol with anti-inflammatory, anti-neoplastic, anti-oxidant and chemopreventive activity, with these activities having been identified at both the protein and molecular levels. Nevertheless, limited progress has been reported with respect to the therapeutic use of curcumin as curcumin is insoluble in aqueous solvents and is relatively unstable. In addition, curcumin is known to have a low systemic bioavailability after oral dosing, which further limits its usage and clinical efficacy. It has been determined, however, that by encapsulating curcumin in edible plant derived microvesicles, not only can the solubility of curcumin be increased, but the encapsulation of the curcumin within the microvesicles protects the curcumin from degradation and also increases the bioavailability of the microvesicle curcumin.

As also noted herein above, in some embodiments of the presently-disclosed subject matter, the therapeutic agent that is encapsulated within the exosome is a chemotherapeutic agent. Examples of chemotherapeutic agents that can be used in accordance with the presently-disclosed subject matter include, but are not limited to, platinum coordination compounds such as cisplatin, carboplatin or oxalypiatin; taxane compounds, such as paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE® (Millennium Pharmaceuticals, Cambridge, Ma.); or YONDELIS® (Johnson & Johnson, New Brunswick, NJ). In some embodiments, the chemotherapeutic agent that is encapsulated by an exosome in accordance with the presently-disclosed subject matter is selected from retinoic acid, 5-fluorouracil, vincristine, actinomycin D, adriamycin, cisplatin, docetaxel, doxorubicin, and taxol.

In other embodiments of the presently-disclosed subject matter, therapeutic agents included within the microvesicle compositions comprises nucleic acid molecules selected from a siRNA, a microRNA, and an expression vector, such as a mammalian expression vector. The term "nucleic acid" refers to deoxyribonucleotides or ribonucleotides and polymers thereof in either single- or dotible-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) Nucleic Acid Res 19:5081; Ohtsuka et al. (1985) J Biol Chem 260:2605-2608; Rossolini et al. (1994) Mol Cell Probes 8:91-98). The terms "nucleic acid" or "nucleic acid sequence" can also be used interchangeably with gene, open reading frame (ORF), cDNA, mRNA, siRNA, microRNA, and the like.

The terms "small interfering RNA," "short interfering RNA," "small hairpin RNA," "siRNA," and "shRNA" are used interchangeably herein to refer to any nucleic acid molecule capable of mediating RNA interference (RNAi) or gene silencing. See, e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. la one embodiment, the siRNA can comprise a double stranded polynucleotide molecule comprising complementary sense and antisense regions, wherein the antisense region comprises a sequence complementary to a region of a target nucleic acid molecule. In another embodiment, the siRNA can comprise a single stranded polynucleotide having self-complementary sense and antisense regions, wherein the antisense region comprises a sequence complementary to a region of a target nucleic acid molecule. In yet another embodiment, the siRNA can comprise a single stranded polynucleotide having one or more loop structures and a stem comprising self-complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

MicroRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression. There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

In some embodiments, the nucleic acid molecules that are encapsulated or otherwise incorporated into a microvesicle composition of the presently-disclosed subject matter are included in the microvesicles are part of an expression vector. The term "expression vector" is used interchangeably herein with the terms "expression cassette" and "expression control sequence," and is used to refer to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction, or a non-coding RNA (ncRNA) such as a small or long m-RNA. The expression vector comprising the nucleotide sequence of interest can be chimeric, meaning that at least one of its components is heterologous with respect to at least one of its other components. The expression vector can also be one that is naturally occurring but has been obtained in a recombinant form useful for heterologous expression. In some embodiments, the expression vector is a mammalian expression vector that is capable of directing expression of a particular nucleic acid sequence of interest in a mammalian cell.

With respect to the plasma membrane coating the edible-plant derived microvesicles, the phrase "coating the microvesicle" and variations thereof, is used herein to refer to the covering, placement, and/or attachment of a plasma membrane to the lipid bilayer of an exemplary microvesicle of the presently-disclosed subject matter, or a portion thereof. In some embodiments, the covering of a microvesicle with a plasma membrane derived from an activated inflammatory cell, such as a leukocyte, is achieved by initially exposing a population of inflammatory cells to a cell activation compound (e.g., Phorbol 12-Myristate 13-Acetate (PMA), a calcium ionophore such as Ionomycin, or a protein transport inhibitor) capable of inducing the expression of various cytokines, chemokines, and/or chemokine receptors. After a period of incubating the inflammatory cells with such an activation compound, the inflammatory cells are then lysed and homogenized, and the plasma membranes are collected by sucrose gradient density centrifugation. After collecting the plasma membranes, the membranes are subsequently sonicated to form vesicles. Such vesicles can then be combined with the microvesicles described herein (e.g., microvesicles encapsulating a therapeutic agent) and co-extruded through a membrane to thereby coat the microvesicles with the plasma membranes derived from the inflammatory cells. In this regard, and without wishing to be bound by any particular, theory, it is believed that by virtue of using plasma membranes derived from activated inflammatory cells, the resulting microvesicle compositions include a plasma membrane coating having one or more chemokine receptor or other targeting moieties that are capable of homing or otherwise targeting the compositions to the site of inflamed or diseased tissue.

In some embodiments of the presently disclosed subject matter, a pharmaceutical composition is provided that comprises an edible plant-derived microvesicle composition disclosed herein and a pharmaceutical vehicle, carrier, or excipient. In some embodiments, the pharmaceutical composition is pharmaceutically-acceptable in humans. Also, as described further below, in some embodiments, the pharmaceutical composition can be formulated as a therapeutic composition for delivery to a subject.

A pharmaceutical composition as described herein preferably comprises a composition that includes pharmaceutical carrier such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); acid preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of capsules, tablets or lozenges formulated in conventional manner. Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the microvesicle compositions of the presently-disclosed subject matter can also be formulated as rectal compositions, such as suppositories or retention enemas, e.g., containing conventional suppository bases such as cocoa butter or other glycerides. Further, the exosomal compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

Further provided, in some embodiments of the presently-disclosed subject matter, are methods for treating an inflammatory disorder or a cancer. In some embodiments, a method for treating an inflammatory disorder is provided that comprises administering to a subject in need thereof an effective amount of a microvesicle composition of the presently-disclosed subject matter.

As used herein, the terms "treatment" or "treating" relate to any treatment of a condition of interest (e.g., an inflammatory disorder or a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain anal/ or loss of function in the affected tissue or organ. The cause of inflammation can be due to physical damage, chemical substances, micro-organisms, tissue necrosis, cancer, or other agents or conditions.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to atherosclerosis; arthritis; inflammation-promoted cancers; asthma; autoimmune uveitis; adoptive immune response; dermatitis; multiple sclerosis; diabetic complications; osteoporosis; Alzheimer's disease; cerebral malaria; hemorrhagic fever; autoimmune disorders; and inflammatory bowel disease. In some embodiments, the inflammatory disorder is selected from the group consisting of sepsis, septic shock, colitis, colon cancer, and arthritis.

For administration of a therapeutic composition as disclosed herein (e.g., an edible plant-derived microvesicle encapsulating a therapeutic agent), conventional methods of extrapolating human dosage based on doses administered to a murine animal model can be carried out using the conversion factor for converting the mouse dosage to human dosage: Dose 1-Ionian per kg=Dose Mouse per kg×12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082).

Regardless of the route of administration, the compositions of the presently-disclosed subject matter are typically administered in amount effective to achieve the desired response. As such, the term "effective amount" is used herein to refer to an amount of the therapeutic composition (e.g., a microvesicle encapsulating a therapeutic agent, and a pharmaceutically vehicle, carrier, or excipient) sufficient to produce a measurable biological response (e.g., a decrease in inflammation). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-FEU Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Pa.; Duch et al., (1998) Toxicol. Lett. 100-101:255-263.

In some embodiments of the therapeutic methods disclosed herein, administering an edible plant-derived microvesicle composition of the presently-disclosed subject matter reduces an amount of an inflammatory cytokine in a subject. In some embodiments, the inflammatory cytokine can be interleukin-1β (IL-1β), tumor necrosis factor-alpha (TNF-α), interferon-γ (IFN-γ), or interleukin-6 (IL-6).

Various methods known to those skilled in the art can be used to determine a reduction in the amount of inflammatory cytokines in a subject. For example, in certain embodiments, the amounts of expression of an inflammatory cytokine in a subject can be determined by probing for mRNA of the gene encoding the inflammatory cytokine in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, CA). Because the probes to which the nucleic acid molecules of the sample are bound are known, the molecules in the sample can be identified. In this regard, DNA probes for one or more of the mRNAs encoded by the inflammatory genes can be immobilized on a substrate and provided for use in practicing a method in accordance with the presently-disclosed subject matter.

With further regard to determining levels of inflammatory cytokines in samples, mass spectrometry and/or immunoassay devices and methods can also be used to measure the inflammatory cytokines in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the inflammatory molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the inflammatory molecules is also contemplated by the present invention. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadropole mass spectrometers. Methods for utilizing MS analysis to detect the presence and quantity of peptides, such as inflammatory cytokines, in biological samples are known in the art. See, e.g., U.S. Pat. Nos. 6,925,389; 6,989,100; and 6,890,763 for further guidance, each of which are incorporated herein by this reference.

With still further regard to the various therapeutic methods described herein, although certain embodiments of the methods disclosed herein only call for a qualitative assessment (e.g., the presence or absence of the expression of an inflammatory cytokine in a subject), other embodiments of the methods call for a quantitative assessment (e.g., an amount of increase in the level of an inflammatory cytokine in a subject). Such quantitative assessments can be made, for example, using one of the above mentioned methods, as will be understood by those skilled in the art.

The skilled artisan will also understand that measuring a reduction in the amount of a certain feature (e.g., cytokine levels) or an improvement in a certain feature (e.g., inflammation) in a subject is a statistical analysis. For example, a reduction in an amount of inflammatory cytokines in a subject can be compared to control level of inflammatory cytokines, and an amount of inflammatory cytokines of less than or equal to the control level can be indicative of a reduction in the amount of inflammatory cytokines, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Still further provided, in some embodiments, are methods for treating a cancer. In some embodiments, a method for treating a cancer is provided that comprises administering to a subject in need thereof an effective amount of an edible-plant derived microvesicle composition of the presently-disclosed subject matter (i.e., where a plasma membrane-coated microvesicle encapsulates a therapeutic agent). In some embodiments, the therapeutic agent encapsulated within the plasma membrane-coated microvesicle and used to treat the cancer is selected from a phytochemical agent and a chemotherapeutic agent, as such agents have been found to be particularly useful in the treatment of cancer. As used herein, the term "cancer" refers to all types of cancer or neoplasm or malignant tumors found in animals, including leukemias, carcinomas, melanoma, and sarcomas.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukernic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurtle cell carcinoma, hyaline carcinoma, hvpemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosuni.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, 'Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanonia, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from the group consisting of skin cancer, head and neck cancer, colon cancer, breast cancer, brain cancer, and lung cancer.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include, but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. flames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Inflammation is a hallmark of numerous diseases. Activated immune cells are intrinsically capable of homing to inflammatory sites. Using three inflammatory driven disease mouse models, the following studies demonstrated that grapefruit-derived nanovectors (GNVs) coated with inflammatory chemokine receptor enriched membranes of activated leukocytes (IGNVs) are enhanced for homing to inflammatory tissues. Blocking CXCR1 and CXCR2 on the IGNVs significantly inhibited IGNVs homing to the inflammatory tissue. The therapeutic potential of IGNVs was further demonstrated by enhancing the chemotherapeutic effect as shown by inhibition of tumor growth in two tumor models and inhibiting the inflammatory effects of DSS induced mouse colitis. The fact that IGNVs are capable of homing to inflammatory tissue and that there is an overexpression of chemokines in diseased human tissue provides support for using IGNVs for the more directed delivery of therapeutic agents to inflammatory sites and the use of IGNVs as personalized medicine for treatment of inflammatory related diseases.

Materials and Methods

Mice. C57BL/6j mice, BALB/c mice, and C.129S2(B6)-Cxcr2$^{tm1Mwm}$/J mice 6-8 weeks of age were obtained from Jackson Laboratories. All animal procedures were approved by the University of Louisville Institutional Animal Care and Use Committee.

Cell culture. The mouse T lymphoma EL4 cells, mouse 4T1, 4TO7 breast cancer cell lines, mouse NMuMG mammary gland epithelial cells, CT26 colon cancer and human umbilical vein endothelial cells (HUVECs) were purchased from ATCC. CT26 cells were cultured in RPMI 1640 media; EL4, 4T1 and 4TO7 cells were maintained in DMEM media supplemented with 10% heat-inactivated FBS. HUVECs were cultured in complete endothelial cell growth medium (ECGM; Promocell #C-22010). NMuMG cells were cultured in complete DMEM media supplemented with 10 µg/ml insulin. All cells were maintained in a humidified CO2 incubator at 37° C.

Reagents and antibodies. Doxorubicin, curcumin, phorbol 12-myristate 13-acetate (PMA), lipopolysaccharide (LPS, *Escherichia coli* 0111:B4), PKH67, PKH26, and Fluorescent Cell Linker kits were purchased from Sigma-Aldrich (St Louis, MO, USA). Commercial DOX-NP™ (300102S) and its control liposomes were purchased from Avanti Polar Lipids Inc. (Alabaster, Alabama, USA). Proteinase inhibitor cocktail tablets were obtained from Roche Diagnostics GmbH (Mannheim, Germany). DiR dye was obtained from Life Technologies (N.Y., USA). Dextran sodium sulfate (DSS, MW: 36,000-50,000) was obtained from MP Biomedicals, LLC (Santa Ana, CA). Infinity™ ALT (GPT) and AST (GOT) liquid stable reagents were purchased from Thermo Scientific (Pittsburgh, PA, USA). The Luminescence ATP detection system was obtained from PerkinEliner (Waltham, Ma., USA). Recombinant mouse chemokines CXCL1, CXCL2, CXCL9, CXCL10, CXCL11, CCL2, and CCL5 were purchased from Biolegend (San Diego, CA, USA). Fluorescent conjugated antibodies against mouse or human CCR3, CCR4, COR5, CCR7, CCR9, CXCR2, CXCR3, CXCR7, antibodies against mouse CD3, F4/80, CD11b, CD11c, CD19, Ly6G and Gr1 were purchased from eBioscience (San Diego, CA, USA). Anti-human CXCL1, CXCL10, CCL2 and CCL5 antibodies were obtained from LifeSpan BioSciences, Inc. (Seattle, WA, USA). Anti-mouse CXCL1, CXCL10, CCL2 and CCL5 antibodies and CCL5, CXCL10 ELISA kits were purchased from Biolegend (San Diego, CA, USA). Alexa Fluor 488 nm and 647 nm conjugated secondary antibodies were obtained from Life Technologies (N.Y., USA). The Human CCL2 ELISA kit was purchased from eBioscience.

Plasma membrane isolation and purification. Plasma membranes were isolated and purified using a method as described previously. In brief, mouse lymphoma cell line EL4 cells were cultured with without PMA stimulation (100 ng/ml) for 12 h. Cells ($2 \times 10^8$) were then collected and centrifuged at 500×g for 10 min at 4° C. The cell pellets were resuspended in 1 ml of homogenization buffer at a final concentration of 10 mM Tris HCL, 25 mM D-sucrose, 1 mM MgCl2, 1 mM KCI, 10 µg/ml RNase, 10 µg/ml DNase and 1× proteinase inhibitor cocktail. The cell suspension was homogenized on ice by 100 passes using a hand-held Dounce homogenizer. The supernatant was collected after centrifugation at 500×g for 10 min. For further purification, collected supernatants were subjected to a discontinuous sucrose density gradient centrifugation at 28,000 g for 45 min at 4° C. on a 30%, 40% and 55% sucrose in a 0.9% saline solution. For plasma membrane isolation from leukocytes of mice or human peripheral blood, anticoagulant treated peripheral blood was collected and centrifuged at 3000×g for 10 min at 4° C. Leukocytes were collected and the red blood cells were lysed by incubation with ACK lysis buffer (NH4Cl8.024 g/L, KHCO3 1 g/L, EDTA-2Na 3.722 mg/L) for 5 min at 22° C. The procedure for lysis of red blood cells was repeated once. The leukocytes were then cultured in RPMI 1640 with LPS (100 ng/ml) for 12 h before the plasma membranes from leukocytes of mice or human with/without LPS stimulation were isolated and purified using a discontinuous sucrose density gradient centrifugation method as described above.

Preparation of plasma membrane-derived vesicles. The plasma membranes purified from EL4 cells and mice or human peripheral blood leucocytes were sonicated in a glass vial with 200 µl ddH2O for 10 min using a FS30D bath sonicator (Fisher Scientific). The resulting vesicles were subsequently extruded through 100 nm polycarbonate porous membranes using an Avanti mini extruder (Avanti Polar Lipids).

Preparation of plasma membrane-coated GNVs. Grapefruit lipid derived nanoparticles (GNVs) were prepared according to the protocol as described previously. To prepare the plasma membrane coated GNVs, 400 nmol of GNVs were mixed with plasma membrane-derived vesicles (from approximately $5 \times 10^5$ cells) and extruded 20 times through a 200 nm polycarbonate porous membrane using an Avanti mini extruder. The GNVs coated with EL4 derived or mouse or human leukocyte-derived plasma membranes were then referred to as pseudo-inflammatory GNVs (IGNVs).

Phosphorus quantification. Phosphate in GNVs was quantified using a standard phosphorus solution (0.65 mM, P3869-25 ml from Sigma). First, different amounts of phosphate standard solutions (50, 25, 10, 5 and 0 nmol) were prepared in 100 µl ddH$_2$O, then 30 µl Mg(NO$_3$)$_2$ was added, and the mixture was heated by flame until dry. The dried sample was dissolved in 300 µl HCl and heated at 100° C. for 15 min, cooled, and centrifuged at 1000 rpm for 2 min. 700 µl of the reaction buffer (1 part of 10% ascobic acid and 6 parts 0.42% ammonium molybdate in 1 N H$_2$SO$_4$) were added and mixture incubated at 45° C. for 20 min. The absorption was read at OD$_{280}$.

Critical GNV miceller concentration (cmc). The critical micelle concentration (CMC) is approximately defined as the lipid monomer concentration at which appreciable amounts of micellar aggregates first begin to appear at equilibrium. Because GNVs are not monomers and are made from a number of lipids extracted from grapefruit nanoparticles, it was difficult to determine the CMC for each of grapefruit nanoparticle derived lipids that contribute to the formation of the GNVs. Therefore, unlike the common approach used for determination of CMC, an alternative approach was taken to determine the concentration of total GNV lipids above which GNVs form. In brief, total lipids extracted from grapefruit nanoparticles were determined using the phosphate assay as described above. Different volume of total lipids (0-100 μl, 200 uM in stock) in chloroform were pipetted into glass tubes, and the solvent was removed under a stream of nitrogen, and the lipid films were subsequently maintained under vacuum condition for 2 h. The dry lipid films were hydrated at 60° C. for 30 min in 20 mM HEPES buffer (pH 7.0). After a hath-sonication (FS60 bath sonicator, Fisher Scientific, Pittsburg, Pa) for 5 min, an equal volume of HEPES buffer (pH 7.0) was added and sonicated for another 5 min.

Size distribution and Zeta potential analysis. Size distribution and Zeta potential of particles were analyzed by a Zetasizer nano ZS (Malvern Instruments Ltd., Southborough, Ma.). To measure size, particle samples were diluted in PBS and dispersed by sonication for 5 seconds before measuring. To determine the Zeta potential of particles, GNVs or plasma membrane coated GNVs were washed in ddH2O by centrifugation at 100,000×g for 45 min at 4° C. The samples were resuspended in 1 ml ddH2O for measuring the Zeta potential of the particles.

FACS analysis of chemokine receptors, integrins on EL4 cells and IGNVs. To test the expression of chemokines receptors and integrins, collected EL4 cells were washed, and blocked with Fc blocker (2.4G2) at 4° C. for 15 min and then stained with PE labeled anti-CCR3, CCR4, CCR5, CCR7, CCR9, CXCR2, CXCR3, CXCR7, a4b7 and LFA-1 antibodies at 4° C. for 45 min. The chemokine receptors and LFA-1 on the KINVs were analyzed quantitatively using a FACS method as described previously. Briefly, GNVs or IGNVs were incubated with 4 mm-diameter aldehyde/sulfate latex beads in 400 ml PBS containing 2% FCS for 30 min and the mixtures were then washed and subsequently stained with PE labeled anti-CCR3, CCR4, CCR5, CCR7, CCR9, CXCR2, CXCR3, CXCR7 and LFA-1 antibodies at 4° C. for 45 min. Since no $\alpha 4\beta 7$ was detected on the EL4 cells; the levels of $\alpha 4\beta 7$ on the IGNVs was not analyzed. All samples were analyzed using an Accuri C6 flow cytometer.

Chemokine detection in skin and tumor tissues. Chemokines in normal skin tissue, LPS induced inflammatory skin, and CT26 and 4T1 tumor tissues were detected using Proteome Profiler™ antibody arrays (R&D System, Minneapolis, MN, USA) according to the manufacturer's protocol. Briefly, tissues were excised and homogenized in PBS with 1× protease inhibitors and a final concentration of 1% Triton X-100. The samples were frozen at −80° C. After thawing, the supernatant of samples was collected by centrifugation at 10,000×g for 5 min at 4° C. and the total protein was quantified using a NanoDrop 8000. After blocking for 1 h, the membranes were incubated with a mixture of reconstituted Cytokine Array Panel A Detection Antibody Cocktail and the supernatant overnight at 4° C. After washing three times, the membranes were incubated with streptavidin-HRP for 30 min at 22° C. Then, after washing three more times, the membranes were incubated with 1 ml of Chemi Regent Mix for 1-2 min at 22° C. before exposing to X-ray film for 1-5 min.

Imaging the plasma membrane coated GNVs (IGNVs). The purified IGNVs were prepared for electron microscopy using a conventional procedure and observed using an FEI Tecnai F20 electron microscope operated at 200 kV at a magnification of 38 000× and defocus of 2.5 μm. Fresh prepared GNVs were also fixed and imaged as a control. Photomicrographs were taken using a Gatan Ultrascan 4000 CCD camera.

To further confirm the co-localization of EL4 cell derived plasma membrane with GNVs, PKH67 labeled membrane-derived vesicles were mixed with PKH26 labeled GNVs and then extruded 15-20 times through a 200 nm polycarbonate porous membrane using an Avanti mini extruder. After washing at 100,000×g for 30 min, the particles were resuspended and incubated with 4T1 cells for 12 h in a 5% CO2 incubator. The cells were then washed 3 times with PBS, fixed with 2% PFA for 10 min at 22° C., and permeabilized with 0.2% Triton X-100 for 2 min at 22° C. After washing 3×, cells were stained with DAPI for 90 s. The co-localization of EL4 cell derived plasma membrane with GNVs was examined using a confocal microscope equipped with a digital image analysis system (Pixera, San Diego, CA, USA).

Fluorescence resonance energy transfer (FRET) analysis. The DiO/DPA system has been used for detection of cytoplasmic membrane potential changes using the principle of fluorescence resonance energy transfer (FRET). This approach was adapted in the present studies by pairing the common tracer dye DiO (as a fluorescent donor) with dipicrylamine (DPA), a low-molecular-weight lipophilic anion, as a non-fluorescent acceptor. As a donor, DiO is a bright, nontoxic membrane label that permits repeated imaging of fluorescent labeled GNVs. However, if DiO is in close proximity to the DPA dye labeled plasma membrane from activated T cells, which enables fluorescence quenching, the result is no fluorescent signal detected. To test whether IGNVs are coated with plasma membrane from activated T cells, DiO (5 mM) labeled GNVs and DPA (5 mM) labeled EL4 cell membrane derived-vesicles were prepared by sonication using a method as described previously. The extrusion of GNVs with EL4 derived membrane vesicles was carried out by extrusion for 20 times through a 200 rim polycarbonate porous membrane using an Avanti mini extruder. The mixture of DiO (5 mM) labeled GNVs and DPA (5 mM) labeled EL4 cells membrane derived-vesicles without extrusion was used as a control. Both samples were then diluted (1:5, 1:10, 1:20, 1:50, 1:100, and 1:150) with ddH$_2$O and the fluorescent intensity of DiO dye was measured by a fluorescent plate reader (Biotek HTS Multi-mode Readers). The non-quenched fluorescent signal, expressed as % of fluorescent intensity, was determined as follows: [(fluorescent intensity of diluted sample—fluorescent intensity of undiluted sample)/fluorescent intensity of diluted sample]× 100%. The results represent the mean of three independent experiments (error bars, standard errors of the means).

Transwell assay. HUVEC cells s ere seeded onto fibronectin-coated (7.5 mg/cm$^2$) Costar Transwell inserts (6.5 mm diameter and 5 mm pore size, Corning, Corning Incorporated, NY, USA) at a cell density of 5×10$^4$ cells/well. Chemokines were placed in the lower chamber. PKH26 labeled GNVs, IGNVs, chemokines or anti-LFA-1 antibody pre-incubated IGNVs were added into the upper chamber and incubated with HUVEC cells at 37° C. for 24 and 48 h. After incubation, the media from the lower chamber was collected and diluted. The fluorescent intensity of PKH26 labeled GNVs or IGNVs was measured by a fluorescent plate reader (Biotek HTS Multi-mode Readers). The fluorescent intensity of PKH26 labeled GNVs or IGNVs, expressed as % of transwell efficiency of fluorescent intensity of PKH26 labeled GNVs or IGNVs, was determined as follows: (PKH26 fluorescent intensity of the bottom well at the time of samples which were harvested/total PKH26 fluorescent intensity of PKH26 labeled GNVs or IGNVs added to the top well of the chamber at the beginning of culture)×100%. The media from the lower chamber was collected and centrifuged. Then the particles were resuspended in ddH2O, smeared onto a slide and 4',6-diamidino- 2-plaenylindole (DAPI) stained. The number of HUVEC cell associated particles in the lower chamber was estimated by counting 10 randomly selected fields (×20 magnification) using Image) software. None of the samples examined were positive for DAPI staining.

Hematoxylin and Eosin (H&E) and immunohistochemistry (IHC) staining. Livers, lungs, spleens, kidneys from BALB/c mice treated with PBS or IGNVs (200 nmol and 800 nmol, I.V. injection for three times) and colon tissues from DSS fed mice were fixed overnight in 4% paraformaldehyde and embedded in paraffin; 5 μm sections of tissues were than stained with H&E.

Human breast cancer tissues and colon cancer tissues were collected in Huai'an First People's Hospital of China. All patients provided written informed consent. The use of human tissues in this study was approved by the institutional review board of the Huai'an First People's Hospital of China and was conducted in accordance with international guidelines for the use of human tissues. Paraffin embedded breast cancer, colon cancer and adjacent tissues sections (5 μm) were rehydrated and heated in an antigen retrieval solution for 45 min. Endogenous peroxidase activity was inhibited by incubation with 3% hydrogen peroxide for 10 min. at 22° C. and the non-specific sites were blocked with 5% BSA for 45 min. The sectioned tissues on slides were then incubated with primary antibodies [(polyclonal anti-CXCL1 (0.15 μg/ml), polyclonal anti-CXCL10 (1 μg/ml), anti-CCL2 (1 μg/ml), and CCL52 (5 μg/ml)] overnight at 4° C. Sections were processed with appropriate biotinylated secondary antibody and a streptavidin biotin peroxidase amplification kit (Vectastain, Vector Laboratories, Burlingame, CA). The peroxidase reaction was finally developed with diaminobenzidine (Dako) and sections were counter stained with player's haematoxylin. Slides were counterstained with weak Mayer's hematoxylin solution for 2 min. Negative control slides were prepared without addition of primary antibody. The degree of expression of chemokine was recorded independently by two expert observers as a percentage of cells positive for the chemokine based on a visual assessment of the intensity of brown reaction product within the cytoplasmic regions of each image on a scale of 0 (no staining) to 3+(intense staining). To quantify the staining intensity, an average score was then calculated by summing the individual intensity level scores.

In vivo image. To evaluate the stability of circulating IGNVs in mice, 200 nmol of DiR dye-labeled IGNVs were injected into mice via the tail vein. Blood was drawn into an anti-coagulant tube at various time points (3 h, 24 h, 48 h, 72 h and 120 h) after the injection. The intensity of DiR signals from equal volume blood samples were then measured using a Kodak Image Station (4000 MM Pro system, Carestream, Woodbridge, CT) and quantified using the Carestream MI software.

To track the IGNVs in ILS-induced acute skin inflammation of mice, DiR dye labeled IGNVs (20, 40, 150, 300 nmol) were I.V. injected into mice. At 6 h and 24 h after the injection, images of living mice were obtained using a Kodak Image Station. Inflamed skin was then removed 24 h after IGNV administration and the DiR dye signals in the skin were quantified.

To study targeted delivery of IGNVs in DSS-induced colitis mice, DiR dye labeled IGNVs or GNVs (200 nmol) were I.V. injected into normal mice or colitis mice having been provided 2.5% DSS in their drinking water for 5 days. 24 h after a single I.V. injection, colons were collected and scanned using a Kodak Image Station and quantified using the vendor software.

For biodistribution of IGNVs in tumor-bearing mice, mouse colon tumor (CT26) and breast tumor (4T1) bearing mice were I.V. administrated DiR dye labeled IGNVs (200 nmol) or GNVs (200 nmol). Whole body imaging was done at 6 h and 24 h after the injection. DiR dye signals in both CT26 and 4T1 tumor tissues were also quantitatively measured 24 h after the injection.

To determine the effects of chemokines on the homing of IGNVs, 200 nmol of DiR dye labeled IGNVs were pre-incubated with tissue extract, or a 100 ng of each of the recombinant chemokines, i.e., CXCL1, CXCL2, CXCL9, CXCL10, CCL2, CCL5, or combinations of CXCL1/2, CXCL9/10, CCL2/5 or CXCL1/2/9/10 plus CCL2/5 overnight at 4° C. IGNVs were then washed at 100,000 g for 20 min at 4° C., resuspended in 100 μl PBS, and injected into LPS-induce acute skin inflammation mice or CT26 tumor-bearing mice. 24 hr after the injection, skin or tumors were removed and the DiR dye signals were quantitatively measured using a Kodak Image Station and quantified using the vendor software.

Cytokines assays. To evaluate the potential toxicity of IGNVs and commercial liposomes, 200 nmol and 800 nmol of IGNVs or commercial liposomes as controls were I.V. injected into BALB/c mice daily for 3 days. 24 h after the last injection, peripheral blood was collected and cytokines (TNF-α, IL-6 and IL-1β) were measured using ELISA kits.

To determine the effect of curcumin delivered by IGNVs on the inhibition of induction of TNF-α, IL-6 and IL-1β, colon tissues from DSS-induced colitis mice were cultured ex vivo and TNF-α, IL-6 and IL-1β quantified. The colon tissues from DSS induced colitis mice that had been previously I.V. injected with PBS, GNVs (200 nmol), IGNVs (200 nmol), curcumin (50 mg/kg), GNV-Cur (50 mg/kg) or IGNV-Cur (50 mg/kg) every 2 days for 5 times were collected for ex vivo culture. In brief, the distal most 2 cm of the colon was washed with PBS containing penicillin/streptomycin and then further cut into 1 cm² sections. Colon sections were cultured in serum free RPMI 1640 medium supplemented with penicillin streptomycin. After 24 h in culture, cell-free supernatants were harvested and assayed for cytokine secretion using ELISA kits (eBioscience).

To measure human chemokines released in cultured supernatants of SW620 human colon cancer cells, 2×10⁵ cells/well were cultured in 6-well plates. After 48 h in culture, the medium was collected and CCL2, CCL2 and CXCL10 were analyzed using the ELISA MAX™ Deluxe Set from Biolegend.

Induction of local skin inflammation. Dermal inflammation of C57BL/6j mice (body weight=25 to 30 g) was induced by a single intradermal injection in the flank region of 30 μg of LPS (*Escherichia coli* 0111:B4) in 50 μl of isotonic saline solution. 6 h after the injection, mice with a visible local skin inflammatory response were recruited for this study.

DSS-induced colitis model. Colitis was induced using 2.5% (w/v) dextran sodium sulfate that had been added to the drinking water. The DSS solution was prepared fresh every other day. To assess the therapeutic effects of curcumin delivered by IGNVs on colitis, beginning on day 3 after mice were provided with 2.5% DSS in their drinking water, mice were I.V. injected with PBS, free GNVs (200 nmol), IGNVs (200 nmol), free curcumin (50 mg/kg), curcumin loaded GNVs (50 mg/kg) or curcumin loaded IGNVs (50 mg/kg) every 2 days for total of 5 injections. Body weight and the presence of blood in the stool were monitored daily.

Measurement of the concentration of curcumin in mice colon tissues. DSS-induced colitis mice were I.V. injected with PBS, GNVs, IGNVs, free curcumin, GNV-Cur or IGNV-Cur every 2 days, the curcumin in colon tissues was quantitatively analyzed using high performance liquid chromatography (HPLC) as previously described. In brief, colon tissues were collected 6 h after last injection, weighed and placed in 1 ml PBS and homogenized. Fifty μl of citrate buffer solution was added to 0.8 ml of aliquots of the homogenized samples and vortexed for 30 s, followed by addition of 2 ml of ethyl acetate. The supernatants were then collected after 1000×g centrifugation for 5 min and dried under a stream of nitrogen gas. The obtained solid samples were re-dissolved in. 100 μl of methanol and centrifuged at 10,000×g for 10 min. Twenty μl of supernatant were used for HPLC analysis. Curcumin was detected by reversed phase-HPLC with a DAD detector (Agilent 1100, USA) at a flow rate of 1 ml/min. The solvent system was (A) ddH2O and (B) acetonitrile containing 0.1% TFA. The following gradients of mobile phase B were used to run the column: 10-50% for 0-18 train, 50-90% for 18-25 min, 90% for 25-30 min. and 90-10% for 30-35 min.

CT26 and 4T1 tumor mice models. Xenograft tumor growth models were used to demonstrate IGNV mediated targeted delivery of chemotherapy drug to tumors versus free doxorubicin (Free DOX) or GNVDOX. In the first set of experiments, six-week-old female BALB/c mice were subcutaneously injected with the murine colon cancer CT26 cell line ($5.0 \times 10^5$ cells/mouse in 50 μl of PBS). In a second set of experiments, six-week-old female BALBIc mice were injected in a mammary fat pad with the murine breast tumor 4T1 cell line ($5.0 \times 10^5$ cells/mouse in 50 μl of PBS). When tumors reached approximately 60 mm$^3$ in volume, the mice were randomly assigned to different treatment groups and I.V. injected with free GNVs, IGNVs, doxorubicin (DOX, 100 μg), GNVs loaded with DOX (GNV-DOX, 100 μg DOX) or IGNVs loaded with DOX (IGNV-DOX, 100 μg DOX). Mice were treated every 3 days for 30 days. Growth of the tumors was measured using a method as described previously.

Loading efficiency. To evaluate the loading efficiency of doxorubicin and curcumin in IGNVs, GNV-DOX or GNV-Cur particles were prepared by adding 200 μg of doxorubicin or curcumin into a grapefruit lipid film, and were subsequently sonicated using a method as described previously. To further make IGNV-DOX or IGNV-Cur, the GNV-DOX or GNV-Cur particles formed through sonication as described above were mixed with EL4 cell plasma membrane-derived vesicles and then extruded 15-20 times through an Avanti mini extruder with a 200 nm polycarbonate porous membrane. The resulting suspension was centrifuged at 100,000×g for 30 min. The supernatants were collected and the residual doxorubicin or curcumin content was measured using a CARY 100 Bio UV-Visible Spectrophotometer at a wavelength of 497 and 426 nm, respectively. The loading efficiency was calculated as follows: Loading efficiency=(Total drug-free drug)/Total drug×100%.

Release profile of chemotherapy drugs. To test the in vitro profile of doxorubicin released from IGNV-DOX or DOX-NP™ purchased from Avanti Polar Lipids Inc. (Alabaster, Alabama, USA), IGNV-DOX or DOX-NP™ with 200 μg doxorubicin were suspended in 1 ml of PBS buffer solution at differing pH values of 5.0, 5.5, 6.0, 6.5 and 7.2. Each suspension was placed at 37° C. with shaking. At a predetermined time (0.5, 1, 2, 3, 6 and 24 h), suspensions were centrifuged at 100,000×g for 30 min. The amount of doxorubicin released from IGNVDOX or DOX-NP™ was measured spectrophotometrically at 497 nm. Release of curcumin from IGNV-Cur was also analyzed using a UV-Visible spectrophotometer set at 426 nm.

ATPlite assay. To test the potential cytotoxicity of IGNVs and commercial DOX-NP™ control liposomes, 4T1 cells were cultured in 24-well culture plates for 24 h with different doses (0, 10, 20, 40, 80, 160 nmol) of IGNVs or control liposomes from Avanti Polar Lipids Inc. (Alabaster, Alabama, USA). Cell cytotoxicity of IGNVs was measured using the Luminescence ATP Detection Assay System (PerkinElmer, Ma., USA). Briefly, 200 μl of mammalian cell lysis buffer was added into each well and the plate shaken for 5 min. 50 μl cell lysis was dispensed into an. OptiPlate, mixed with 50 μl of substrate solution, the plate shaken at 700 rpm for 5 min, and the luminescence measured using a BioTek Synergy™ HT Multidetection Microplate Reader with Gen 5 version 1.08 data analysis software (Winooski, VT, USA).

Statistical analysis. One-way analysis of variance (ANOVA) followed by Turkey Post Hoc tests was used to determine the differences occurred between groups, and T test was used to determine the difference between two groups (*$p<0.05$, $p<0.01$ and *$p<0.001$).

Example 1

Characterization of GNVs Coated with Inflammatory Chemokine Receptor Enriched Membrane Fraction of Activated T Cells (IGNVs)

Figure 1B:
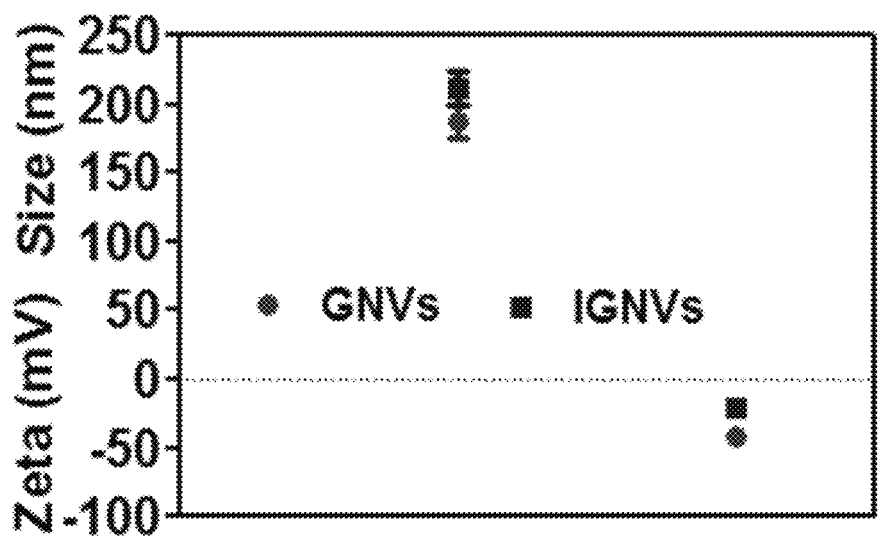
Figure 1C:
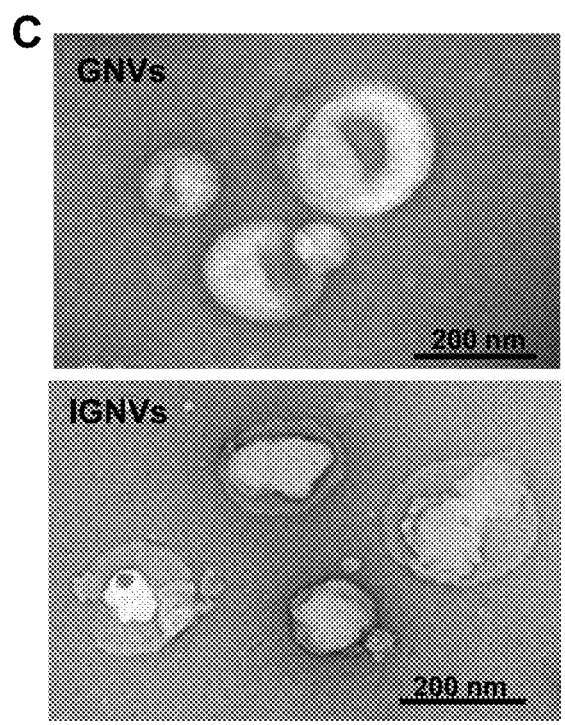
Figure 1D:
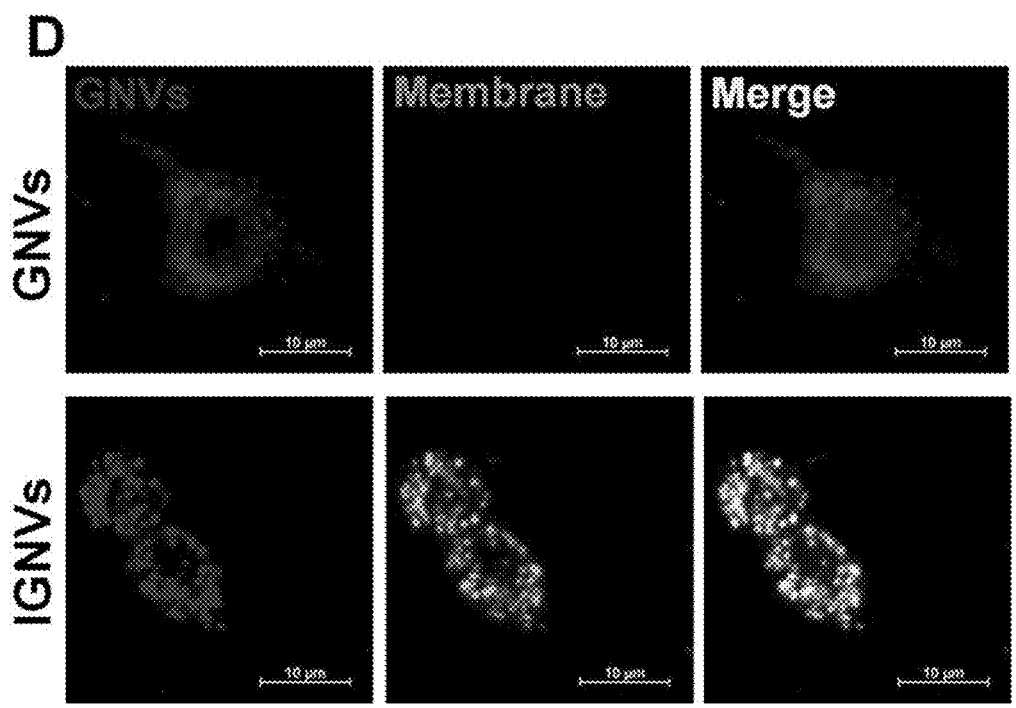
Figure 1E:
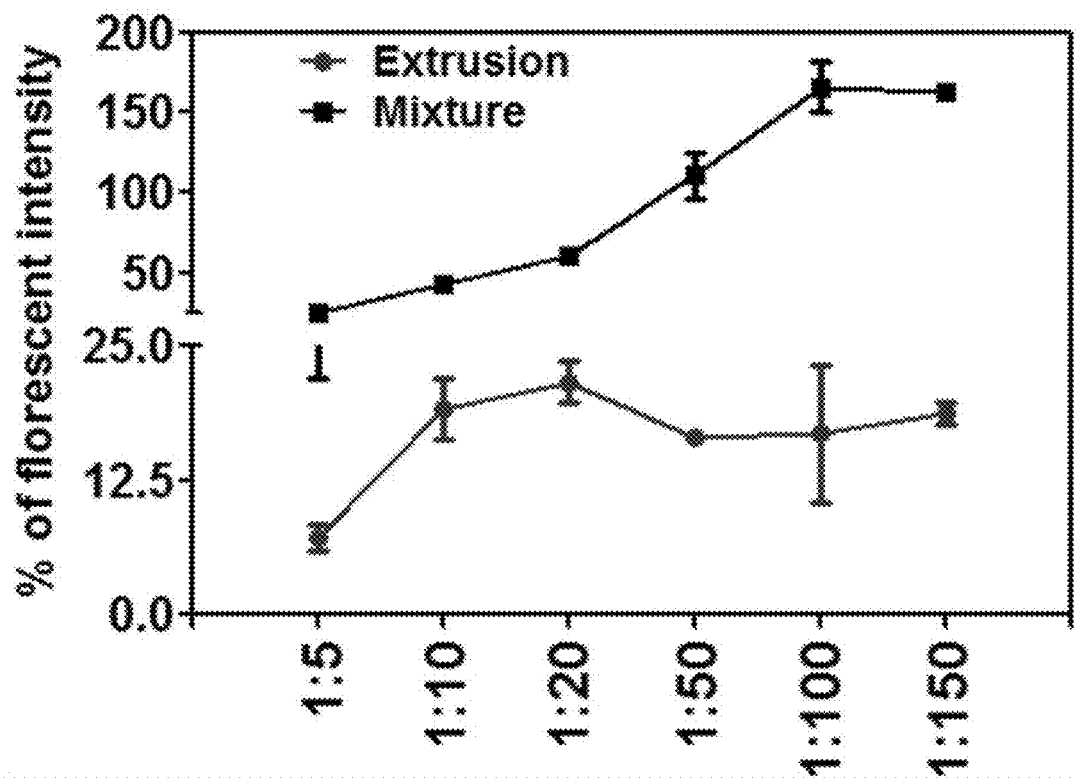
FIG. 1E is a graph showing FRET based measurements of IGNV formation, where DiO labeled GNVs and DPA labeled membrane vesicles (n=3) were mixed, where the mixture was subsequently extruded 20 times through a 200 nm polycarbonate porous membrane using an Avanti mini extruder or the mixture without further extrusion was used as a control, and where the extruded products and the mixed products were then diluted and the intensity of fluorescence was measured.
Figure 6A:
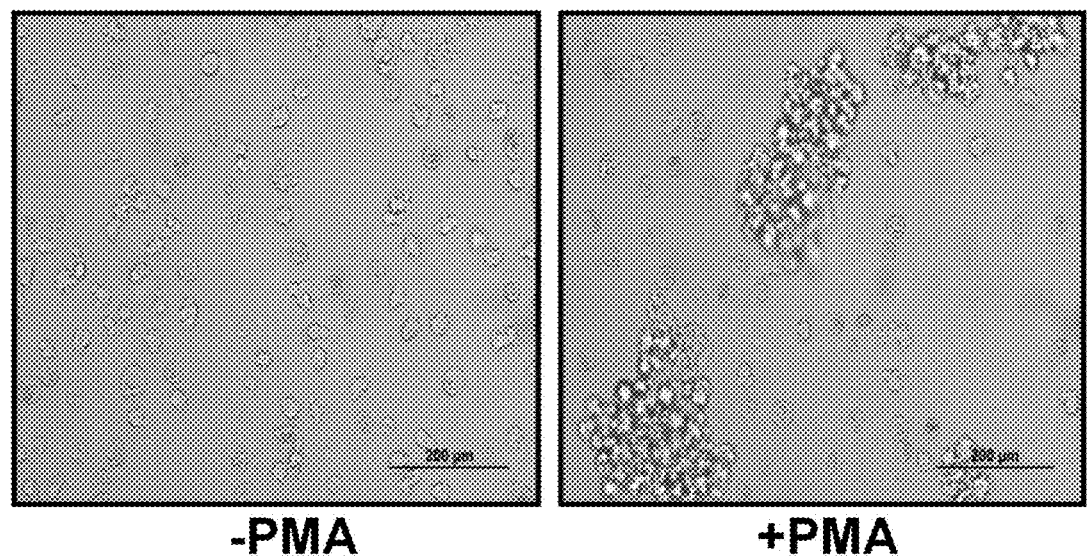
FIGS. 6A-6B include images and graphs showing chemokine receptors expressed on PMA stimulated EL4 cells.
Figure 6B:
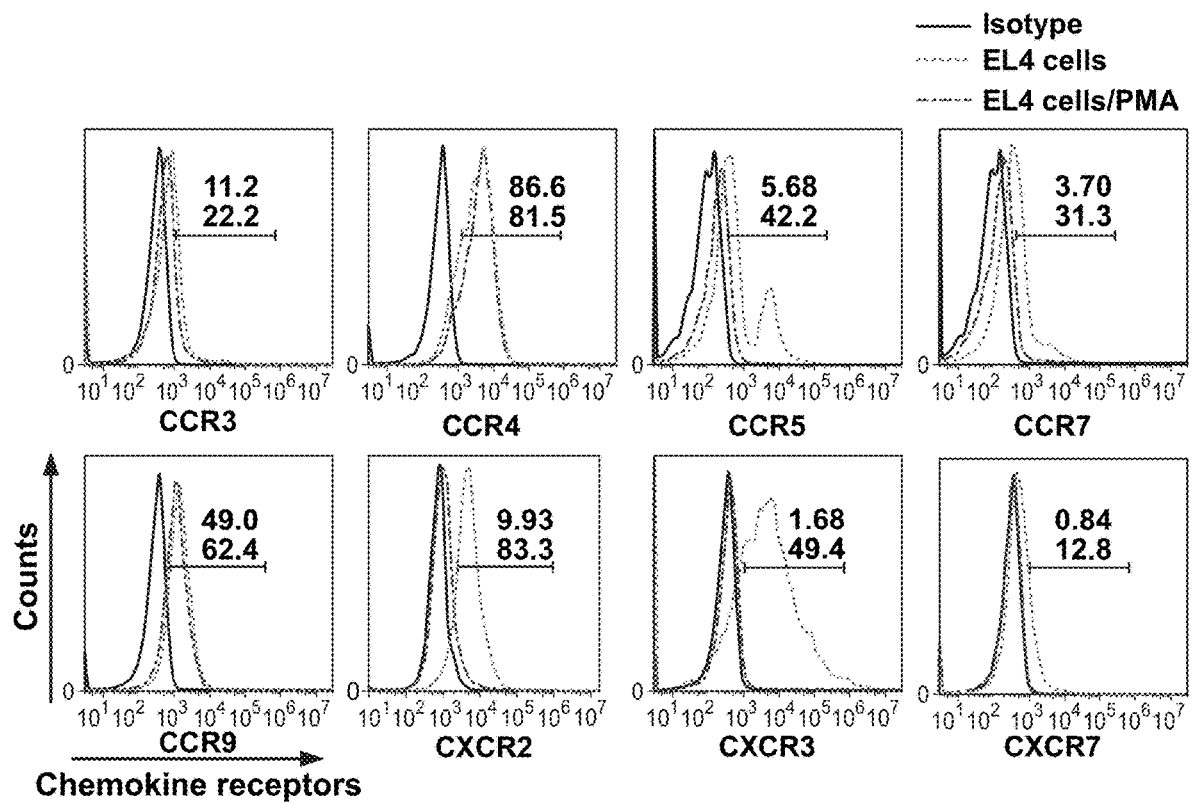
Figure 7:
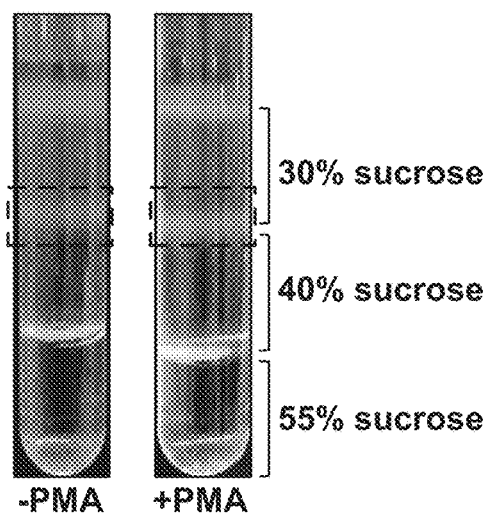
FIG. 7 is an image showing separation of EL4 plasma membrane via discontinuous sucrose gradient centrifugation, where EL4 cells with/without PMA stimulation were harvested and homogenized, and where the homogenized samples were sucrose banded and the images were taken after the centrifugation.
Figure 8:
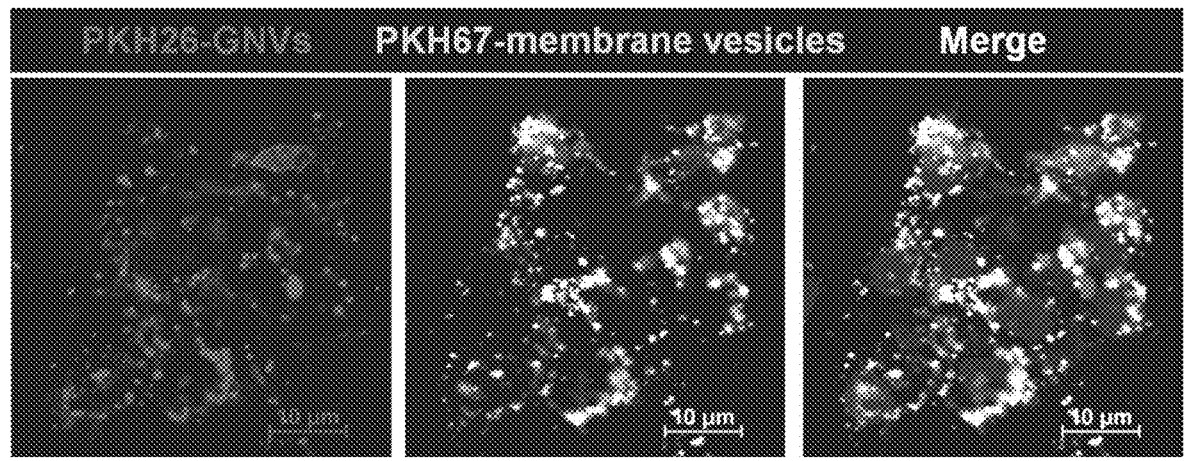
FIG. 8 includes images showing the uptake of a mixture of GNVs and membrane derived vesicles, where EL4 cell derived plasma membrane vesicles were labeled with PKH67 and GNVs were labeled with PKH26, where 4T1 cells were cultured in the presence of simply mixed PKH67-membrane vesicles and PKH26-GNVs for 12 h, and where representative images of cells (n=3) were then taken using a confocal microscope at a magnification of ×400.
Figure 9A:
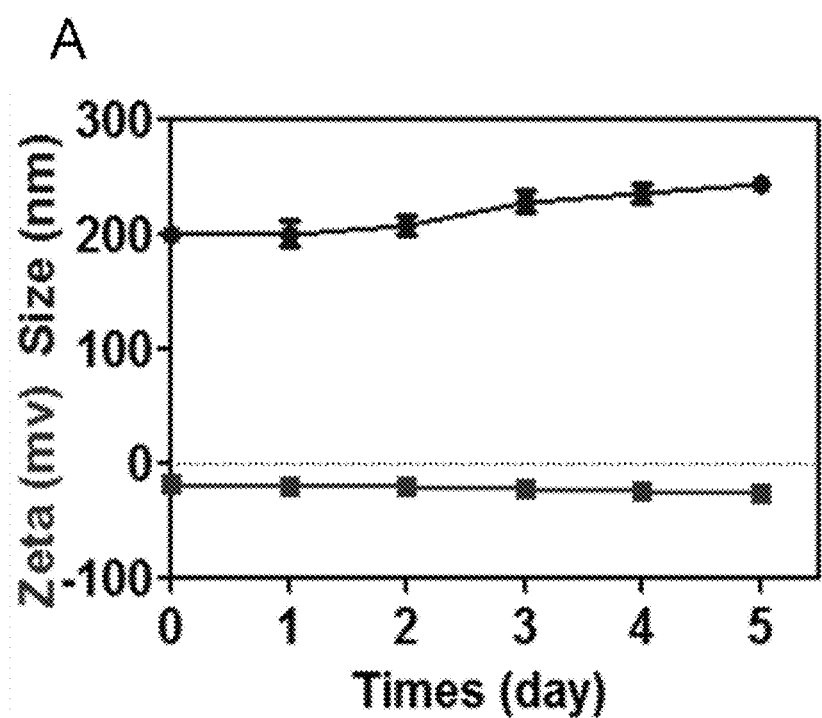
FIGS. 9A-9B include graphs showing the stability of IGNVs, where the stability of EL4 cell membrane coated GNVs (n=5) at 22° C. over a 5 day period (FIG. 9A) or at 37° C. over 25 h (FIG. 9B) were analyzed by measuring the size distribution and surface zeta potential.
Figure 9B:
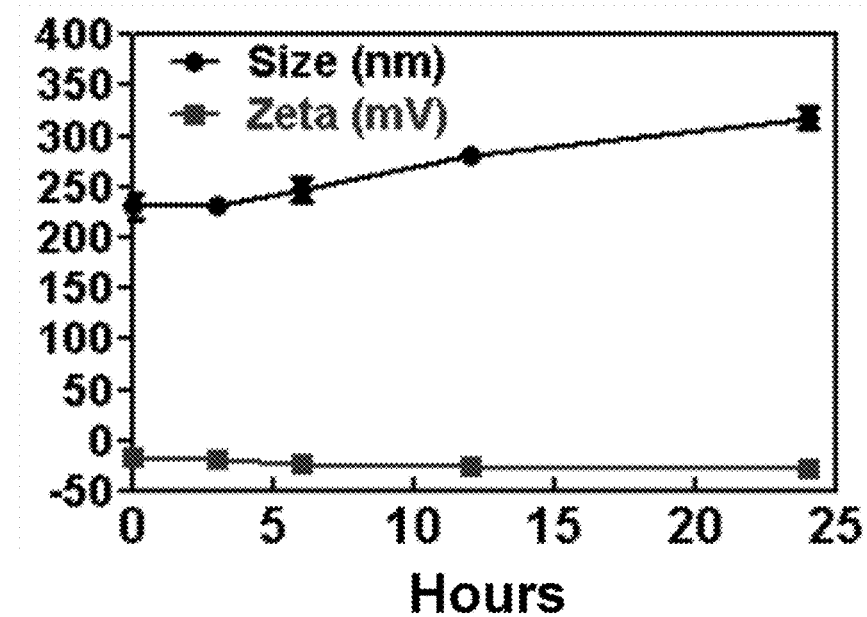
Figure 10:
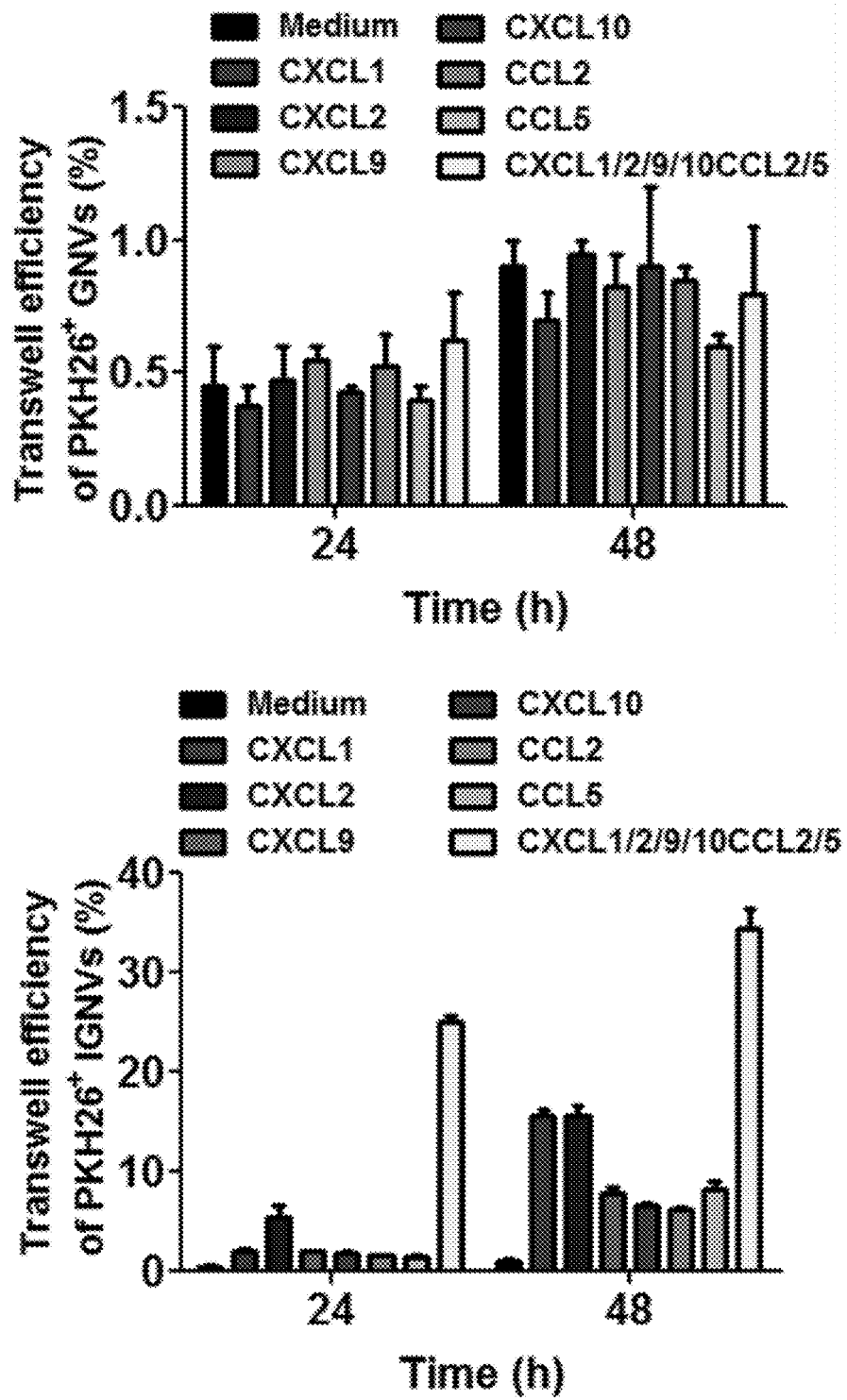
FIG. 10 includes graphs showing the transmigration of GNVs and IGNVs, where HUVEC cells were cultured in the fibronectin-coated (7.5 μg/cm$^2$) upper chamber as a transmigration barrier, where PKH26 dye labeled GNVs (upper panels) or IGNVs (lower panels) were added into the upper chamber and incubated for 24 h and 48 h, and where the PKH26 dye labeled particles in the medium of the lower chamber were measured, and expressed as a percentage of transwell efficiency of PKH26$^+$ IGNVs.

IGNVs were generated by binding membranes derived from PMA activated EL4 T cells to GNVs. IGNVs' morphology (FIG. 6A) and quantity of chemokine receptors (FIG. 6B) from EL4 T cells stimulated with/without PMA on the IGNVs was analyzed. Vesicles from the purified middle band of a sucrose gradient (FIG. 7) were prepared by extrusion and subsequently bound with GNVs. The Zeta potential and size distribution of IGNVs was then analyzed (FIG. 1B). Transmission electron microscopy (TEM) imaging (FIG. 1C) indicated that IGNVs shared a similar morphology with GNVs. IGNVs were internalized by CT26 colon cancer cells in a manner similar to GNVs (FIG. 10), and co-localized with EL4 membrane (FIG. 10, last column). Fluorescence resonance energy transfer (FRET) analysis further confirmed that more than 83±2.2% of the GNVs were coated with plasma membrane from activated EL4 T cells (IGNVs) (FIG. 1E). After preparation and through five days at 22° C. (FIG. 9A) or 25 h at 37° C. (FIG. 9B) the IGNVs were stable without significant changes in size or charge.

Example 2

IGNVs Home to Inflammatory Sites

Figure 2A:
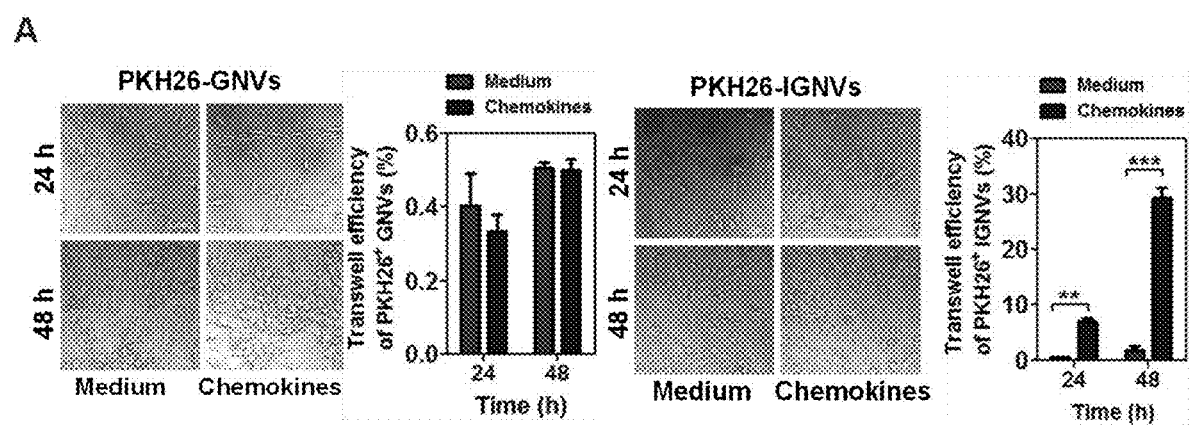
FIGS. 2A-2E include images and graphs showing the ability of IGNVs to utilize the activated leukocyte membrane dependent pathways and efficiently target and be delivered to inflammatory sites.
Figure 2B:
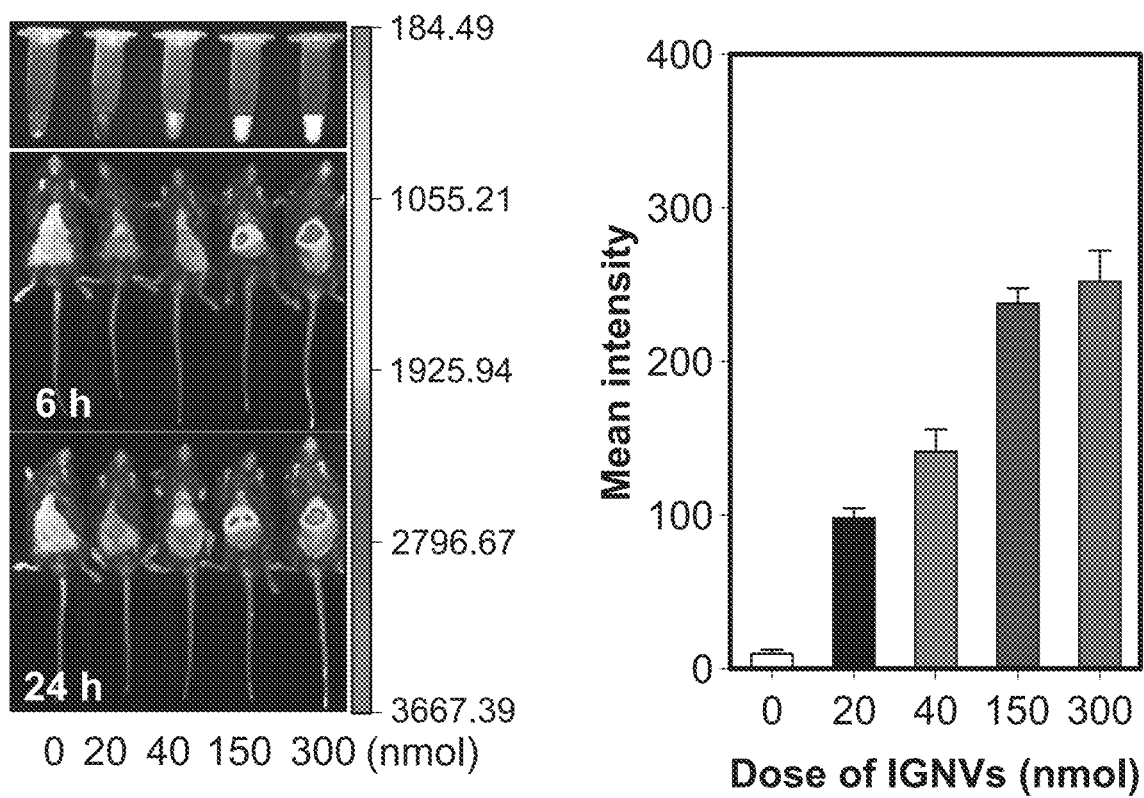
Figure 2C:
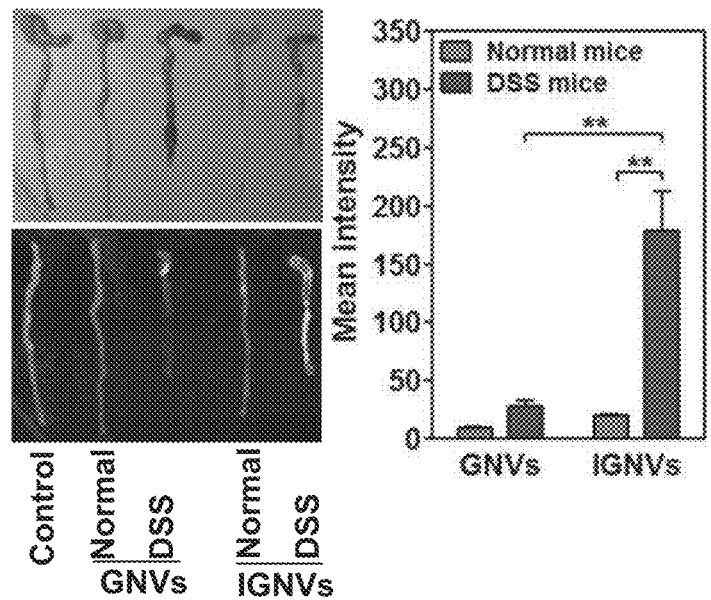
Figure 2D:
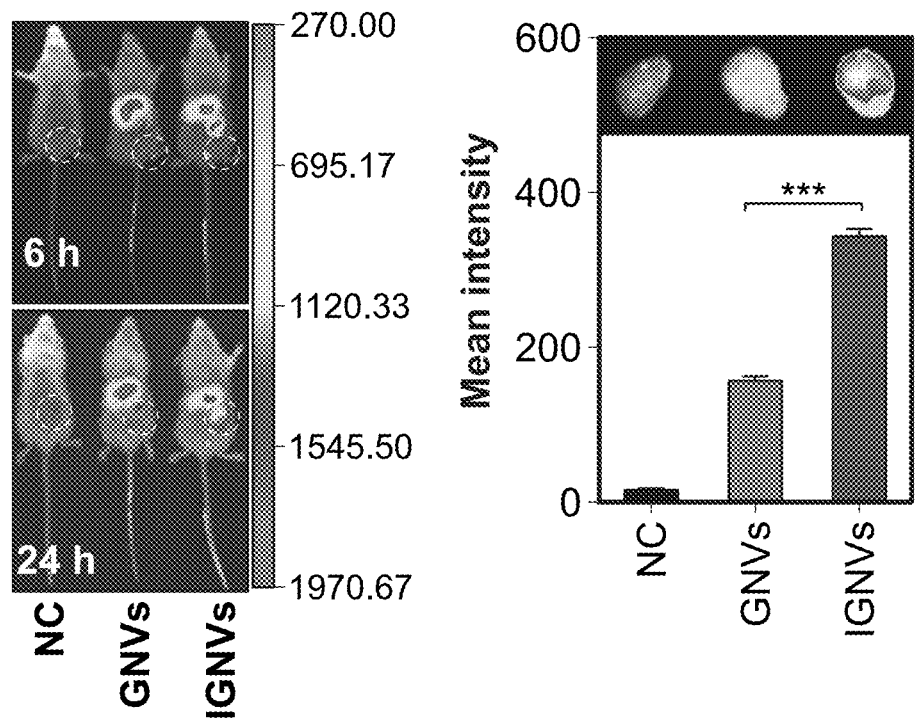
Figure 2E:
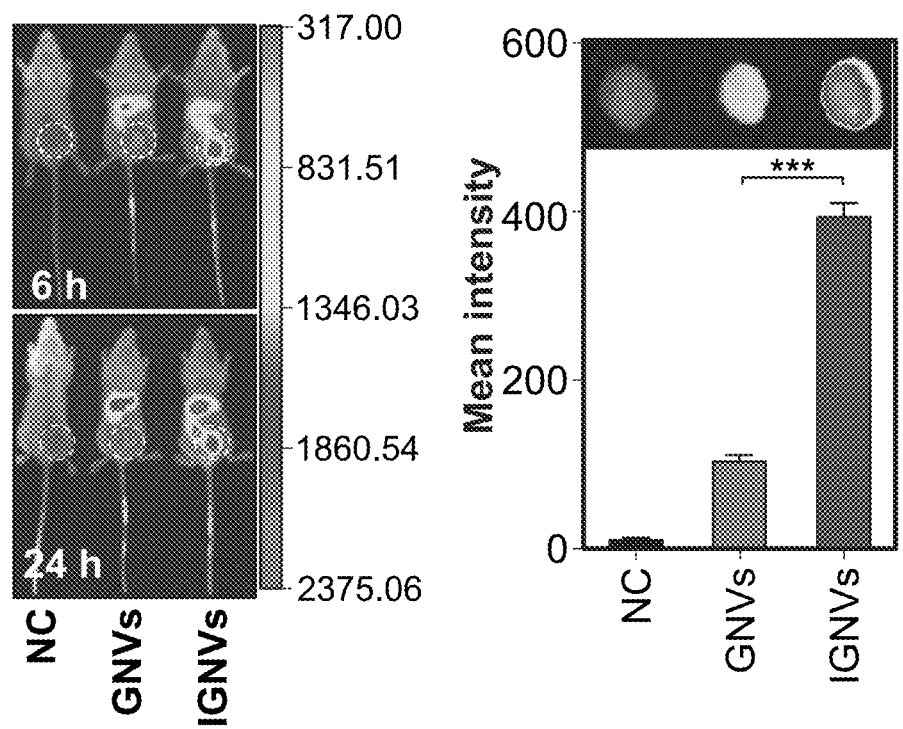

Next, to determine whether IGNVs would leave the peripheral circulation and home to inflammatory tissues, three inflammatory mouse models were tested. It was first sought to determine if IGNVs transmigrated through a HUVEC monolayer at a higher efficiency than GNVs by using an in vitro transwell assay. The data demonstrated that much higher numbers of IGNVs transfected HUVECs (DAPI$^+$PKH26$^+$) migrated to the bottom of the transwell (right panel) than GNVs (left panel) over a 48 h period (FIG. 2A). Addition of chemokines (CXCL1/2/9/10, CCL2/5) in the bottom of the transwell further enhanced the efficiency of IGNV transmigration (FIG. 2A, right panel, 4$^{th}$ column, p<0.01). Enhanced homing of IGNVs to inflammatory sites when compared with GNVs was further confirmed in different inflammatory models, two acute inflammation models (a LPS induced skin inflammation (FIG. 2B), and DSS induced colitis (FIG. 2C, p<0.01)) and two chronic inflammation cancer models (CT26 colon cancer (FIG. 2D, *p<0.001) and 4T1 breast cancer (FIG. 2E, *p<0.001)).

Example 3

Chemolune and Chemokine Receptors Play a Role in IGNV Homing

Figure 3A:
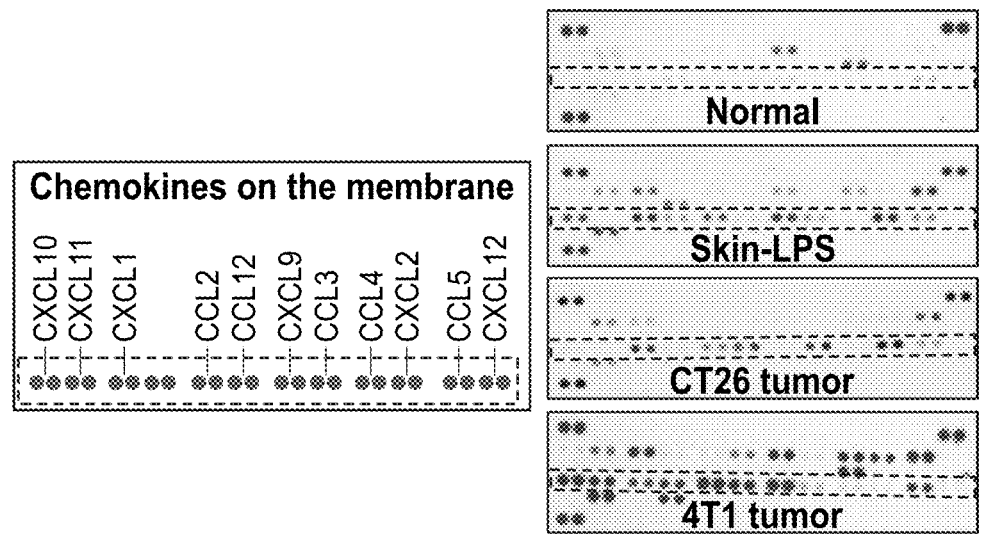
FIGS. 3A-3I include images and graphs showing the ability of chemokine mediated pathways to play a causative role in the efficient targeted delivery of IGNVs to inflammatory sites.
Figure 3B:
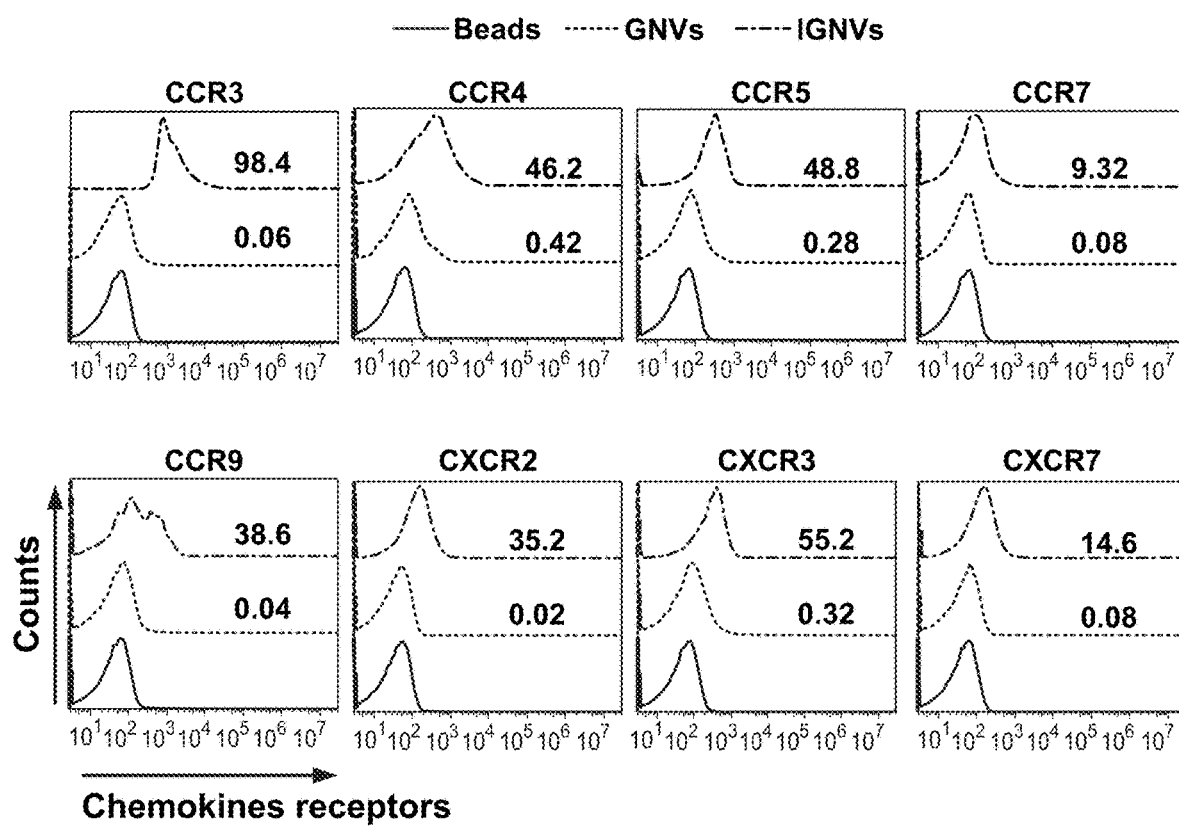
Figure 3C:
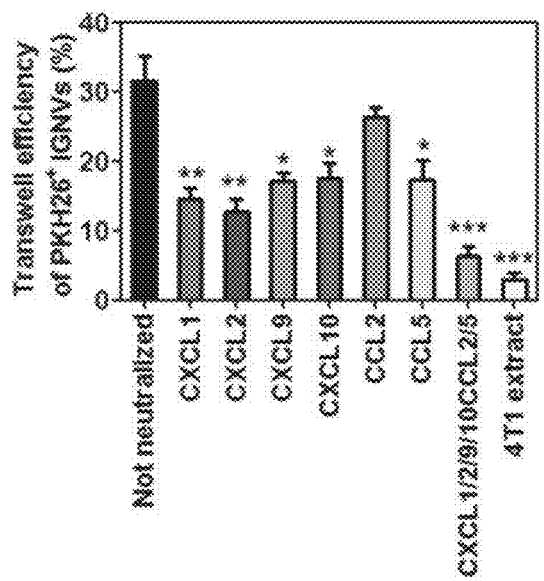
Figure 3D:
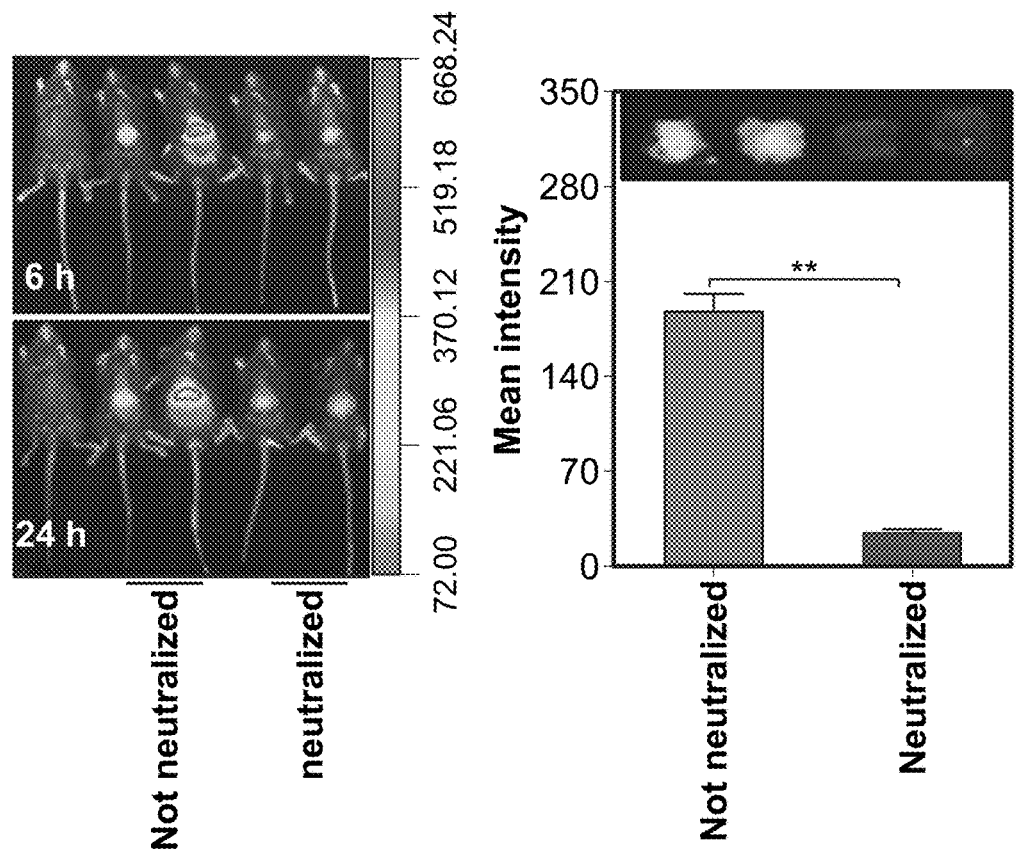

Leukocyte recruitment into inflamed tissue follows a well-defined cascade of events, beginning with capturing of free flowing leukocytes to the vessel wall, followed by rolling, adhesion to endothelial cells, post-adhesion strengthening, crawling, and finally transmigration through endothelial junctions into sites of inflammation. During these steps, chemokines/chemokine receptors play a key role in the last step, transmigration. The profiles of chemokines from the extracts of inflammatory tissues and the types of chemokine receptors coated on the IGNVs were therefore analyzed. Chemokine array data (FIG. 3A) indicated that chemokines identified are in much higher concentrations in the extracts of the inflammation models that were tested than the extracts from non-tumor mammary gland (FIG. 3A, normal). It was also noticed, in general, that stronger chemokine signals were detected in the extracts from 4T1 breast tumor than from the skin of LPS induced skin inflammation or CT26 colon tumor. FACS analysis data indicated that corresponding receptors of chemokines were detected on the IGNVs (FIG. 3B). To determine which chemokine(s) in the inflammatory tissues play a causative role in recruiting IGNVs into the inflammatory tissue, an in vitro transwell assay was conducted. The results indicated the transmigration of IGNVs was remarkably affected by addition of chemokines into the bottom of the transwells; whereas, there was no change in GNVs migration with the addition of chemokines. Addition of CXCL1 or CXCL2 resulted in more IGNVs detected in the bottom of the well 48 h post-addition, and the combination of chemokines, CXCL1/2/9/10,CCL2/5 led to the highest efficiency in transmigration of IGNVs (FIG. 10). The effects of chemokines on IGNVs transmigration was then confirmed by the results generated from a neutralizing chemokine assay. Although pre-incubation with recombinant chemokine against each chemokine receptor partially attenuated the migration of IGNVs, neutralizing all six chemokine receptors as listed or pre-incubation with 4T1 tumor extract led to a maximum reduction of IGNVs transmigration (FIG. 3C, *p<0.05, p<0.01 and *p<0.001.). This reduction was also confirmed in a LPS induced skin inflammation model in mice where the mice were I.V. injected with DiR dye labeled IGNVs that had been pre-incubated with 4T1 tumor extract (FIG. 3D, **p<0.01).

Figure 3E:
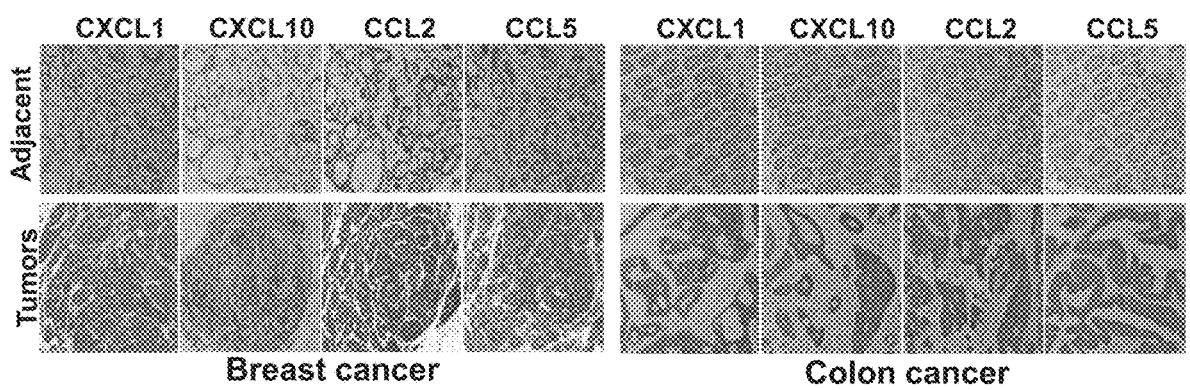
Figure 3F:
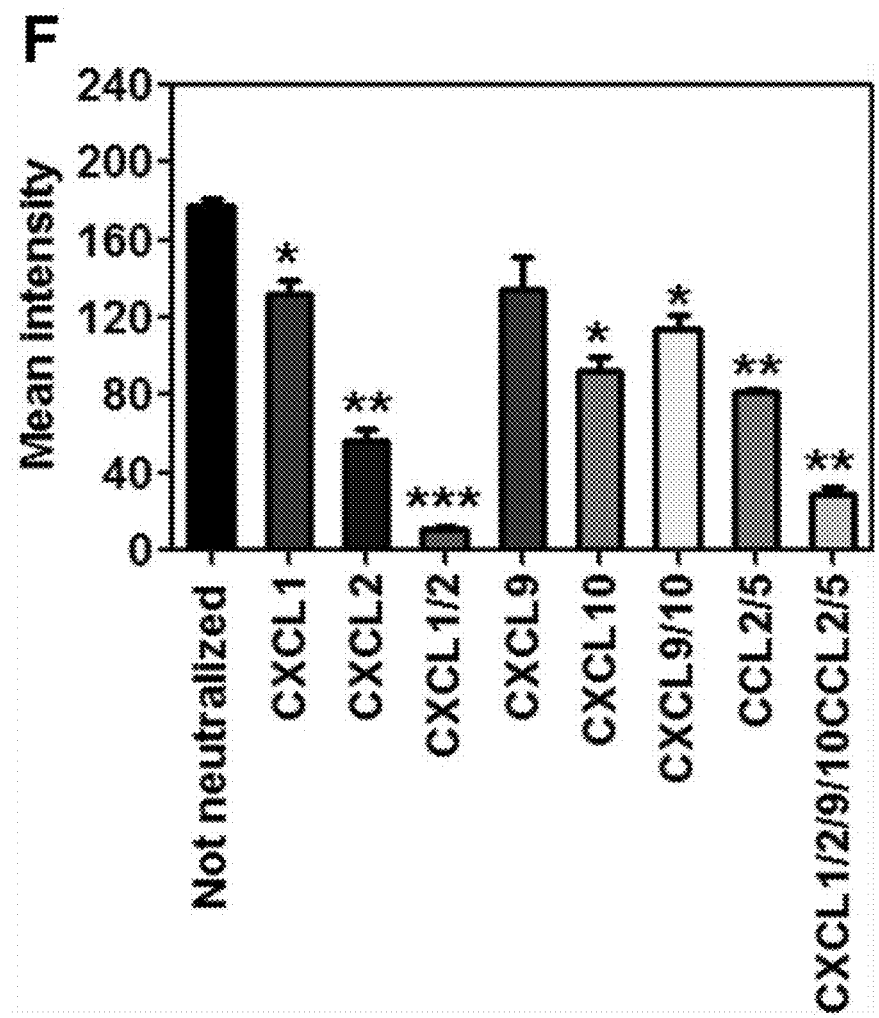
Figure 3G:
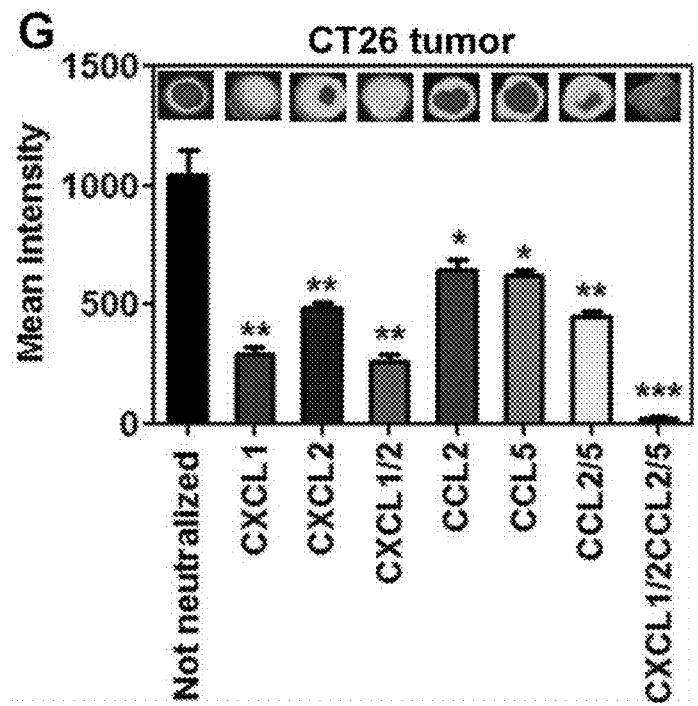
Figure 13A:
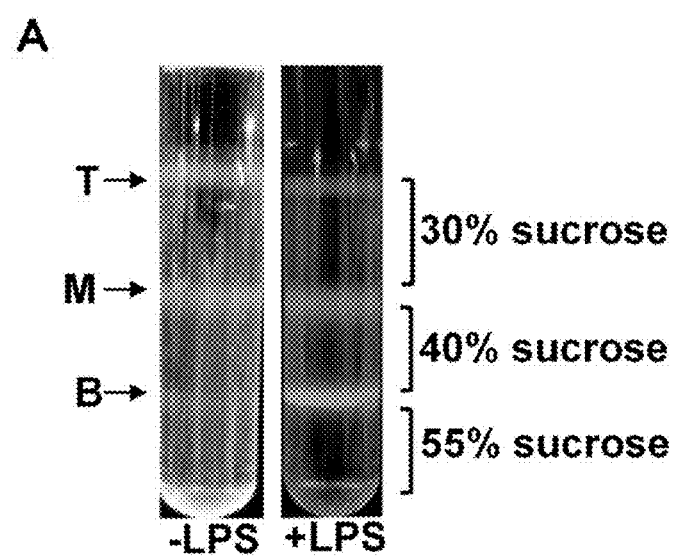
FIGS. 13A-13B include images showing the purification of plasma membranes from leukocytes, where leukocytes from peripheral blood of humans and mice were isolated and stimulated in vitro with (+LPS) (100 ng/ml) or PBS as a control (−LPS) for 24 h, and where the homogenized plasma membranes of cells from human (FIG. 13A) and mouse (FIG. 13B) were purified by sucrose gradient centrifugation. (T=top band of sucrose gradient purified membrane, M=middle band of sucrose gradient purified membrane, B=bottom band of sucrose gradient purified membrane).

The data generated from a 24 h (time course was determined based on the data from FIG. 13D) in vivo imaging analysis further confirmed that although CXCL1, CCL2 and CCL5 have an effect, CXCL2 plays a key role in homing IGNVs into inflammatory sites, including LPS induced acute inflammation in skin (FIG. 3F, *p<0.05, **p<0.01 and mp<0.001) and the CT26 colon cancer model (FIG. 3G, *p<0.05, p<0.01 and *p<0.001).

Figure 3H:
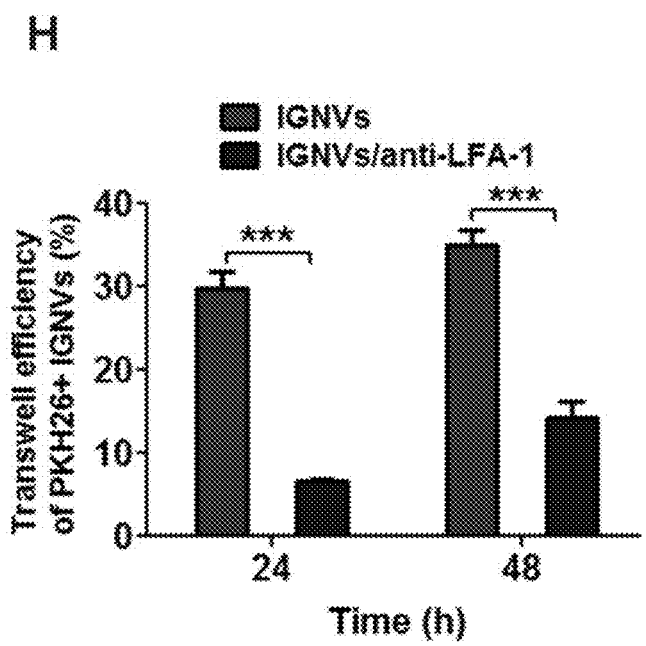
Figure 3I:
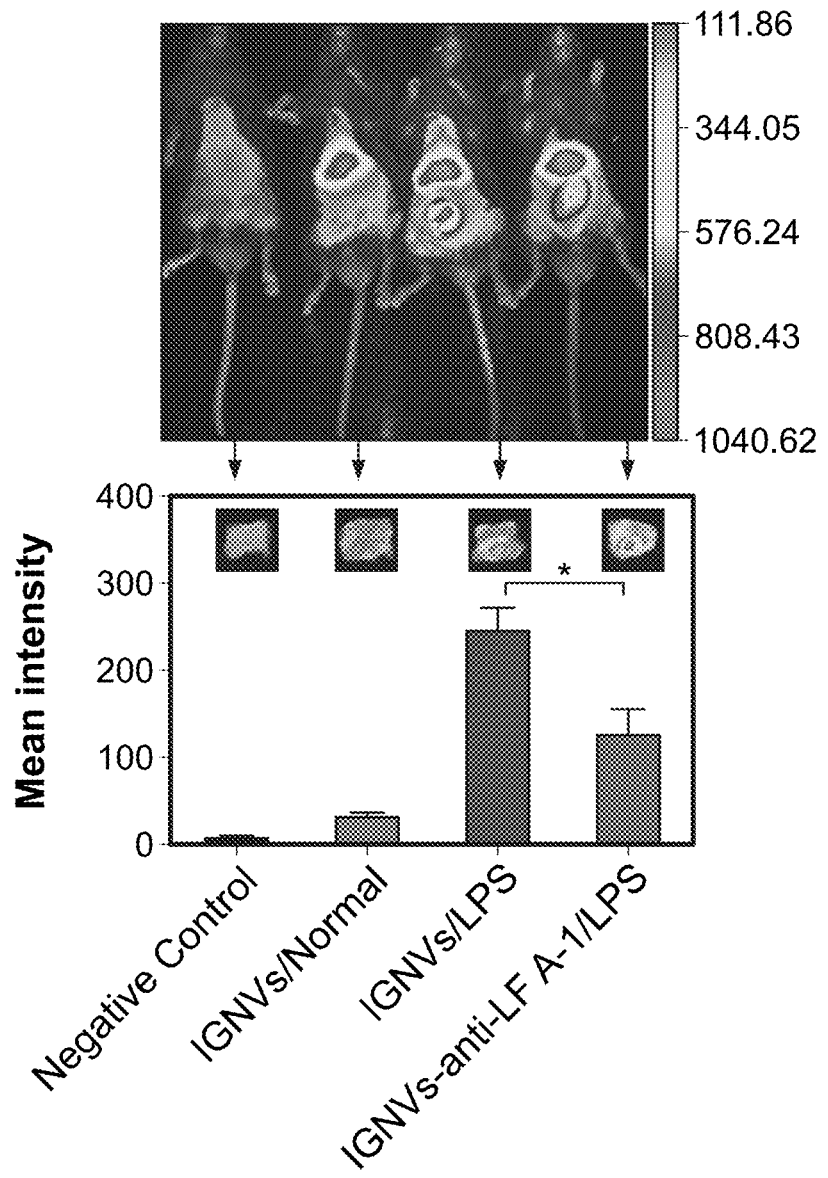
Figure 11:
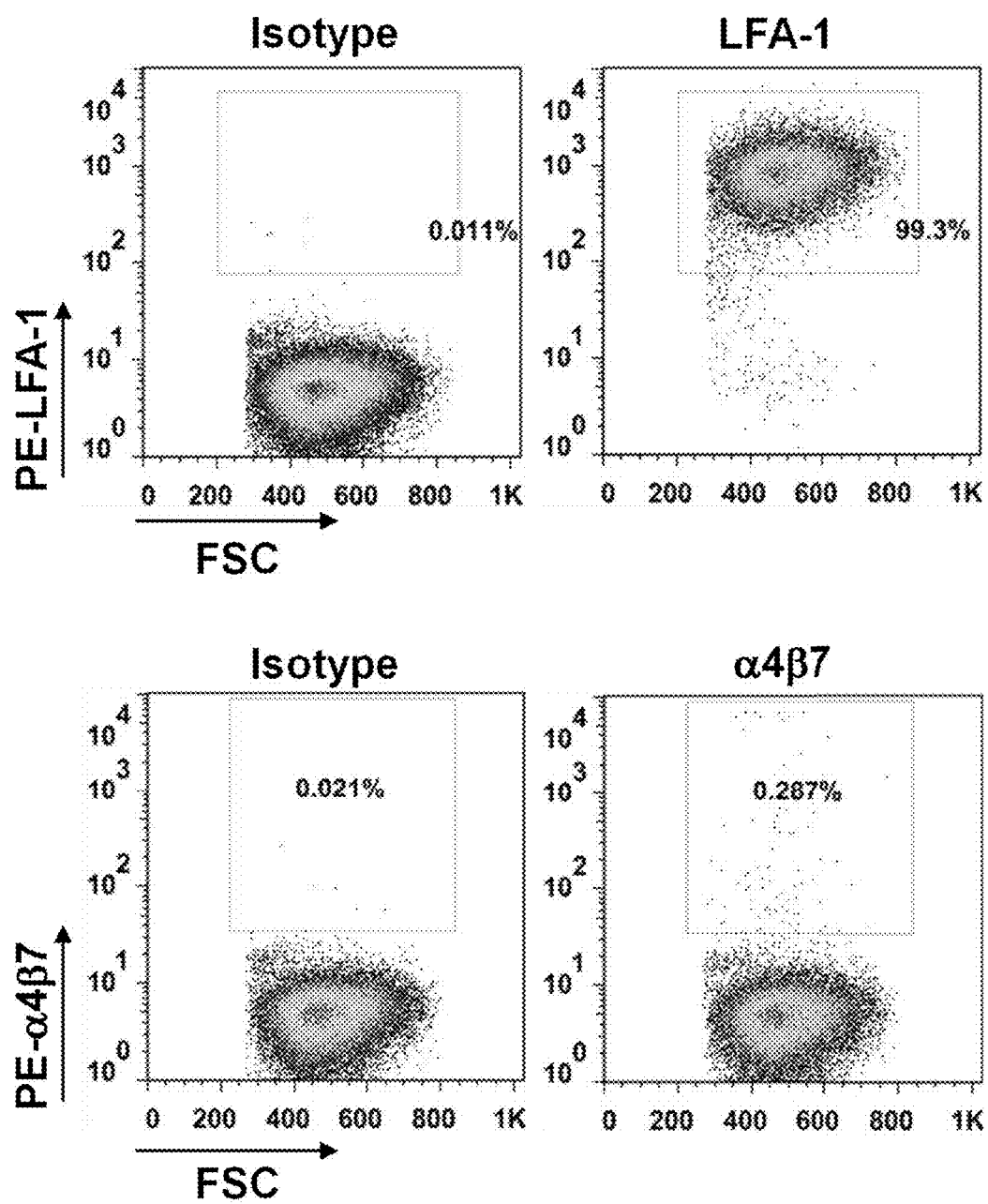
FIG. 11 includes graphs showing the expression of integrins on EL4 cells, where EL4 cells were activated with PMA and the expression of integrins (LFA-1 and α4β7) on the cells was detected by staining with PE-anti-LFA-1 and α4β7 antibodies and the percentage of integrin-positive cells were analyzed by FACS.
Figure 12:
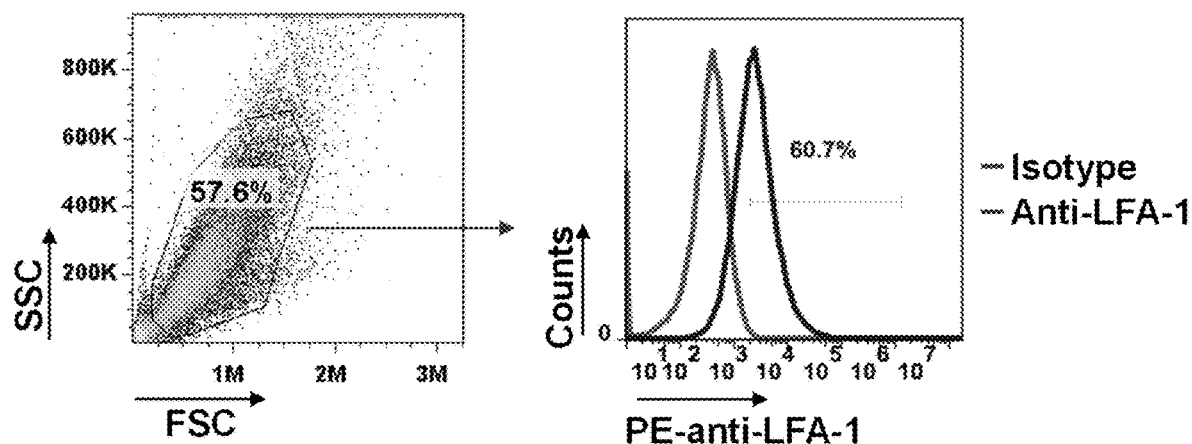
FIG. 12 includes graphs showing LFA-1 on IGNVs, where IGNVs were freshly prepared and conjugated with latex beads, and where the percentage of LFA-1 positive IGNVs was quantified by FACS analysis of PE-anti-LFA-1 stained IGNVs.

Integrins, including LFA-1 and α4β7, have multiple functions in the process of leukocyte recruitment from initially adhering to vessel walls to crawling prior to the final step, transmigration. FACS data indicated that although no α4β7 was detected, LFA-1 was highly expressed on both PMA-activated EL4 cells (FIG. 11) and present on. IGNVs (FIG. 12). Transmigation of IGNVs was dramatically decreased in vitro (FIG. 3H, ***p<0.001) and in vivo (FIG. 3I, *p<0.05) when LEA-1 on IGNVs was neutralized. Since multiple factors including LFA-1 play a role in the process of leukocytes and nanoparticles homing to inflammatory sites, and chemokines/chemokine receptors has been known to play important roles in the last step (transmigration) of leukocyte homing to inflammatory tissue in general, chemokine related assays were used as a primary determinant of function without further analysis of the role of IGNV LFA-1.

It was further determined whether the chemokines of interest were up-regulated in human cancer tissues. The results from immunohistological staining of chemokines in human colon cancer (Table 1) and breast cancer (Table 2) suggested a much higher expression of CXCL1, CXCL10, CCL2, and CCL5 in tumor tissues than in adjacent non-tumor tissues (FIG. 3E, Tables 3, 4).

TABLE 1

Characteristics of 20 Colon Cancer Patients.

| Characteristics | n |
|---|---|
| Sex | |
| male | 13 |
| female | 7 |
| Age | |
| male | 59.85 ± 3.027 |
| female | 56.88 ± 4.129 |
| Differentiation | |
| well/moderate | 14 |
| poor | 6 |
| Lymph node involvement | |
| yes | 14 |
| no | 6 |

TABLE 2

Characteristics of 21 Breast Cancer Patients.

| Characteristics | n |
|---|---|
| Cases | 21 |
| Age | 54.81 ± 2.126 |
| Lymph node involvement | |
| yes | 9 |
| no | 12 |

TABLE 3

IHC Scores of Chemokines (CXCL1, CXCL10, CCL2, and CCL5) in Human Colon Cancer Tissues.

| Chemokines | Expression Levels | | | |
|---|---|---|---|---|
| | − | + | ++ | +++ |
| CXCL1 | | | | |
| Adjacent | 11 | 8 | 1 | |
| Tumor tissue | | 2 | 6 | 12 |

TABLE 3-continued

IHC Scores of Chemokines (CXCL1, CXCL10, CCL2, and CCL5) in Human Colon Cancer Tissues.

| Chemokines | Expression Levels | | | |
|---|---|---|---|---|
| | − | + | ++ | +++ |
| CXCL2 | | | | |
| Adjacent | 8 | 10 | 2 | |
| Tumor tissue | | 1 | 8 | 11 |
| CCL2 | | | | |
| Adjacent | 11 | 9 | | |
| Tumor tissue | | | 5 | 15 |
| CCL5 | | | | |
| Adjacent | 11 | 9 | | |
| Tumor tissue | | | 12 | 8 |

TABLE 4

IHC Scores of Chemokines (CXCL1, CXCL10, CCL2, and CCL5) in Human Breast Cancer Tissues.

| Chemokines | Expression Levels | | | |
|---|---|---|---|---|
| | − | + | ++ | +++ |
| CXCL1 | | | | |
| Adjacent | 13 | 8 | | |
| Tumor tissue | | 3 | 6 | 12 |
| CXCL2 | | | | |
| Adjacent | 18 | 3 | | |
| Tumor tissue | | 2 | 10 | 9 |
| CCL2 | | | | |
| Adjacent | 13 | 8 | | |
| Tumor tissue | | | 5 | 16 |
| CCL5 | | | | |
| Adjacent | 18 | 3 | | |
| Tumor tissue | | 1 | 8 | 12 |

Figure 4A:
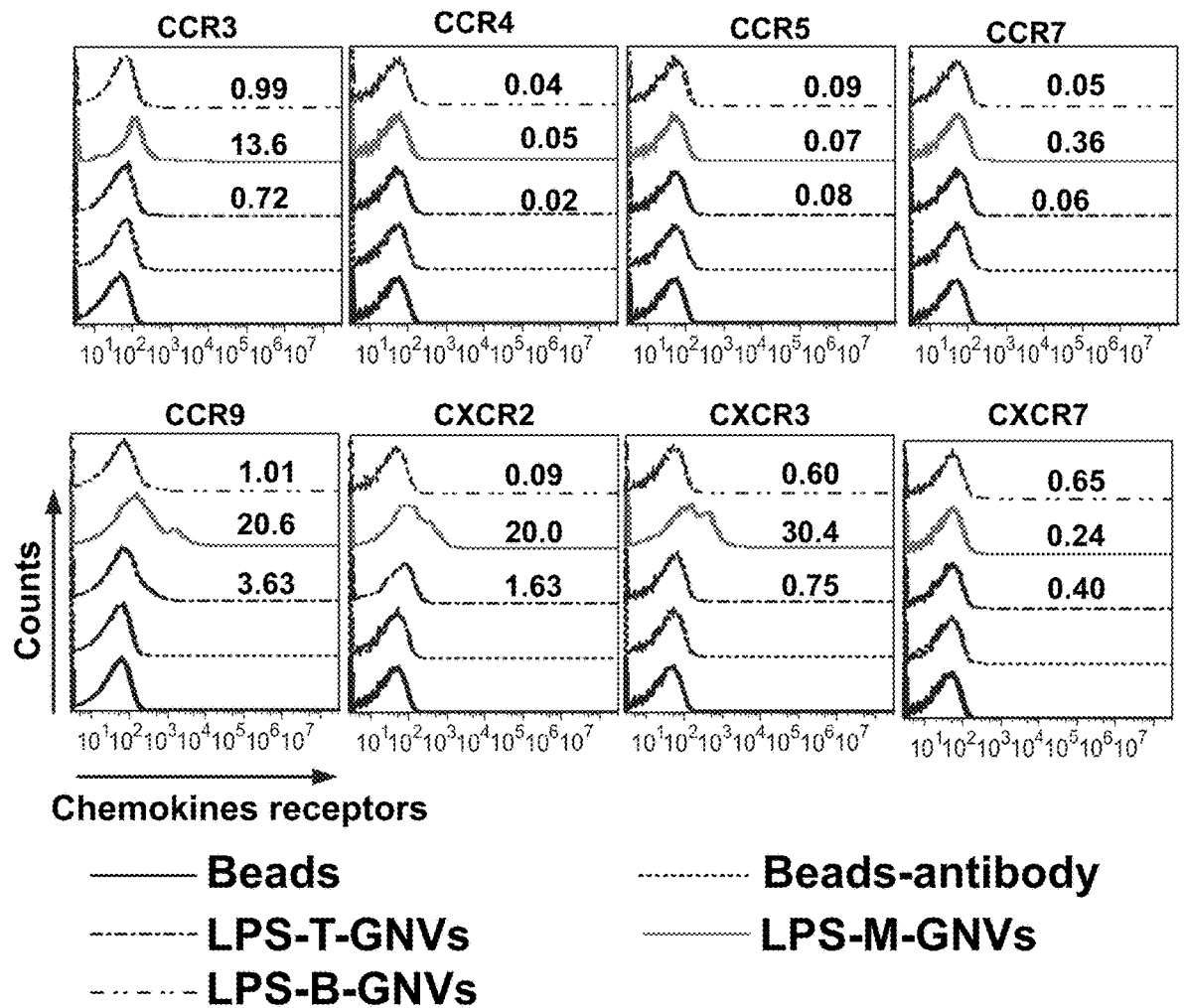
FIGS. 4A-4E include images and graphs showing the targeting to human colon cancer by coating GNVs with the plasma membrane of LPS stimulated leukocytes isolated from peripheral blood of healthy human subjects (hIGNVs) or of mice (inIGNVs).
Figure 4B:
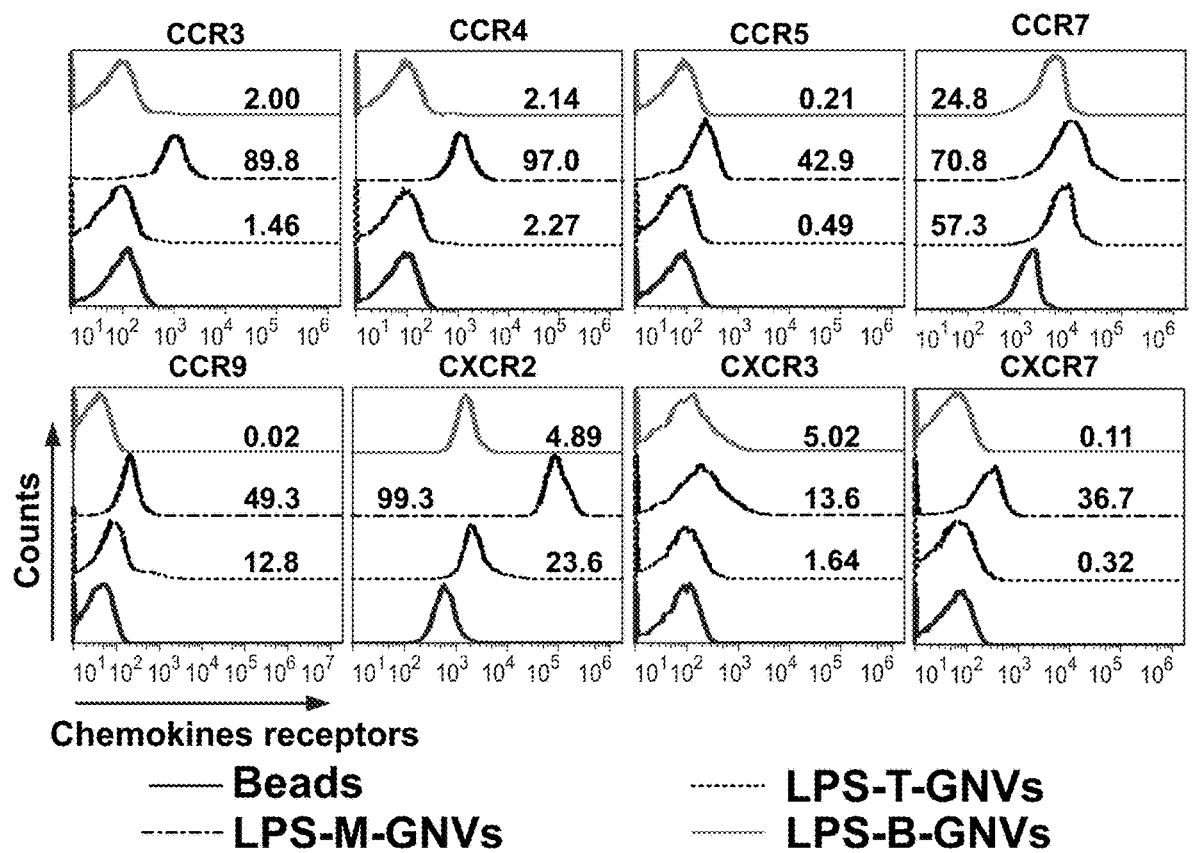
Figure 4C:
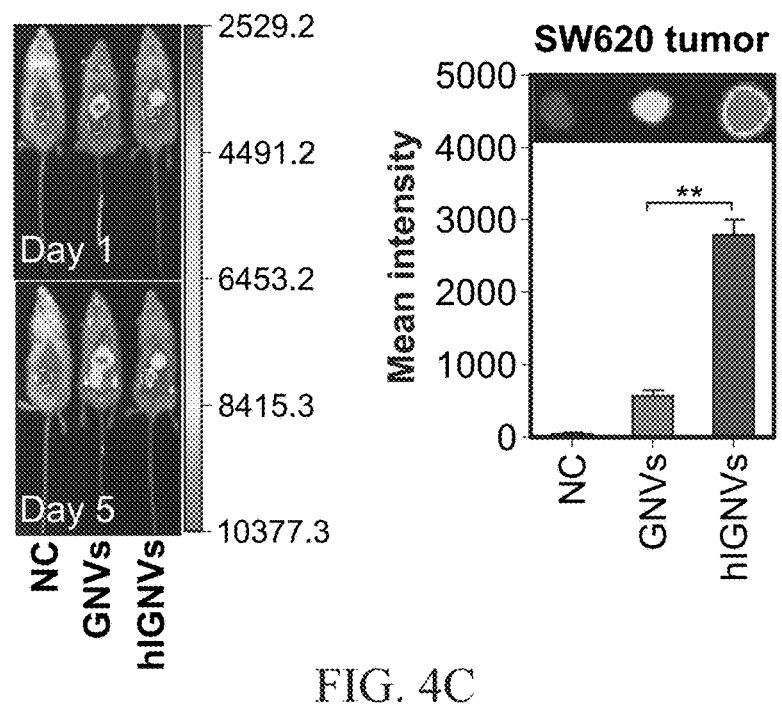
Figure 4D:
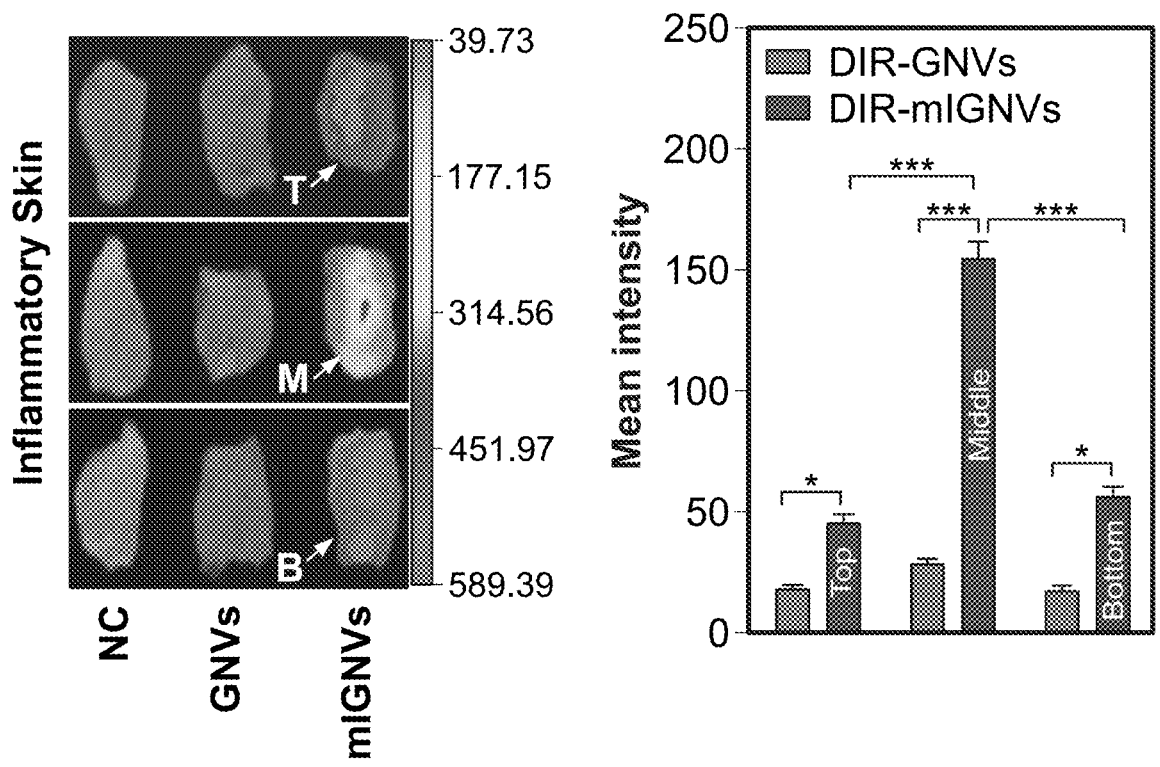
Figure 4E:
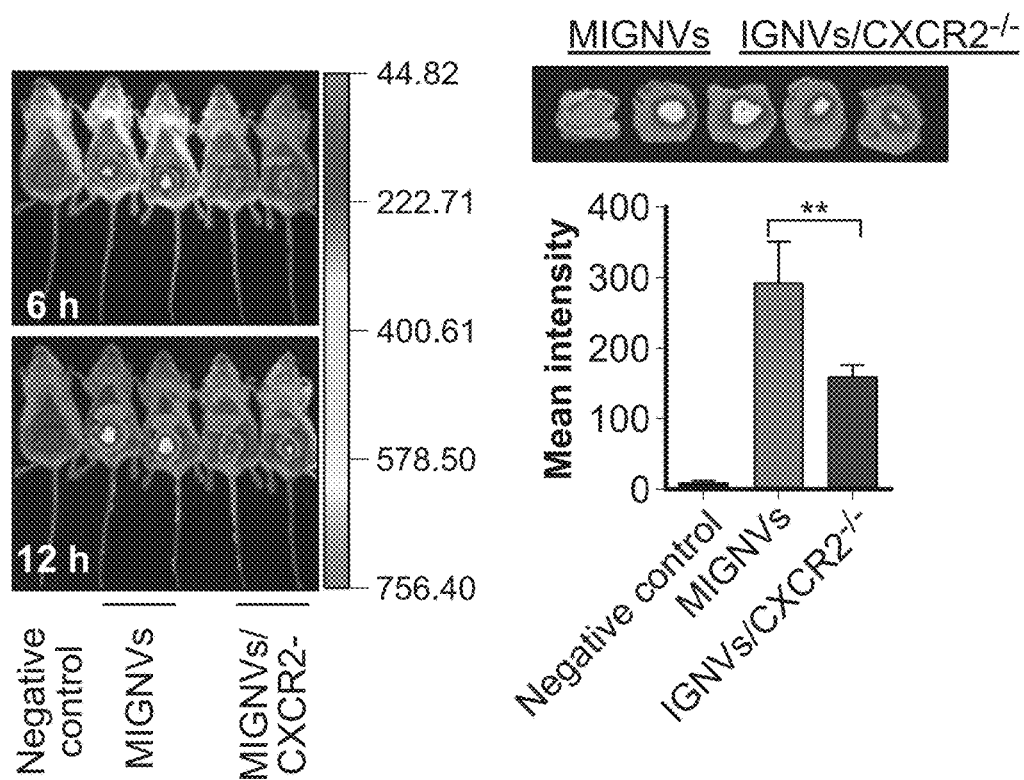
Figure 13B:
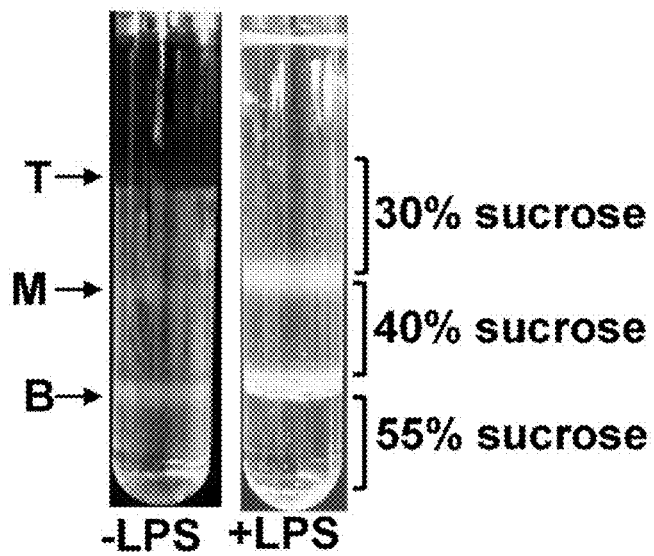
Figure 14:
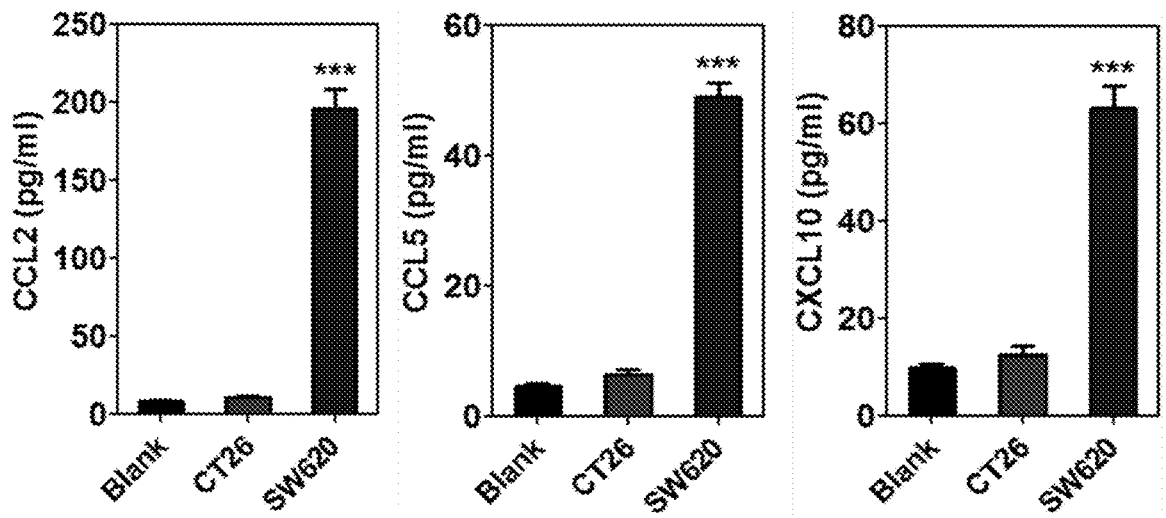
FIG. 14 includes graphs showing chemokines in the culture medium of human SW620 cells, where human colorectal adenocarcinoma SW620 cells were cultured in 6-well plates for 48 h and CCL2, CCL5 and CXCL10 chemokine release into the culture supernatants was quantitatively analyzed with an ELISA.
Figure 15A:
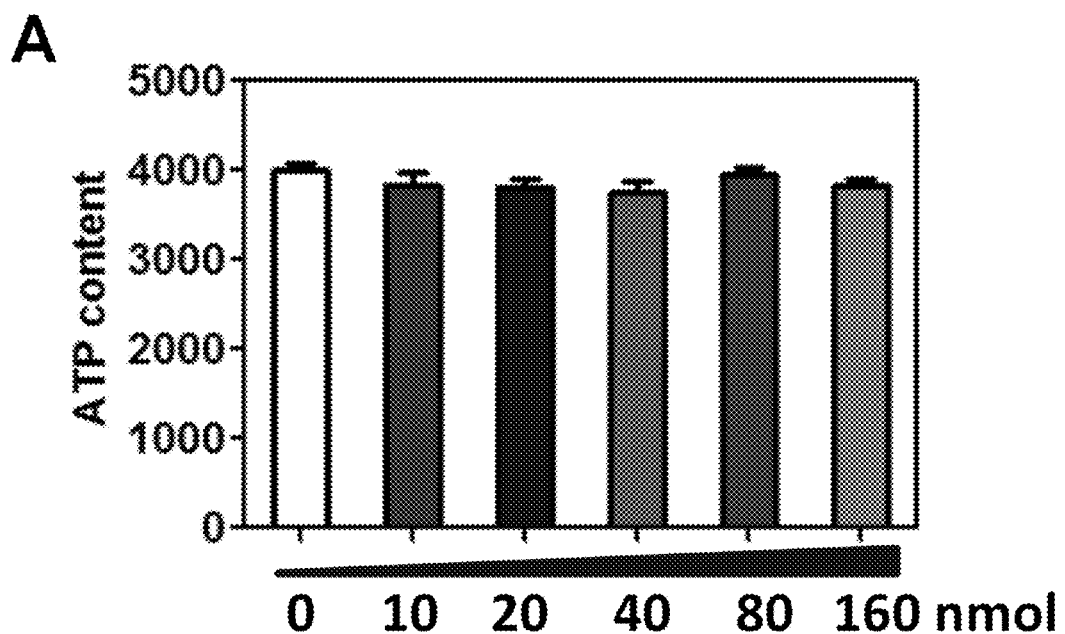
FIGS. 15A-15F include images and graphs showing the effects of IGNVs on cell proliferation in vitro and potential toxicity in vivo.
Figure 15B:
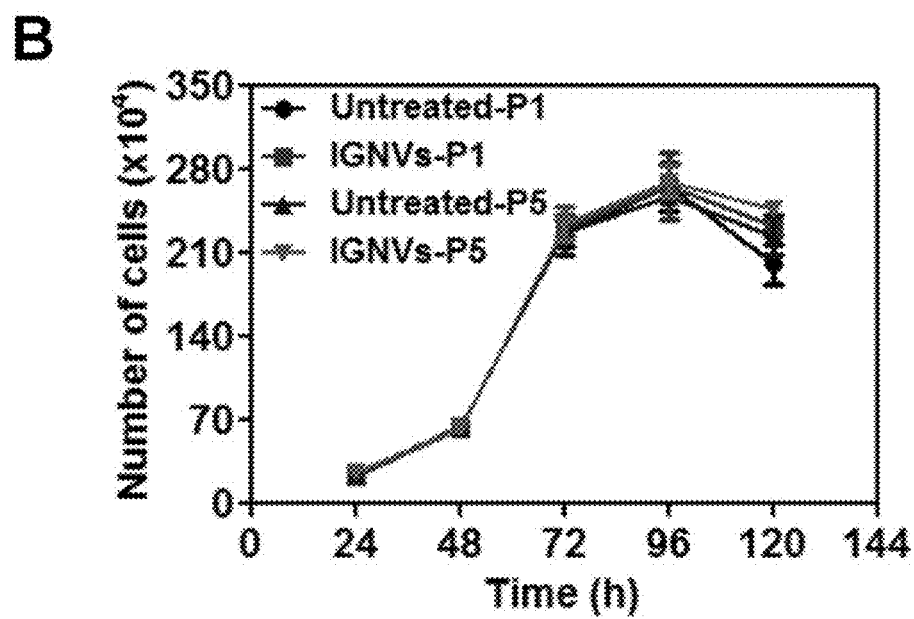
Figure 15C:
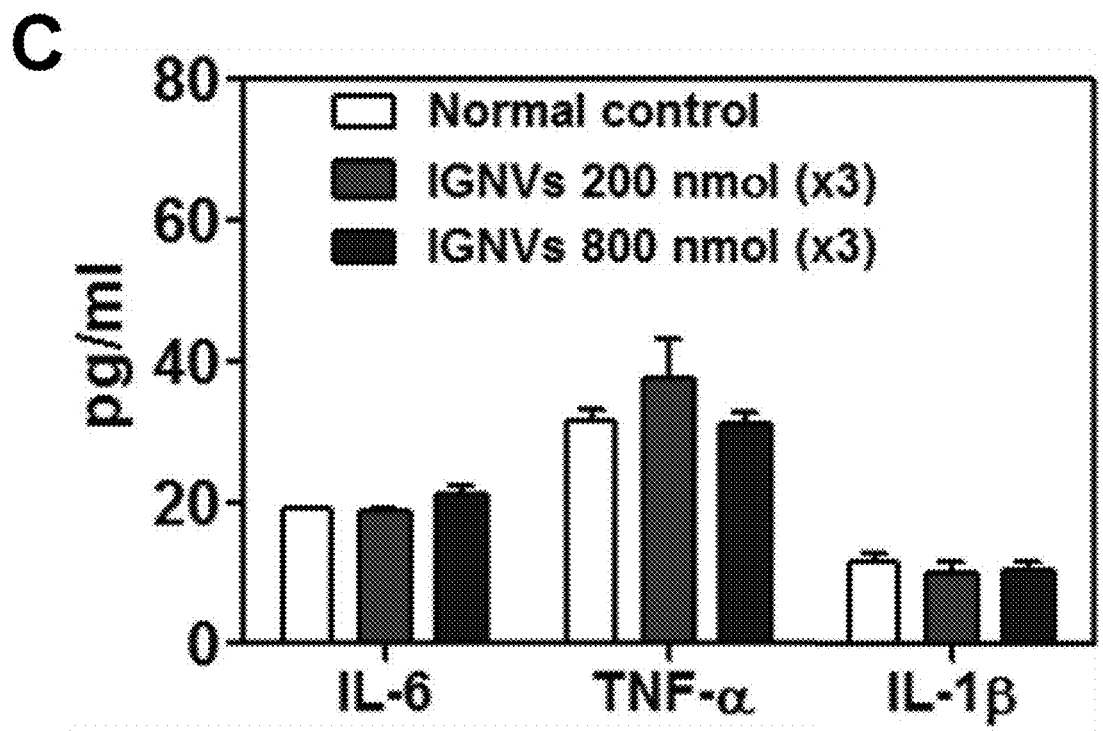
Figure 15D:
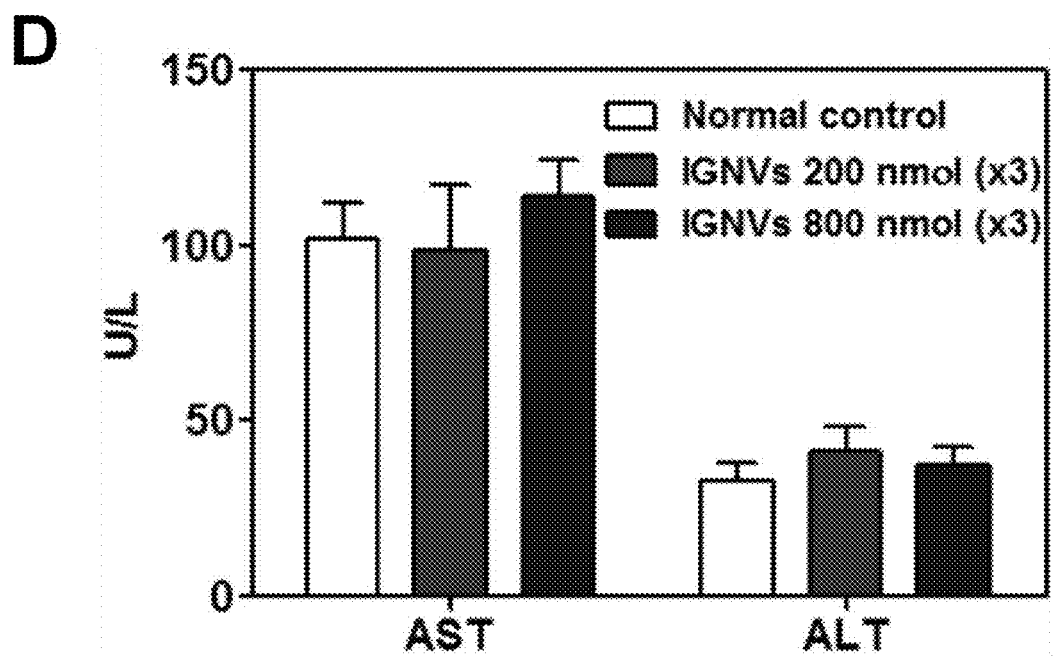
Figure 15E:
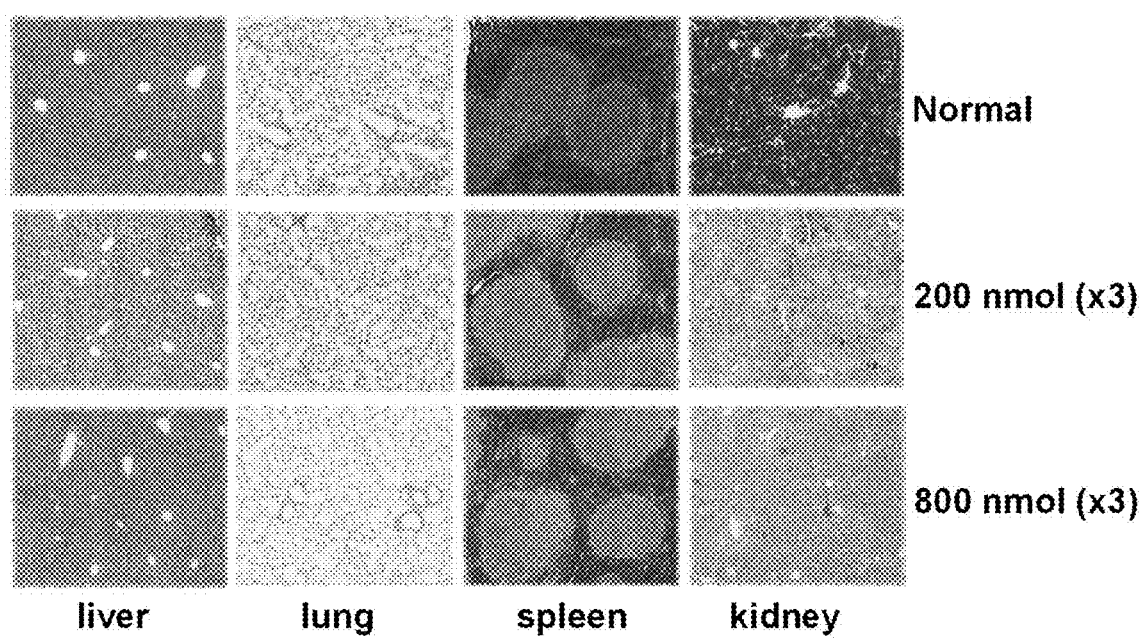
Figure 15F:
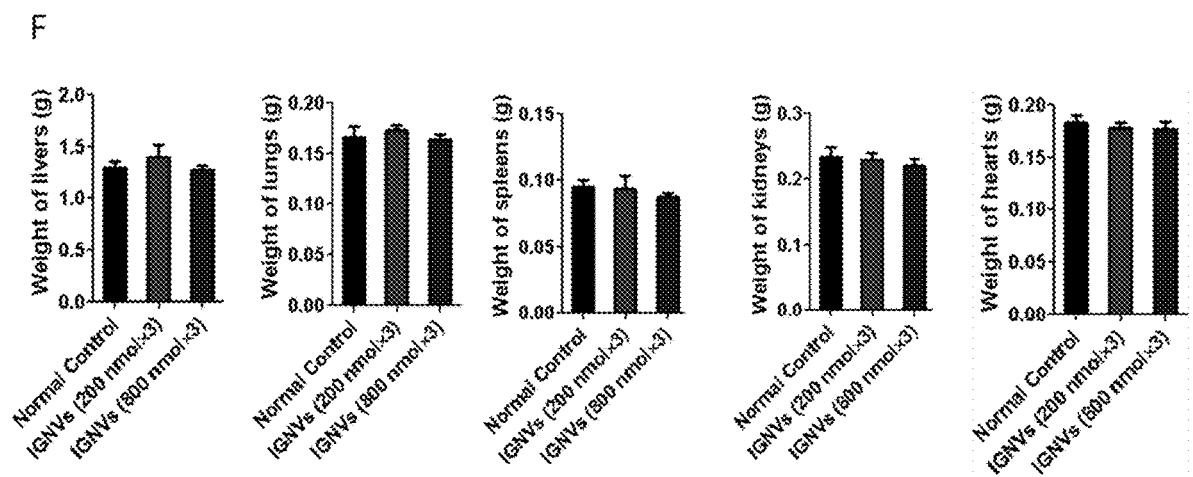

To further demonstrate whether the above-described approach could be applied for treatment of patients in a personalized manner, GNVs coated with the membrane of LPS stimulated leukocytes isolated from the peripheral blood of healthy human subjects (FIG. 13A) or of mice (FIG. 13B) were purified using a sucrose gradient. The chemokine receptors on the IGNVs were quantitatively analyzed (FIGS. 4A-4B). It was then determined whether IGNVs were capable of homing to human tumor using the human colon SW620 tumor model since the chemokines of interest are overexpressed in human colon cancer, as well as breast tumor tissue, and are also released from SW620 colon cancer cells (FIG. 14). The results from in vivo imaging analysis indicated that human SW620 tumor bearing mice (FIG. 4C, **$p<0.01$) or mice locally challenged with LPS (FIG. 4D, *$p<0.05$ and ***$p<0.001$) attracted more IGNVs than GNVs, and IGNVs coated with purified membranes of LPS stimulated leukocytes have the highest fluorescent intensity at day 5 after I.V. injection. The results from an in vitro transwell assay (FIG. 3C) prompted a further determination of whether CXCR2 plays a dominant role in IGNV homing to the inflammatory site. The results generated from in vivo imaging analysis indicated that IGNVs coated with the membrane of LPS stimulated leukocytes isolated from the peripheral blood of CXCR2 knockout mice had significantly attenuated the migration of IGNVs to the inflammatory site (FIG. 4E), suggesting that IGNV CXCR2 plays a key role in IGNV homing.

Example 4

In Vivo Therapeutic Effects of Drugs Carried by IGNVs

Figure 5A:
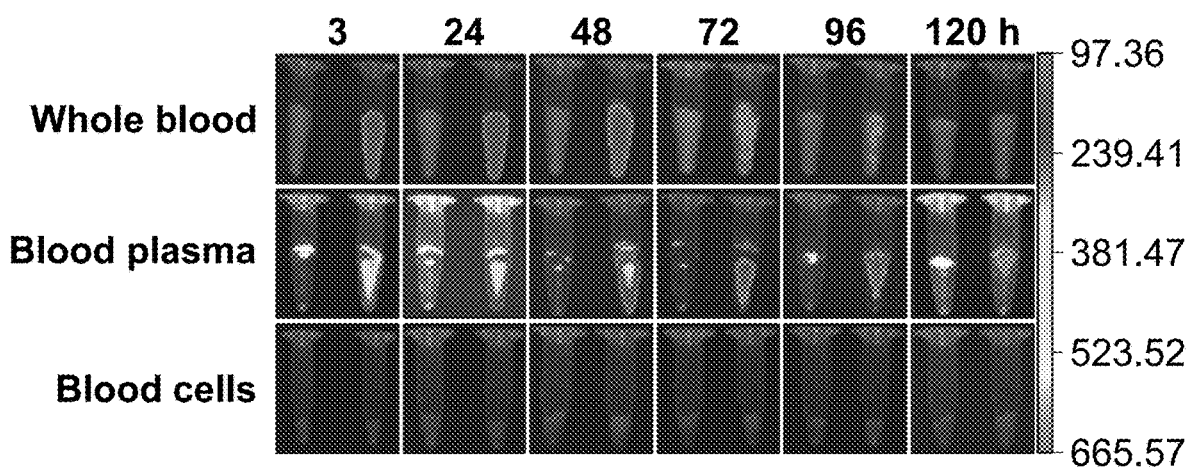
FIGS. 5A-5F includes graphs and images showing targeted therapeutic drug delivery for mouse cancer and colitis therapy.
Figure 5B:
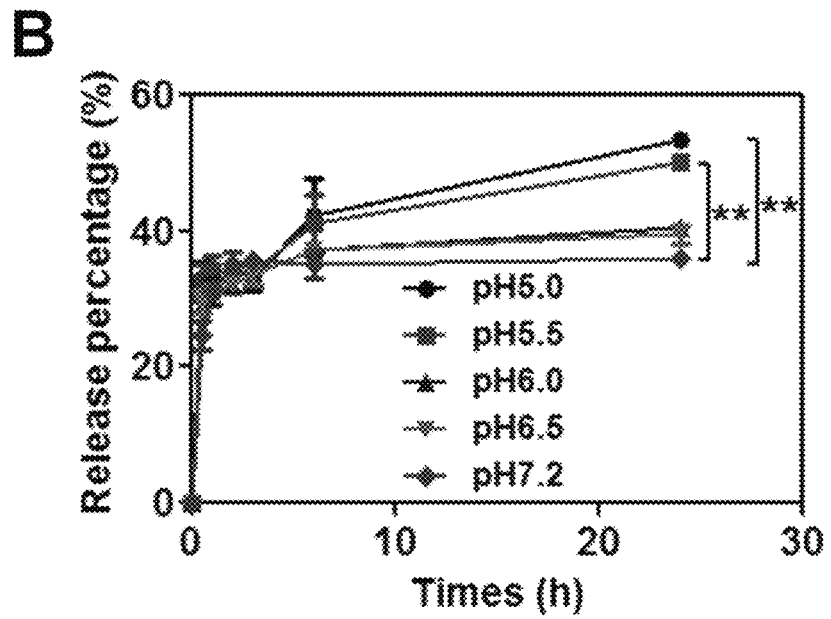
Figure 5C:
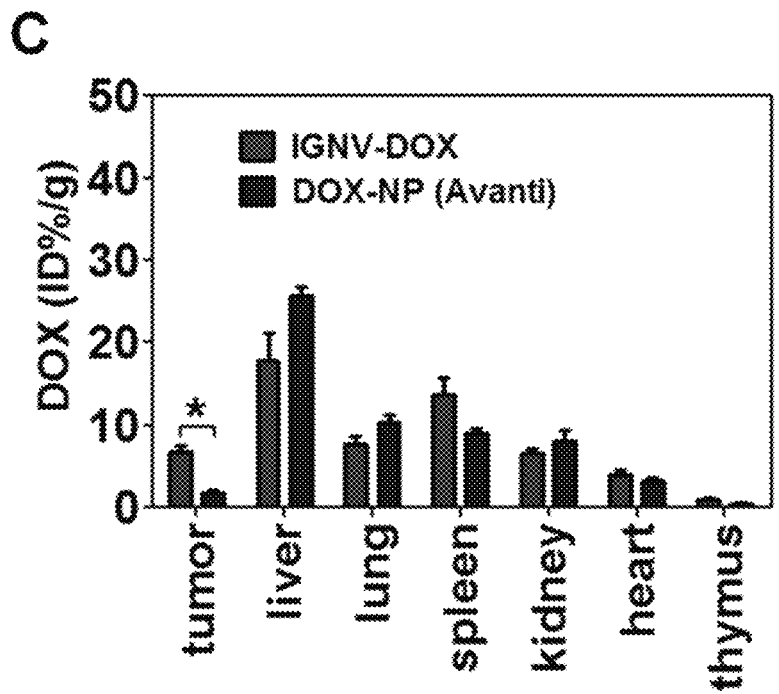
Figure 5D:
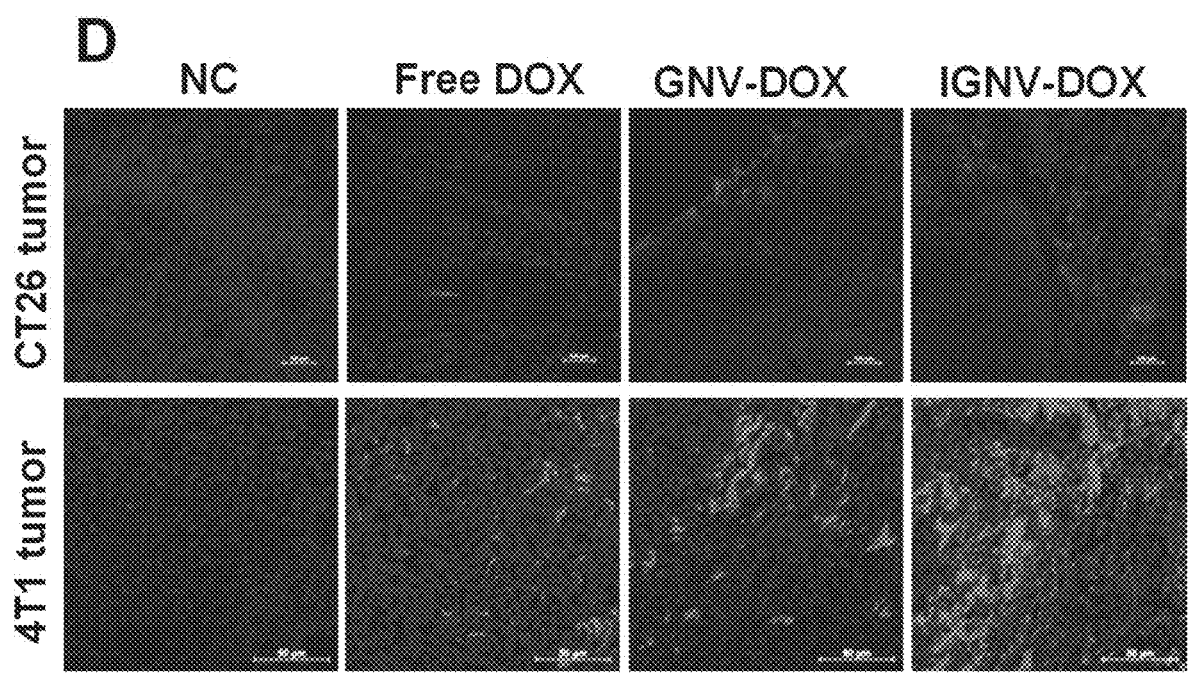
Figure 5E:
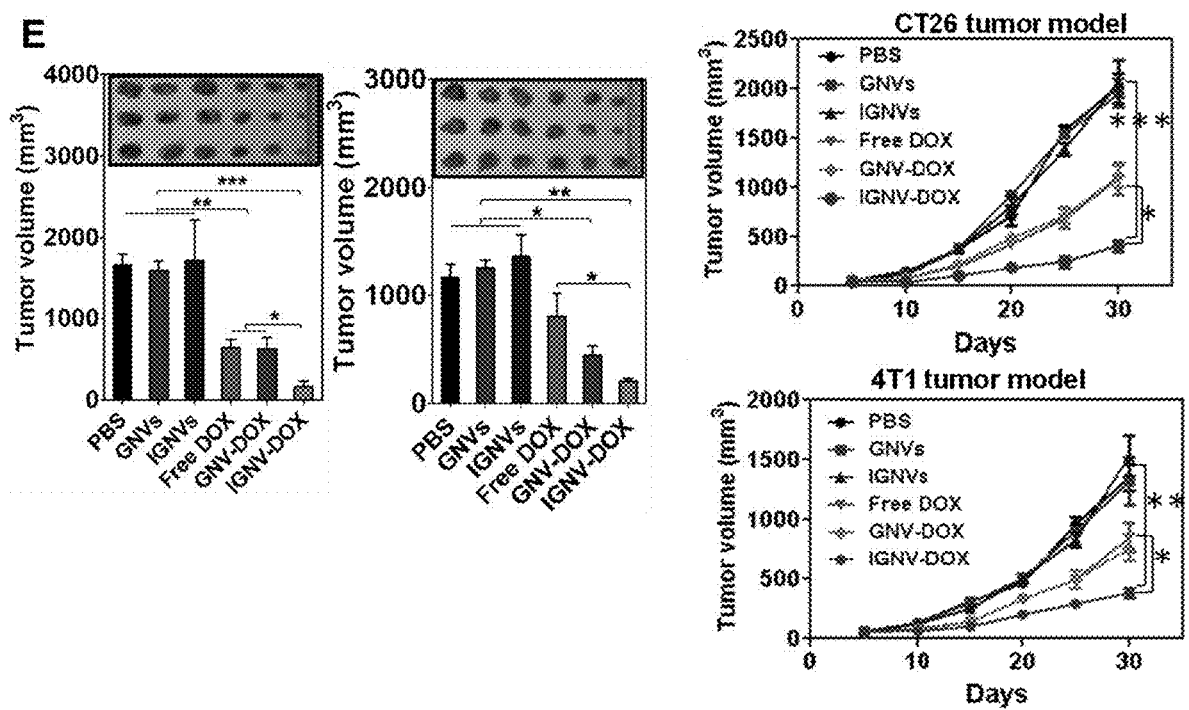
Figure 5F:
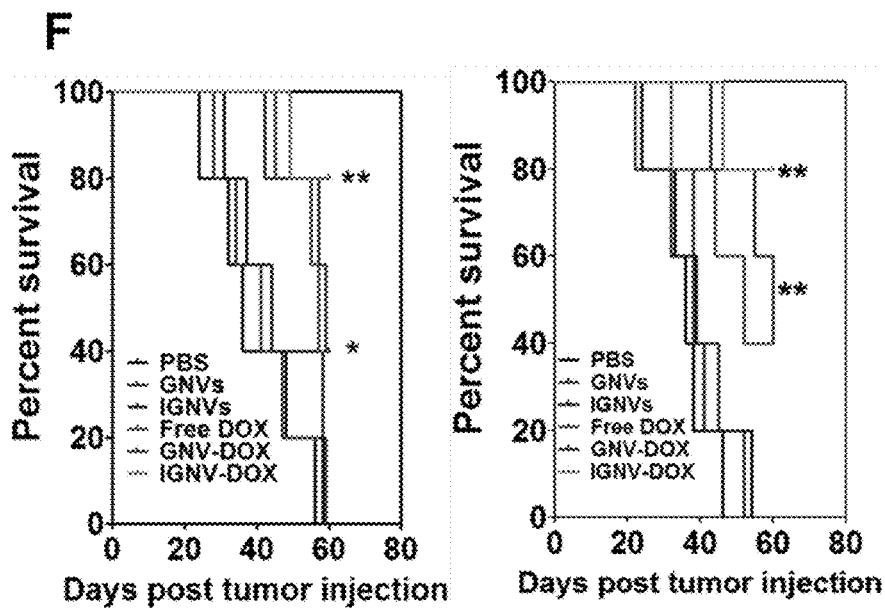
Figure 16A:
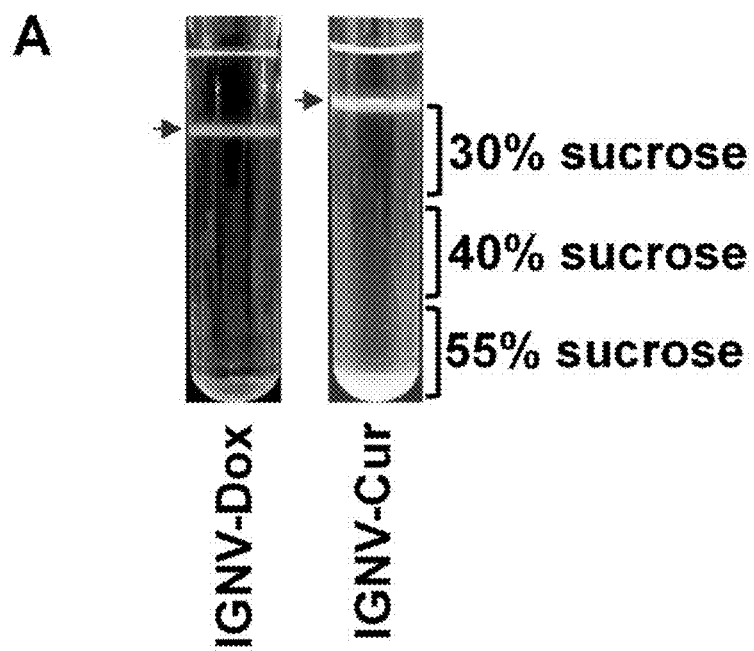
FIGS. 16A-16E include images and graphs showing therapeutic drug-loaded IGNVs.
Figure 16B:
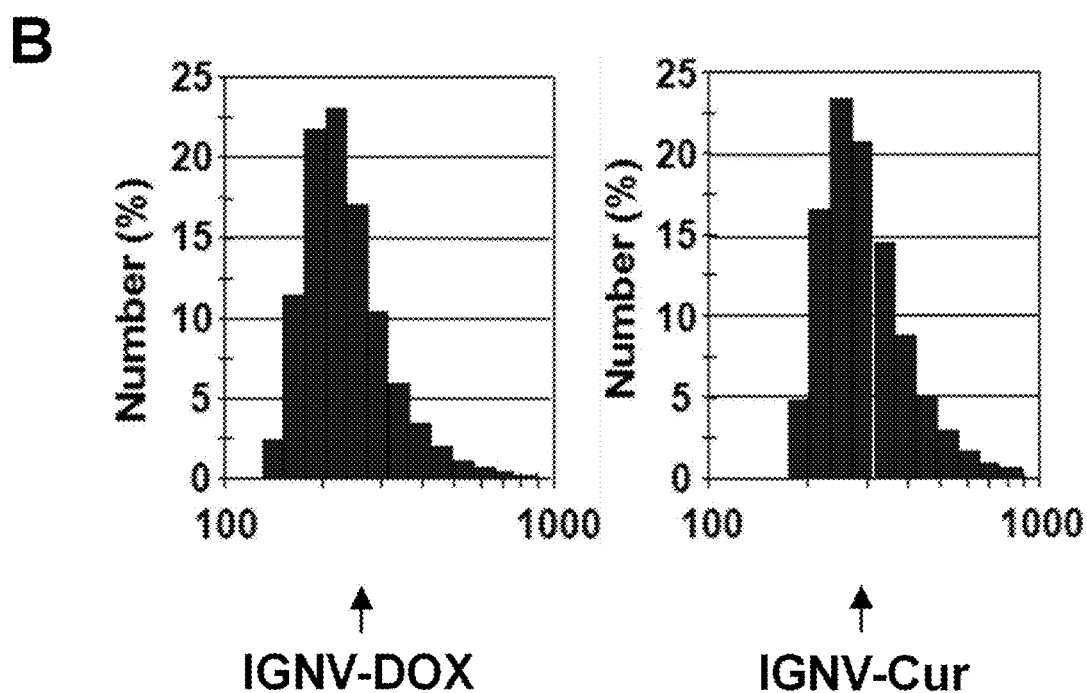
Figure 16C:
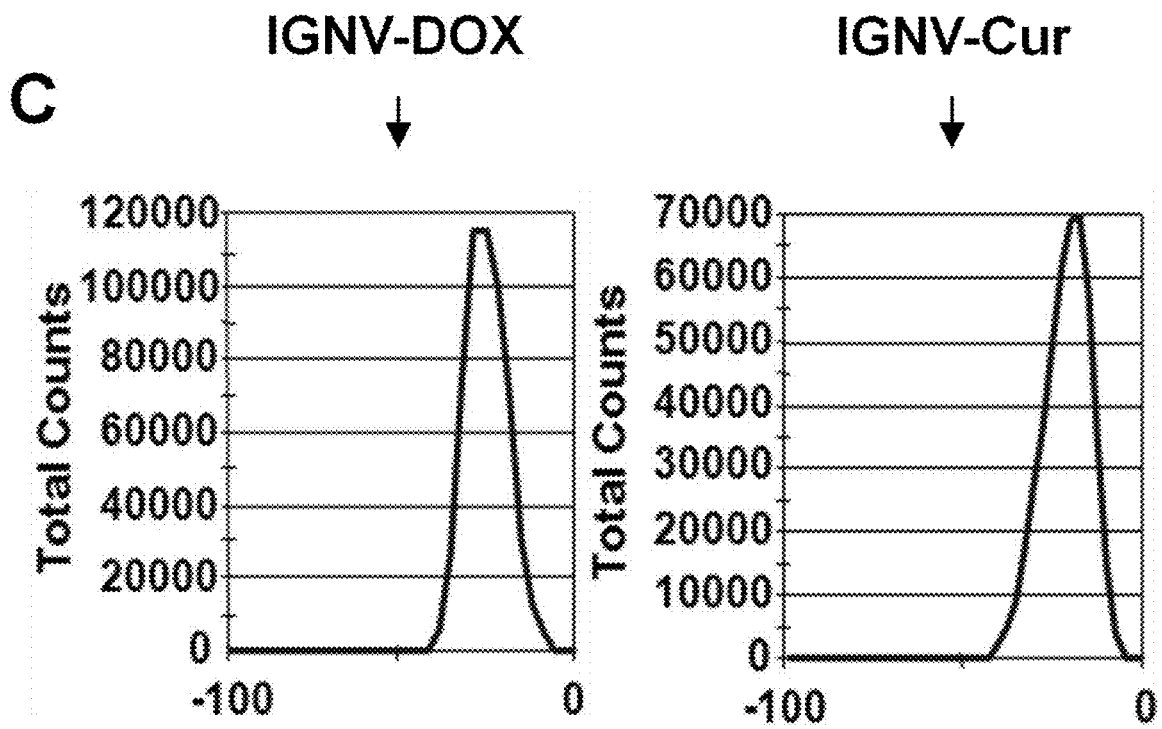
Figure 16D:
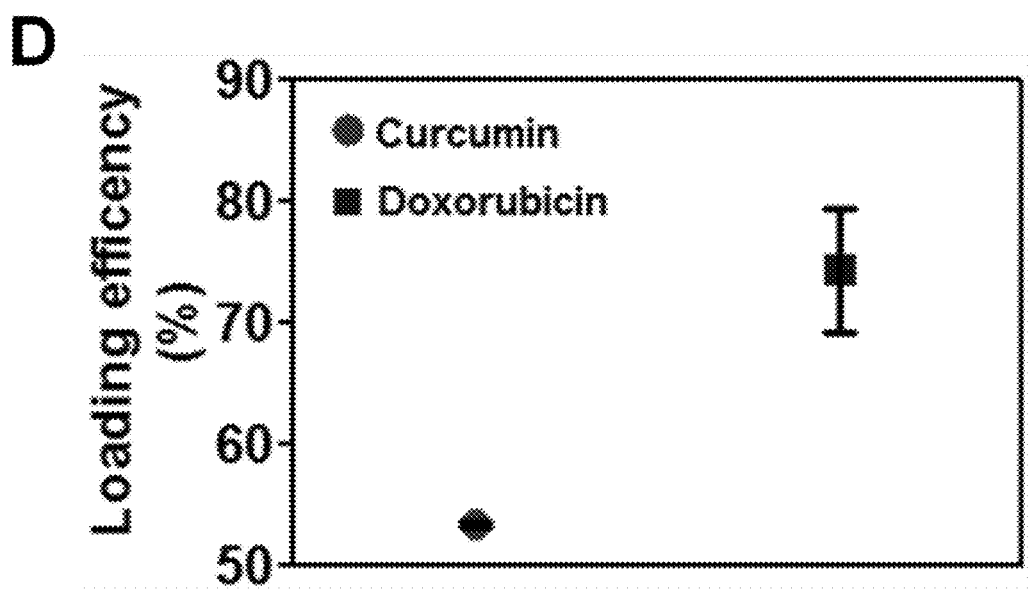
Figure 16E:
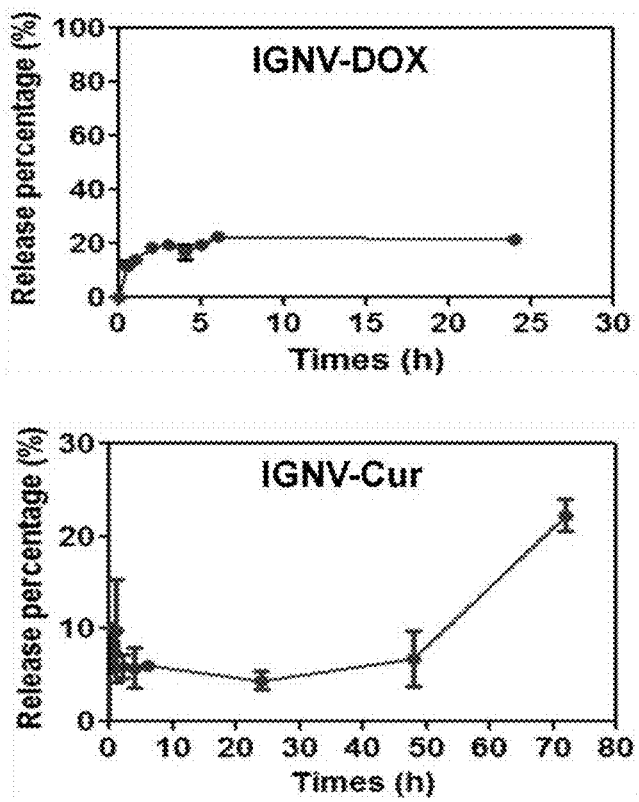
Figure 17A:
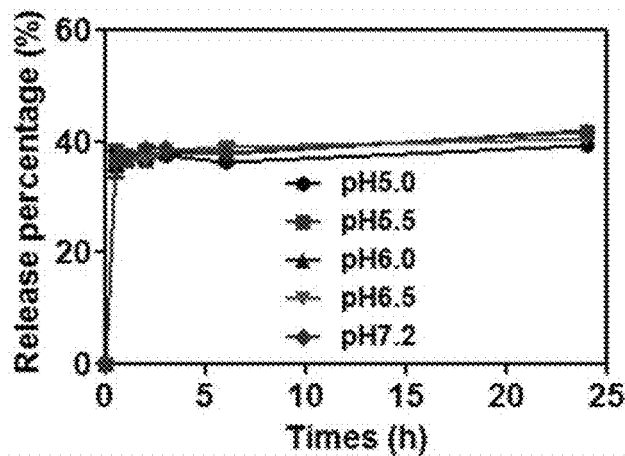
FIGS. 17A-17D include graphs showing the characterization of DOX-NP™ and control liposomes from Avanti.
Figure 17B:
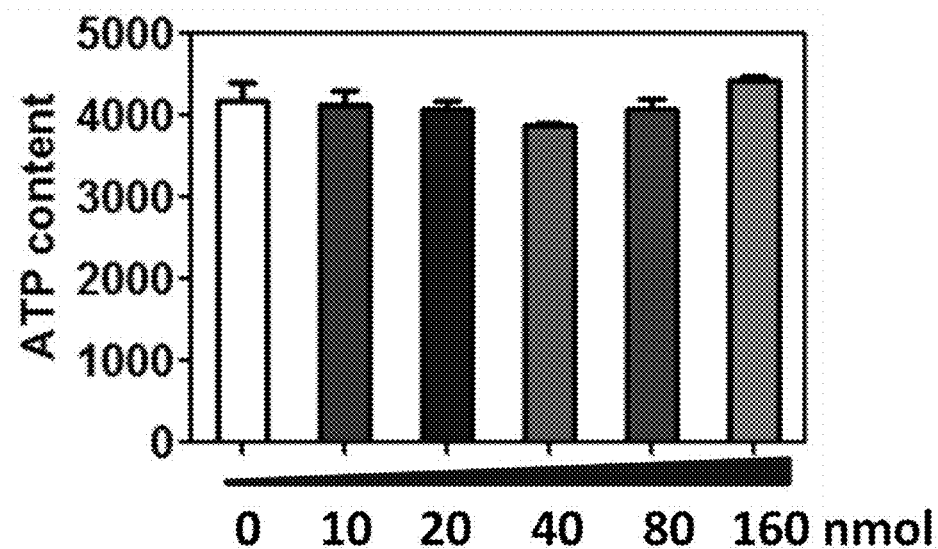
Figure 17C:
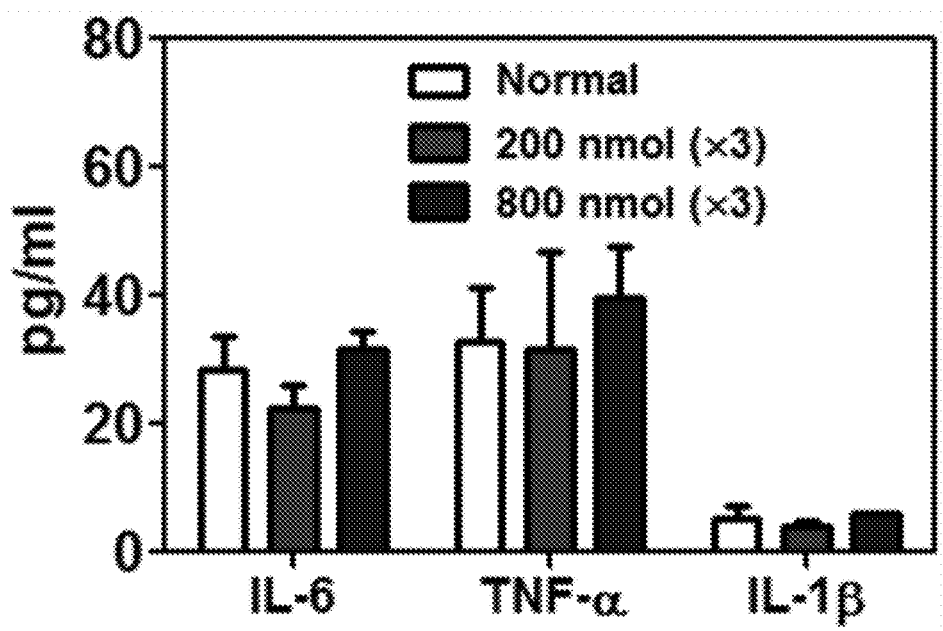
Figure 17D:
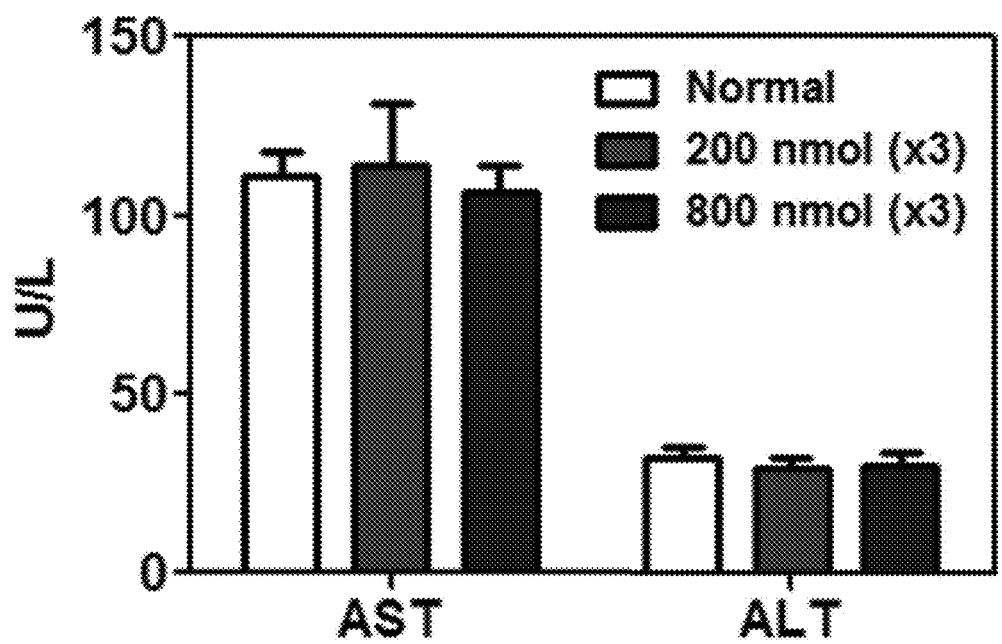
Figure 18:
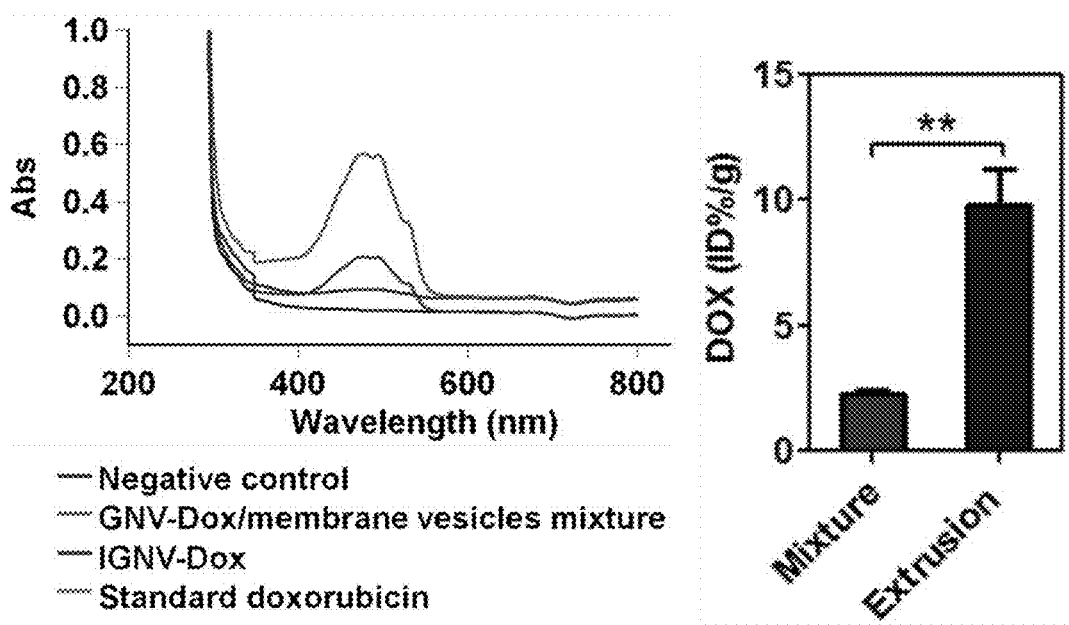
FIG. 18 includes graphs showing the biodistribution of DOX in 4T1 tumor tissues, where DOX (200 μg) was loaded in the GNVs (GNV-DOX), then GNV-DOX was mixed or extruded with ET4 T cell derived membranes (IGNV-DOX), where, after washing, the GNV-DOX or IGNV-DOX were I.V. injected into 4T1 tumor-bearing mice, and where 24 hours later, mice were sacrificed, tumor tissues were removed and the DOX in tumor tissues were extracted and detected.
Figure 19A:
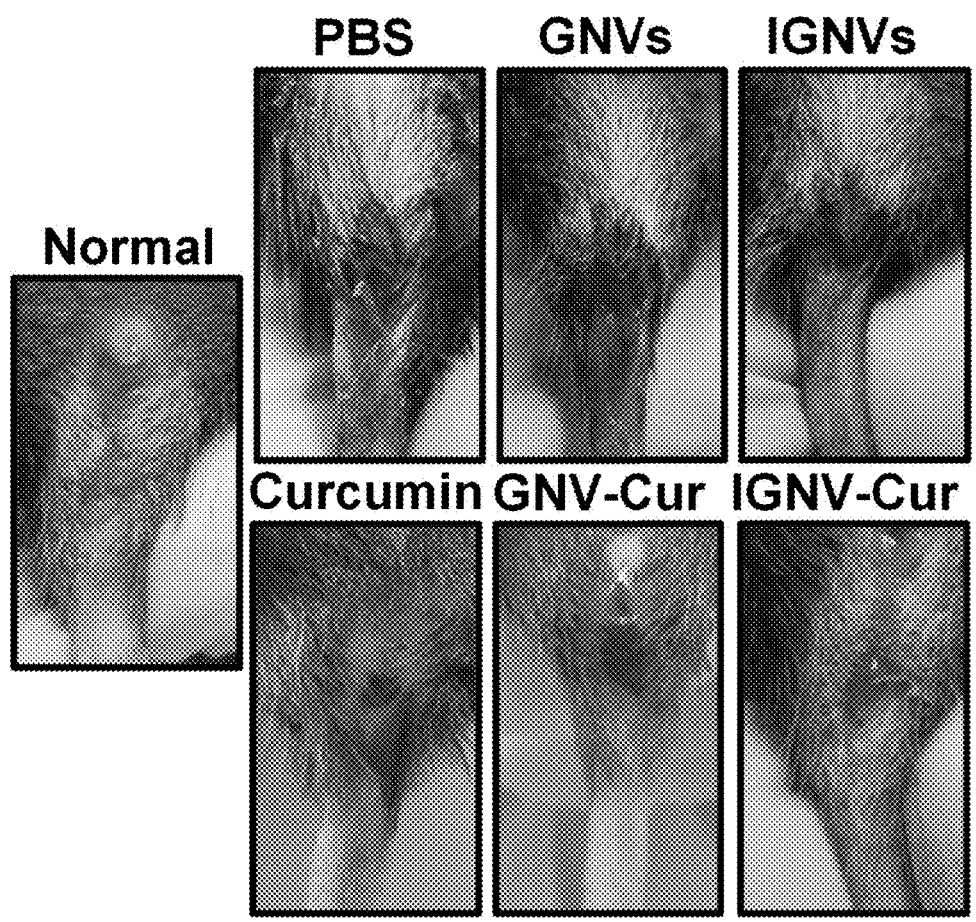
FIGS. 19A-19E include images and graphs showing the therapeutic effect of IGNV-Cur on the inhibition of DSS-induced mouse colitis, where DSS-induced colitis mice were I.V. injected with PBS, GNVs, IGNVs, free curcumin, GNV-Cur or IGNV-Cur every 2 days for 10 days, where at day 0 after the last treatment, the degree of rectal prolapse and intestinal bleeding was determined (FIG. 19A), body weight was measured daily (FIG. 19B), survival rates were analyzed (FIG. 19C), sectioned colon tissues were H&E stained (n=5) (FIG. 19D), and curcumin in colon tissues was quantified by HPLC (FIG. 19E).
Figure 19B:
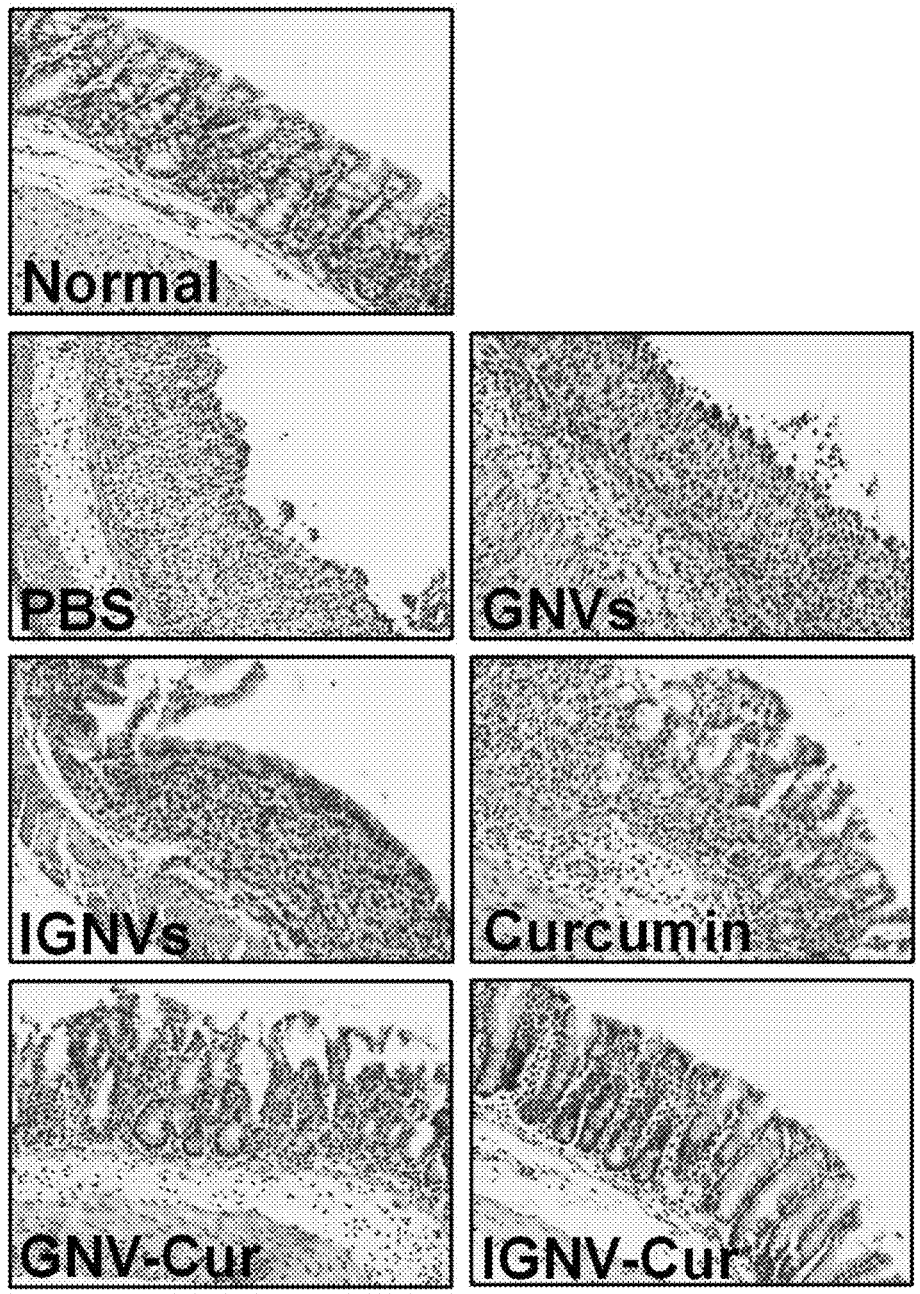
Figure 19C:
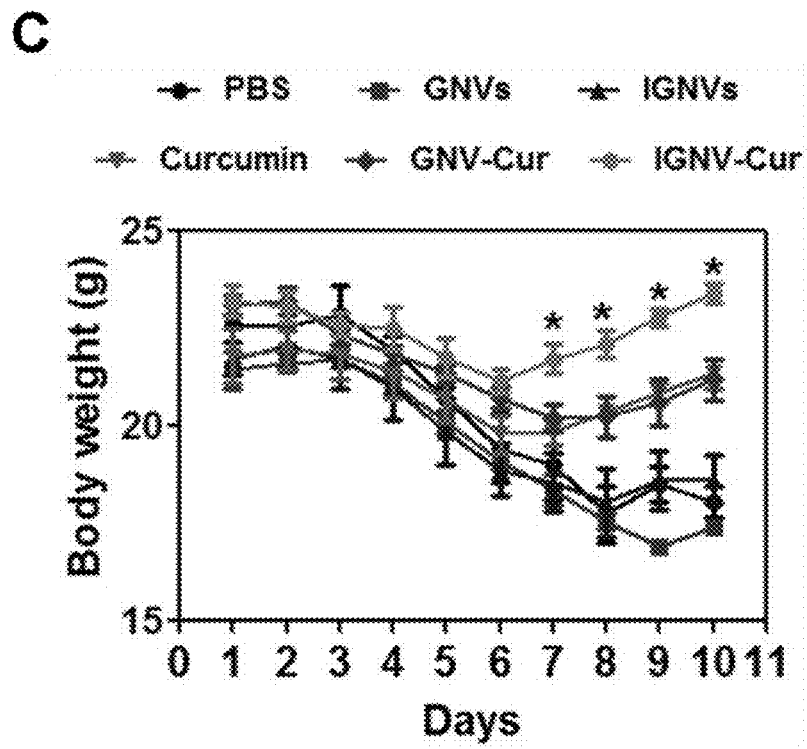
Figure 19D:
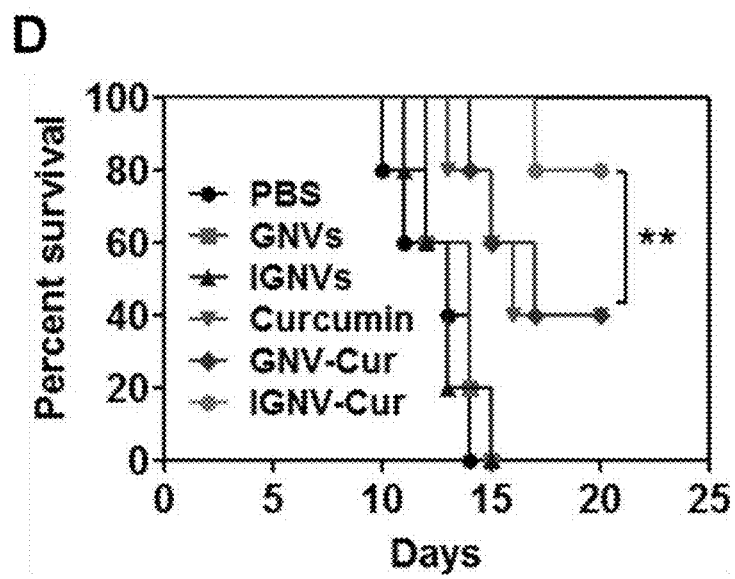
Figure 19E:
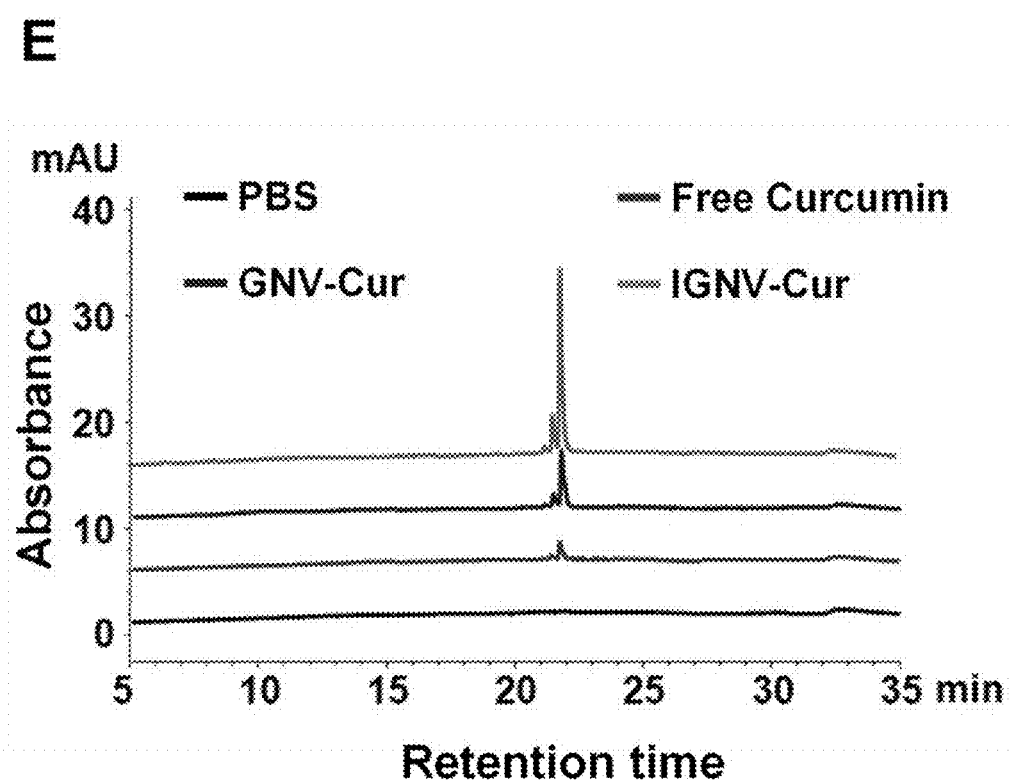
Figure 20:
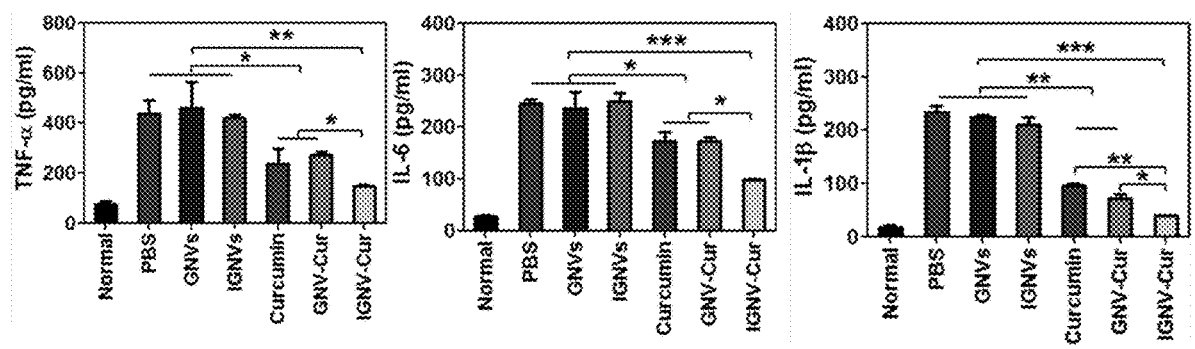
FIG. 20 includes graphs showing the therapeutic effect of IGNV-Cur on the inhibition of cytokine induction from colitis tissue, where, day 3 after being provided with 2.5% DSS, mice (n=5 mice per group) were I.V. injected with PBS, free GNVs (200 nmol), IGNVs (200 nmol), free Cur (50 mg/kg), GNV-Cur (50 mg/kg) or IGNV-Cur (50 mg/kg), every 2 days for 5 times, and where 24 h after the last injection, serum TNF-$\alpha$, IL-6 and IL-1$\beta$ were determined by ELISA.

Since no adverse side effects had been observed with an I.V. injection of IGNVs (FIGS. 15A-15F), it was tested whether IGNVs can be used as a therapeutic drug delivery vehicle. IGNVs are capable of being loaded with different drugs including chemo drugs, such as doxorubicin, and anti-inflammatory agents like curcumin (FIG. 16A). Both doxorubicin and curcumin loaded IGNVs have a similar Zeta potential and size distribution (FIG. 16B, 16C) although the loading capacity (FIG. 16D) and releasing of an agent (FIG. 16E) is different for different types of agents. Further analysis of the stability of IGNVs indicated that circulating IGNVs were stable and detectable until day 5 (FIG. 5A) after an I.V. injection, which in turn provides a longer time span for IGNVs to home to where inflammation is occurring. In addition, IGNV-DOX were stable without releasing doxorubicin until they were in a pH of 5.5 (FIG. 5B, **$p<0.01$) which is the pH in tumor tissue. In contrast, a pH as low as 5.0 did not result in the release of doxorubicin from commercially available doxorubicin loaded liposomes (FIG. 17A), although there were no differences observed in the cell cytotoxicity (FIG. 17B), in vivo induction of pro-inflammatory cytokines (FIG. 17C), and the release of liver enzymes (FIG. 17D) between. IGNVs (FIG. 14) and control liposomes. The tissue distribution of doxorubicin encapsulated into IGNVs was determined next. The concentration of doxorubicin was higher in the tumor and lower in the liver of tumor bearing mice I.V. injected with IGNV-DOX when compared with DOX-NP™ treated mice (FIG. 5C, *$p<0.05$). This result was further confirmed by the much stronger intensity of doxorubicin signals detected in the CT26 tumor as well as 4T1 breast tumor bearing mice I.V. injected with IGNV-DOX when compared to mice treated with GNV-DOX or free doxorubicin (FIG. 5D). Injection of GNV-DOX mixed with EL4 cell derived membrane vesicles had significantly lower levels of doxorubicin detected in the 4T1 tumor than IGNV-DOX (FIG. 18), suggesting that the extrusion of GNVs with the activated leukocyte membranes, which leads to formation of IGNVs, is required for higher efficiency delivery of DOX to inflammatory sites. The biological effects of IGNV-DOX on the CT26 colon tumor and 4T1 breast tumor models were also significant when compared to the other treatments. IGNV-DOX treatment led to significant inhibition in the growth of CT26 and 4T1 tumor (FIG. 5E, *$p<0.05$, $p<0.01$ and *$p<0.001$) and extended the survival of tumor-hearing mice (FIG. 5F, *$p<0.05$, **$p<0.01$). The results from IGNV-Cur treatment of DSS induced mouse colitis also indicated that IGNVs carrying curcumin has a better therapeutic effect on the inhibition of colitis than GNVs carrying curcumin or curcumin alone. This conclusion is supported by the fact that there was less blood in stools (FIG. 19A), fewer leukocytes were observed infiltrating HE stained mouse colon tissue (FIG. 19B), there was less lost weight (FIG. 19C) and there was a significantly improved survival rate (FIG. 19D) in DSS induced colitis mice I.V. injected with IGNV-Cur than control groups as listed. These results were also consistent with higher concentration of curcumin detected in the colon tissues of mice treated with IGNV-Cur (FIG. 19E). ELISA analysis further indicated that significantly less TNF-α, IL-6 and IL-1β were detected in the colon tissue extracts of DSS induced colitis mice I.V. injected with IGNV-Cur than with PBS/DSS, free Cur, or GNV-Cur (FIG. 20).

Discussion of Examples 1-4

The foregoing study describes an approach for targeted delivery of therapeutic agents to inflammatory sites where the appropriate cells are targeted; thereby promoting much more substantial therapeutic benefits without inducing adverse side-effects. It was shown that IGNVs can be an effective, personalized approach to potentially treat patients with a variety of inflammatory conditions. The use of IGNVs avoids several of the problems that have arisen with conventional therapy vectors, such as the lack of tissue targeting specificity, immunogenicity, difficulty in scalability and production, the need for life-long monitoring for tumorigenesis and other adverse clinical outcomes. Because IGNVs do not cause these concerns they have great potential as targeted delivery vehicles, in particular, because production of GNVs is easily scaled up and the GNVs can be coated with leukocyte membranes from an individual making this approach personalized and economically feasible for treatment of patients in low and middle income countries where they do not have comprehensive facilities to make synthetic therapeutic vectors.

Figure 21:
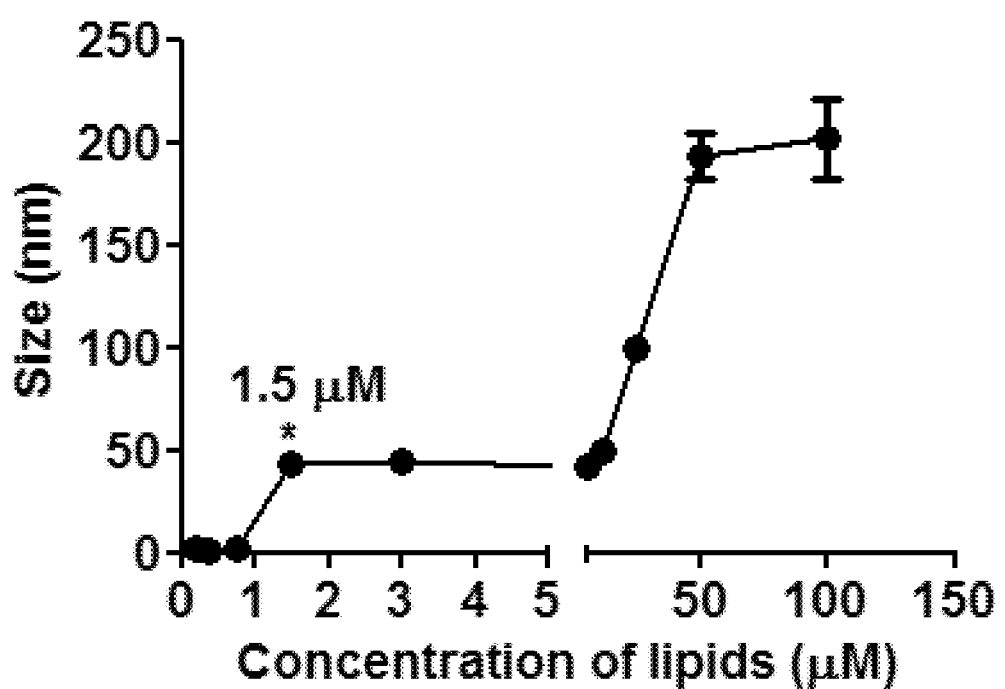
FIG. 21 is a graph showing the determination of GNV miceller concentration. (cmc), where different concentrations of total lipids (X-axis) extracted from grapefruit nanoparticles were used for generating lipid film, and where, after a bath-sonication, the formation and size distribution of GNV (nm) was analyzed using a ZetaSizer.

To successfully target a specific tissue, four goals must at least be met: 1) extended circulation of the delivery vector. 2) tissue penetration by the vector, 3) tissue specificity and 4) release of the payload, i.e., the therapeutic agent. Tumor tissues have abnormal molecular and fluid transport dynamics, especially for macromolecular drugs. This phenomenon is referred to as the "enhanced permeability and retention (EPR) effect" of macromolecules and lipids in solid tumors. Therefore, the longer the vector is in the circulation, the greater opportunity it has to penetrate the tumor tissue by utilizing the EPR effect. Previously published work shows that a nanovector made of lipids from grapefruit nanoparticles circulates in the peripheral blood more than 5 days in tumor bearing mice. GNVs are stable in the circulatory system and thus have a greater opportunity to enter the tumor tissue. In addition, the critical concentration of grapefruit nanoparticle derived lipids for GNV formation was 1.5 µM (FIG. 21), and GNVs do not increase in size with increasing concentrations of total lipids up to 5 mM. The diameter of GNVs at 25 mM-50 mM concentration and at 25° C. is increased up to 200 nm, and retained at 200 nm while lipid concentration was further increased up to 100 mM. It was believed that this finding not only provides a guideline for selecting concentrations of grapefruit nanoparticle derived lipids to make desirable sized GNVs (50-200 nm) but also a broad range of concentrations of grapefruit nanoparticle derived lipids can be selected for making GNVs without leading to a further increase of GNV size. The latter feature has an advantage in case that a large amount of grapefruit nanoparticle derived lipids is required to make GNVs which allows for higher concentrations of therapeutic agents to be encapsulated per GNV. However, this feature of GNVs alone may not be sufficient to deliver ample agent to the targeted tissue to have a therapeutic effect. Achieving specific and safe delivery of a drug across endothelial cells is essential if it is to reach the targeted tissue. However, due to the fact that most delivery vectors lack an affinity for endothelium, only a small fraction of therapeutics can be delivered to the targeted tissue by utilizing the EPR effect. In the foregoing study, IGNVs were modified so they could take advantage of the activated leukocyte pathway that is primarily driven by chemokines/chemokine receptors by coating the IGNVs with the membranes from activated leukocytes. This modification of IGNVs significantly enhanced their endothelial cell transmigration capability so the IGNVs could enter inflammatory tissues. As was demonstrated in this study, not only can this strategy be applied to breast cancer and colon cancer, but the potential exists that the IGNVs could be used to treat many different types of diseases since the inflammatory process is a hallmark of many chronic diseases including cancer, infectious diseases, and autoimmune diseases. As shown in this study, the chemotherapy drug doxorubicin and the anti-inflammatory agent curcumin can be delivered successfully by IGNVs to reach the desired inflammatory site and achieve a therapeutic effect through modification of GNVs with membranes of activated leukocytes from individuals. Specifically, it was demonstrated that I.V. injection of IGNV-DOX or IGNV-Cur significantly enhances the inhibition of breast tumor and colon tumor growth, and attenuates DSS induced colitis, respectively. This response was due to improved recruitment of IGNVs into tumor as well as inflamed colon tissue. The membranes from activated leukocytes were required to obtain this benefit, as it permitted IGNV delivery to the precise place where inflammation is occurring.

It was also thought that other factors in addition to chemokines/chemokine receptors may play a role in IGNVs homing to an inflammatory site. Previous studies have suggested that LFA-1 plays a role in the nanoparticle homing to an inflamed site. The present studies used LFA-1 (CD11a-CD18) as an example, and the foregoing data also showed that CXCR2 and LFA-1 played a role in the transmigration of IGNVs as demonstrated in an in vitro trans-well blocking assay and in vivo skin inflammatory mouse model. Therefore, the role of IGNV chemokine receptors as demonstrated in this study does not exclude a number of other IGNV factors such as CXCR2 and LFA-1 which also plays a role in the process of IGNV recruitment into inflamed tissue. This is also a reason that it was believed IGNVs coated with total leukocyte membranes may have a greater potential for being applied to personalized medicine for targeted delivery to inflammatory sites than the use of individual chemokine receptor coated IGNVs. It was further conceivable that membrane associated chemokine and integrin profiles of circulating inflammatory cells from patients with different chronic inflammatory diseases may be different in their makeup. Furthermore, individual chemokine receptor coated GNVs may be potentially difficult to optimize in combinations or as a customized set or group of chemokine receptors that are most suitable for targeted delivery for an individual patient. Additionally there may be a higher cost for production of recombinant chemokine receptors and recombinant production would require FDA approval for clinical use. Finally, potential biosafety issues could arise due to using synthesized recombinant chemokine receptors.

A suitable delivery vehicle should be susceptible to manipulation so delivered therapeutic drug can be released within targeted tissue. Evidence accumulated over the past decades has shown that the ptI in electrode-evaluated human tumor is on average lower than the pH of normal tissues. The results presented in the foregoing study show that doxorubicin encapsulated in the IGNVs is stable until the pH drops to 6.0 or below. This feature of IGNVs allows the encapsulated drug to selectively be released in tumor tissue, and therefore reduces the side-effects seen when chemotherapy treatment non-discriminately affects healthy organs and tissues, which is one of major obstacles for chemotherapy for treatment of cancer patients.

In the past decades, substantial experimental and clinical evidence supports the conclusion that one of the most important mechanisms operating in tumor progression involves chemokines and their receptors. Chemokines and their receptors not only play a role in cancer-related inflammation, but have been implicated in the invasiveness and metastasis of diverse cancers. Without wishing to be bound by any particular theory, it was believed that pseudo-inflammatory chemokine receptors delivered by GNVs may also act as soluble receptors to block the patlaway(s) mediated by chemokine receptors expressed on the tumor cells or other tumor associated cells.

Throughout this document, various references are mentioned. All such references are incorporated herein by reference, including the references set forth in the following list:

REFERENCES

1. Kugelberg E. T cell responses: kiss and run. Nature reviews Immunology 2014; 14(3):134.
2. Pober J S, Sessa W C. Evolving functions of endothelial cells in inflammation. Nature reviews Immunology 2007; 7(10): 803-15.
3. Schall T J, Proudfoot A E. Overcoming hurdles in developing successful drugs targeting chemokine receptors. Nature reviews Immunology 2011; 11. (5):355-63.
4. Mantovani A, Bonecchi R, Locati M. Tuning inflammation and immunity by chemokine sequestration: decoys and more. Nature reviews Immunology 2006; 6(12):907-18.
5. Ben-Baruch A. Organ selectivity in metastasis: regulation by chemokines and their receptors. Clinical & experimental metastasis 2008; 25(4):345-56.
6. Godessart N. Chemokine receptors: attractive targets for drug discovery. Annals of the New York Academy of Sciences 2005; 1051:647-57.
7. Warnock R A, Campbell J J, Dorf M E, Matsuzawa A, McEvoy L M, Butcher E C. The role of chemokines in the macroenvironmental control of T versus B cell arrest in Peyer's patch high endothelial venules. The Journal of experimental medicine 2000; 191(1):77-88.
8. Weber M, Uguccioni M, Baggiolini M, Clark-Lewis I, Dahinden C A. Deletion of the NH2-terminal residue converts monocyte chemotactic protein 1 from an activator of basophil mediator release to an cosinophil chemoattractant. The Journal of experimental medicine 1996; 183(2):681-5.
9. O'Hayre M, Salanga C L, Handel T M, Hamel D J. Emerging concepts and approaches for chemokine-receptor drug discovery. Expert opinion on drug discovery 2010; 5(11):1109-22.
10. Parodi A, Quattrocchi N, van de Ven A L, Chiappini C, Evangelopoulos M, Martinez J O, et al. Synthetic nanoparticles functionalized with biomimetic leukocyte membranes possess cell-like functions. Nature nanotechnology 2013; 8(1): 61-8.
11. Hock S C, ling Y M, Wah C L. A review of the current scientific and regulatory status of na.nomedicines and the challenges ahead. PDA J Pharni Sci Technol 2011; 65(2): 177-95.
12. Juliano R. Nanomedicine: is the wave cresting? Nature reviews Drug discovery 201.3; 12(3):171-2.
13. Zhuang X, Xiang X, Grizzle W, Sun. D. Zhang S, Axtell. R C, et al. Treatment of brain inflammatory diseases by delivering exosome encapsulated anti-inflammatory drugs from the nasal region to the brain. Mol Ther 2011; 19(10):1769-79.
14. Alvarez-Ervin L, Seow Y, Yin H, Betts C, Lakhal S, Wood M J. Delivery of siRNA to the mouse brain by systemic injection of targeted exosomes. Nat Biotechnol 2011; 29(4):341-5.
15. Wang B, Zhuang X, Deng Z B, Jiang H, Mu J, Wang Q, et al. Targeted drug delivery to intestinal macrophages by bioactive nanovesicles released from grapefruit. Molecular therapy: the journal of the American Society of Gene Therapy 2014; 22(3):522-34.
16. Ju S, Mu J, Dokland T, Zhuang X, Wang Q, Jiang H, et al. Grape exosome-like nanoparticles induce intestinal stein cells and protect mice from DSS-induced colitis. Molecular therapy: the journal of the American Society of Gene Therapy 2013; 21(7):1345-57.
17. Mu J, Zhuang X, Wang Q, Jiang H, Deng Z B, Wang B, et al. Interspecies communication between plant and mouse gut host cells through edible plant derived exosome-like nanoparticles. Molecular nutrition & food research 2014.
18. Wang Q, Zhuang X, Mu J, Deng Z B, Jiang H., Zhang L, et al. Delivery of therapeutic agents by nanoparticles made of grapefruit-derived lipids. Nature communications 2013; 4:1867.
19. Maeda H, Wu J, Sawa T, Matsumura Y, Hori K. Tumor vascular permeability and the EPR effect in macromolecular therapeutics: a review. Journal of controlled release: official journal of the Controlled Release Society 2000:65(1-2):271-84.
20. Maeda H, Matsumura Y. Tumoritropic and lymphotropic principles of macromolecular drugs. Critical reviews in therapeutic drug carrier systems 1989; 6(3):193-210.
21. Gerweck L E, Seetharaman K. Cellular pH gradient in tumor versus normal tissue: potential exploitation for the treatment of cancer. Cancer research 1996; 56(6):1194-8.
22. Chen H, Liu X, Dou Y, He B, Liu L, Wei Z, et al. A pH-responsive cyclodextrin-based hybrid nanosystem as a nonviral vector for gene delivery. Biomaterials 2013; 34(16):4159-72.
23. Li. P, Liu D, Miao L, Liu C, Sun X, Liu Y, et al. A pH-sensitive multifunctional gene carrier assembled via layer-by-layer technique for efficient gene delivery. International journal of nanomedicine 2012; 7:925-39.
24. Mok H, Veiseh O, Fang C, Kievit F M, Wang F Y, Park J O, et al. pH-Sensitive siRNA nanovector for targeted gene silencing and cytotoxic effect in cancer cells. Molecular pharmaceutics 2010; 7(6): 1930-9.
25. Reymond N, d'Agua B B, Ridley A J. Crossing the endothelial barrier during metastasis. Nature reviews Cancer 2013; 13(12):858-70.
26. Balkwill F. Cancer and the cliemokine network. Nature reviews Cancer 2004; 4(7):540-50.
27, Lombardi L, Tavano F, Morelli F, Latium T P, Di Sebastian P, Maiello E. Chemokine receptor CXCR4: role in gastrointestinal cancer. Critical reviews in oncology/hematology 2013; 88(3):696-705.
28. Franciszkiewicz K, Boissonnas A, Boutet M, Combadiere C, Mami-Chouaib F. Role of chemokines and chemokine receptors in shaping the effector phase of the antitumor immune response. Cancer research 2012; 72(24):6325-32.
29. Liu C, Yu S, Zinn K, Wang J, Zhang L, Jia Y, et al. Murine mammary carcinoma exosomes promote tumor growth by suppression of NK cell function. Journal of immunology 2006; 176(3):1375-85.
30. Fink A E, Bender K J, Trussell L O, Otis T S, DiGregorio D A. Two-photon compatibility and single/single-voxel, single-trial detection of subthreshold neuronal activity by a two-component optical voltage sensor. PloS one 2012; 7(8):e41434.
31. Bradley J, Luo R, Otis T S, DiGregorio D A. Submillisecond optical reporting of membrane potential in situ using a neuronal tracer dye. The Journal of neuroscience: the official journal of the Society for Neuroscience 2009; 29(29):9197-209.
32. Wang Q, Zhuang X, Mu J, Deng Z B, Jiang H, Zhang L, et al. Delivery of therapeutic agents by nanoparticles made of grapefruit-derived lipids. Nature communications 2013; 4:1867.
33. Song Z, Feng R, Sun M, Guo C, Gao Y, Li L, et al. Curcumin-loaded PLGA-PEG-PLGA triblock copolymeric micelles: Preparation, pharmacokinetics and distribution in vivo. Journal of colloid and interface science 2011; 354(1):116-23.

it will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A composition, comprising:
   a microvesicle derived from an edible plant and comprising a lipid bilayer; and
   a plasma membrane covering, placed, and/or attached to the lipid bilayer of the microvesicle, the plasma membrane derived from an activated leukocyte; and wherein the plasma membrane comprises enhanced expression of chemokine receptors relative to plasma membrane from non-activated leukocytes.

2. The composition of claim 1, wherein the microvesicle encapsulates a therapeutic agent.

3. The composition of claim 1, wherein the edible plant is a fruit or a vegetable.

4. The composition of claim 3, wherein the fruit is selected from the group consisting of a grape, a grapefruit, and a tomato.

5. The composition of claim 2, wherein the therapeutic agent is selected from the group consisting of a phytochemical agent and a chemotherapeutic agent.

6. The composition of claim 5, wherein the therapeutic agent is a phytochemical agent, and wherein the phytochemical agent is selected from the group consisting of curcumin, resveratrol, baicalein, equol, fisetin, and quercetin.

7. The composition of claim 5, wherein the therapeutic agent is a chemotherapeutic agent, and wherein the chemotherapeutic agent is selected from the group consisting of retinoic acid, 5-fluorouracil, vincristine, actinomycin D, adriamycin, cisplatin, docetaxel, doxorubicin, and taxol.

8. The composition of claim 2, wherein the therapeutic agent comprises a nucleic acid molecule selected from the group consisting of an siRNA, a microRNA, and a mammalian expression vector.

9. A pharmaceutical composition, comprising a composition according to claim 1 and a pharmaceutically-acceptable vehicle, carrier, or excipient.

10. A method for treating an inflammatory disorder, comprising administering to a subject in need thereof an effective amount of a composition of claim 1, wherein the treating comprises ameliorating or relieving one or more symptoms associated with the inflammatory disorder.

11. A method for treating a cancer in a subject, comprising administering to a subject an effective amount of a composition according to claim 1, wherein the treating comprises ameliorating or relieving one or more symptoms associated with the cancer.

* * * * *